(12) United States Patent
Otten et al.

(10) Patent No.: US 6,262,074 B1
(45) Date of Patent: Jul. 17, 2001

(54) 4-HETAROYLPYRAZOL DERIVATIVES AND THE USE THEREOF AS HERBICIDES

(75) Inventors: Martina Otten, Ludwigshafen; Norbert Götz, Worms; Wolfgang von Deyn, Neustadt; Stefan Engel, Idstein; Uwe Kardorff, Mannheim; Michael Rack, Heidelberg; Regina Luise Hill, Speyer; Peter Plath, Frankenthal; Matthias Witschel, Ludwigshafen; Karl-Otto Westphalen, Speyer; Helmut Walter, Obrigheim; Ulf Misslitz, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/254,974
(22) PCT Filed: Sep. 9, 1997
(86) PCT No.: PCT/EP97/04910
§ 371 Date: Mar. 17, 1999
§ 102(e) Date: Mar. 17, 1999
(87) PCT Pub. No.: WO98/12192
PCT Pub. Date: Mar. 26, 1998

(30) Foreign Application Priority Data

Sep. 20, 1996 (DE) ............................. 196 38 484

(51) Int. Cl.[7] .................. A61K 31/47; A61K 31/44; C07D 217/22; C07D 215/12; C07D 215/20
(52) U.S. Cl. .................. 514/314; 514/307; 514/309; 514/310; 514/312; 514/313; 546/141; 546/143; 546/146; 546/148; 546/153; 546/159; 546/164; 546/165; 546/168
(58) Field of Search ................... 546/156, 141, 546/143, 146, 148, 153, 159, 164, 165, 168; 514/307, 309, 310, 312, 313, 314

(56) References Cited

U.S. PATENT DOCUMENTS 4,832,731 * 5/1989 Plath et al. .
5,952,266 * 9/1999 Tseng ................................. 504/288

FOREIGN PATENT DOCUMENTS

0629623 * 12/1994 (EP) .
629623    12/1994 (EP) .
94/01431 * 7/1992 (WO) .
94/01431    1/1994 (WO) .
96/26206 * 8/1996 (WO) .
97/01550 * 1/1997 (WO) .
97/08164 * 3/1997 (WO) .

OTHER PUBLICATIONS

Kawakubo et al., *Plant Physiol,* 1979, 64, 774–779.
Plant Physiol., vol. 64, pp. 774–779, 1979, Kawakubo.*

* cited by examiner

*Primary Examiner*—D. Margaret Seaman
(74) *Attorney, Agent, or Firm*—Keil & Weinkauf

(57) ABSTRACT

Hetaroyl derivatives of the formula I

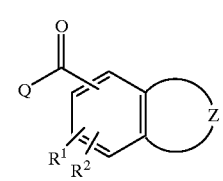

where:

$R^1$ and $R^2$ are each hydrogen, nitro, halogen, cyano, thiocyanato, hydroxyl, mercapto, $C_1$–$C_6$-alkyl, $C_1$–$C_6$-alkoxy, $C_1$–$C_6$-alkylthio, $C_1$–$C_6$-alkylsulfinyl, $C_1$–$C_6$-alkylsulfonyl or $C_1$–$C_6$-alkoxysulfonyl, where the last 6 radicals may be substituted and/or functionalized; phenyl, phenoxy, phenylthio, phenylsulfinyl or phenylsulfonyl, where the last 5 radicals may be substituted;

Z is an unsubstituted or substituted four-membered unsaturated, partially or fully saturated chain consisting of three carbons and one nitrogen;

Q is unsubstituted or substituted hydroxypyrazole linked at position 4;

and their agriculturally useful salts.

A process for preparing the hetaroyl derivatives, compositions comprising them, and the use of these derivatives or these compositions comprising them for controlling undesirable plants.

17 Claims, No Drawings

4-HETAROYLPYRAZOL DERIVATIVES AND THE USE THEREOF AS HERBICIDES

Hetaroyl Derivatives

The present invention relates to novel hetaroyl derivatives of the formula I

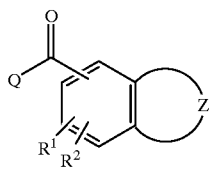

where $R^1$ and $R^2$ are each hydrogen, nitro, halogen, cyano, thiocyanato, hydroxyl, mercapto, $C_1$–$C_6$-alkyl, $C_1$–$C_6$-haloalkyl, $C_2$–$C_6$-alkenyl, $C_2$–$C_6$-alkynyl, $C_1$–$C_6$-alkoxy, $Cl$–$C_6$-haloalkoxy, $C_2$–$C_6$-alkenyloxy, $C_2$–$C_6$-alkynyloxy, $Cl$–$C_6$-alkylthio, $C_1$–$C_6$-haloalkylthio, $C_2$–$C_6$-alkenylthio, $C_2$–$C_6$-alkynylthio, $C_1$–$C_6$-alkylsulfinyl, $C_1$–$C_6$-haloalkylsulfinyl, $C_2$–$C_6$ alkenylsulfinyl, $C_2$–$C_6$ alkynylsulfinyl, $C_1$–$C_6$ alkylsulfonyl, $C_1$–$C_6$ haloalkylsulfonyl, $C_2$–$C_6$-alkenylsulfonyl, $C_2$–$C_6$-alkynylsulfonyl, $C_1$–$C_6$-alkoxysulfonyl, $C_1$–$C_6$-haloalkoxysulfonyl, $C_2$–$C_6$-alkenyloxysulfonyl, $C_2$–$C_6$-alkynyloxysulfonyl, phenyl, phenyloxy, phenylthio, phenylsulfinyl or phenylsulfonyl, where the last five substituents may be partially or fully halogenated and may carry one to three of the following groups: nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

Z is a building block from the group consisting of $Z^1$ to $Z^{12}$

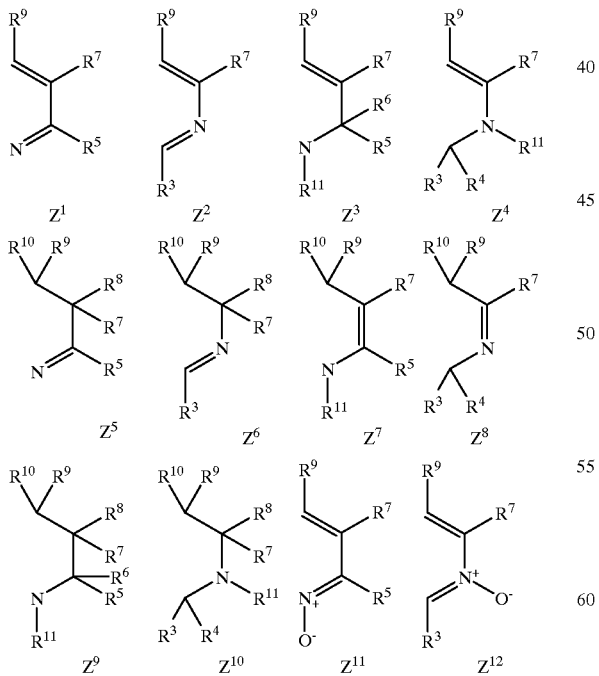

where $R^3$, $R^5$, $R^7$ and $R^9$ are each nitro, cyano, hydroxyl, mercapto, $C_2$–$C_4$-alkenyl, $C_2$–$C_4$-alkynyl, $C_2$–$C_4$-alkenyloxy, $C_2$–$C_4$-alkynyloxy, $C_2$–$C_4$-alkenylthio, $C_2$_$C_4$-alkynylthio, $C_1$–$C_4$-alkylsulfinyl, $C_1$–$C_4$-haloalkylsulfinyl, $C_2$–$C_4$-alkenylsulfinyl, $C_2$–$C_4$-alkynylsulfinyl, $C_1$–$C_4$-alkylsulfonyl, $C_1$–$C_4$-haloalkylsulfonyl, $C_2$–$C_4$-alkenylsulfonyl, $C_2$–$C_4$-alkynylsulfonyl, $C_1$–$C_4$-alkoxysulfonyl, $C_1$–$C_4$-haloalkoxysulfonyl, $C_2$–$C_4$-alkenyloxysulfonyl, $C_2$_$C_4$-alkynyloxysulfonyl, —$NR^{12}R^{13}$, —$CO_2R^{12}$, —$CONR^{12}R^{13}$, phenyl, phenoxy, phenylthio, phenylsulfinyl or phenylsulfonyl, where the last five substituents may be partially or fully halogenated and may carry one to three of the following groups: nitro, cyano, hydroxyl, $Cl$–$C_4$-alkyl, $C_1$–$C_4$-haloalkyl, $C_1$–$C_4$-alkoxy, $C_1$–$C_4$-haloalkoxy; or one of the radicals mentioned under $R^4$;

$R^4$, $R^{6'}$ $R^8$ and $R^{10}$ are each hydrogen, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

or a —$CR^3R^4$—, —$CR^5R^6$—, —$CR^7R^8$— or —$CR^9R^{10}$— unit may be replaced by $C=O$ or $C=NR^{13}$;

$R^{11}$ is hydrogen, $C_1$–$C_6$-alkyl, $C_1$–$C_6$-haloalkyl, $C_3$–$C_6$-alkenyl, $C_3$–$C_6$-alkynyl, $C_1$–$C_6$-alkylcarbonyl, $C_1$–$C_6$-haloalkylcarbonyl, —$CO_2R^{12}$, —$CONR^{12}R^{13}$ or $SO_2R^{12}$;

$R^{12}$ is hydrogen, $C_1$–$C_6$-alkyl, $C_1$–$C_6$-haloalkyl, $C_3$–$C_6$-alkenyl, $C_3$–$C_6$-alkynyl or phenyl, where the last radical may be partially or fully halogenated and may carry one to three of the following radicals: nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

$R^{13}$ is $C_1$–$C_6$-alkoxy, $C_1$–$C_6$-haloalkoxy, $C_3$–$C_6$-alkenyloxy, $C_3$–$C_6$-alkynyloxy or one of the radicals mentioned under $R^{12}$;

Q is a hydroxypyrazole, linked through position 4, of the formula II

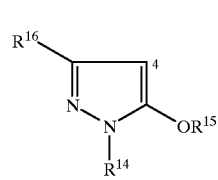

where $R^{14}$ is $C_1$–$C_6$-alkyl, $C_1$–$C_6$-haloalkyl or phenyl, where the last radical may be partially or fully halogenated and may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

$R^{15}$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenyl-$C_1$–$C_4$-alkyl, phenylcarbonyl-$C_1$–$C4$-alkyl, phenylcarbonyl, phenoxycarbonyl or phenylsulfonyl, where the last five substituents may be partially or fully halogenated and may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

$R^{16}$ is hydrogen, $C_1$–$C_6$-alkyl or $C_1$–$C_6$-haloalkyl; and their agriculturally useful salts.

The invention additionally relates to processes for preparing compounds of the formula I, to compositions comprising compounds of the formula I and to the use of these derivatives or to compositions comprising these derivatives for controlling harmful plants.

2-Hetaroylpyrazoles are known from the literature, for example from WO 94/01431 and WO 93/18031.

However, the herbicidal properties of these prior art compounds and their compatibility with crop plants are not entirely satisfactory. It is an object of the present invention to provide novel, in particular herbicidally active, compounds having improved properties.

We have found that this object is achieved by the hetaroyl derivatives of the formula I and their herbicidal action.

Furthermore, the invention provides herbicidal compositions comprising the compounds I and having a very good herbicidal activity. Additionally, the invention provides processes for preparing these compositions and methods for controlling undesirable plant growth using the compounds I.

Depending on the substitution pattern, the compounds of the formula I may contain one or more chiral centers and, if this is the case, be present as enantiomers or as mixtures of diastereomers. The invention provides the pure enantiomers or diastereomers and mixtures thereof.

The compounds of the formula I may also be present in the form of their agriculturally useful salts, the kind of salt generally not being important. The salts of those cations or the acid addition salts of those acids whose cations or anions, respectively, do is not adversely affect the herbicidal activity of the compounds I are generally suitable.

Suitable cations are in particular ions of the alkali metals, preferably lithium, sodium and potassium, of the alkaline earth metals, preferably calcium and magnesium, and of the transition metals, preferably manganese, copper, zinc and iron, and ammonium which may, if desired, carry one to four $C_1$–$C_4$-alkyl substituents and/or one phenyl or benzyl substituent, preferably diisopropylammonium, tetramethylammonium, tetrabutylammonium, trimethylbenzylammonium, and further phosphonium ions and sulfonium ions, preferably tri($C_1$–$C_4$-alkyl)sulfonium and sulfoxonium ions, preferably tri($C_1$–$C_4$-alkyl) sulfoxonium. Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, ropionate and butyrate.

The organic moieties mentioned for the substituents $R^1$–$Rl^6$ or as radicals on phenyl rings represent collective terms for lists of the individual group members. All hydrocarbon chains, ie. all the alkyl, phenylalkyl, phenylcarbonylalkyl, haloalkyl, alkoxy, aloalkoxy, alkylthio, haloalkylthio, alkylsulfinyl, haloalkylsulfinyl, alkylsulfonyl, haloalkylsulfonyl, alkoxysulfonyl, haloalkoxysulfonyl, alkylcarbonyl, haloalkylcarbonyl, alkoxycarbonyl, alkenyl, alkenyloxy, alkenylthio, alkenylsulfinyl, alkenylsulfonyl, alkenyloxysulfonyl, alkynyl, alkynyloxy, alkynylthio, alkynylsulfinyl, alkynylsulfonyl and alkynyloxysulfonyl moieties, ay be straight-chain or branched. Unless stated otherwise, reference is given to halogenated substituents carrying one to five identical or different halogens. Halogen is in each case fluorine, chlorine, bromine or iodine.

Furthermore, the following moieties represent, for example:

$C_1$–$C_4$-alkyl and the alkyl moieties of $C_1$–$C_4$-alkylcarbonyl, phenyl-$C_1$–$C_4$-alkyl and phenylcarbonyl-$C_1$–$C_4$-alkyl: methyl, ethyl, propyl, 1-methylethyl, butyl, 1-methylpropyl, 2-methylpropyl and 1,1-dimethylethyl;

$C_1$–$C_6$-alkyl and the alkyl moieties of $C_1$–$C_6$-alkylcarbonyl: $C_1$–$C_4$-alkyl as mentioned above, and pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl and the haloalkyl moieties of $C_1$–$C_4$-haloalkylcarbonyl: a $C_1$–$C_4$-alkyl radical as mentioned above which is partially or fully substituted by fluorine, chlorine, bromine and/or iodine, ie. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl and the haloalkyl moieties of $C_1$–$C_6$-haloalkylcarbonyl: $C_1$–$C_4$-haloalkyl as mentioned above, and 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-alkoxy and the alkoxy moieties in $C_1$–$C_4$-alkoxycarbonyl; methoxy, ethoxy, propoxy, 1-methylethoxy, butoxy, 1-methylpropoxy, 2-methylpropoxy and 1,1-dimethylethoxy;

$C_1$–$C_6$-alkoxy and the alkoxy moieties in $C_1$–$C_6$-alkoxycarbonyl: $C_1$–$C_4$-alkoxy as mentioned above, and pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, ie. for example fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_6$-haloalkoxy: $C_1$–$C_4$-haloalkoxy as mentioned above, and 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$–$C_4$-alkylthio: methylthio, ethylthio, propylthio, 1-methylethylthio, butylthio, 1-methylpropylthio, 2-methylpropylthio and 1,1-dimethylethylthio;

$C_1$–$C_6$-alkylthio: $C_1$–$C_4$-alkylthio as mentioned above, and pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_4$-haloalkylthio: a $C_1$-$C_4$-alkylthio radical as mentioned above which is partially or fully substituted by fluorine, chlorine, bromine and/or iodine, ie. for example fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$–$C_6$-haloalkylthio: $C_1$–$C_4$-haloalkylthio as mentioned above, and 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio and dodecafluorohexylthio;

$C_1$–$C_4$-alkylsulfinyl ($C_1$–$C_4$-alkyl-S(=O)—): methylsulfinyl, ethylsulfinyl, propylsulfinyl, 1-methylethylsulfinyl, butylsulfinyl, 1-methylpropylsulfinyl, 2-methylpropylsulfinyl and 1,1-dimethylethylsulfinyl;

$C_1$–$C_6$-alkylsulfinyl: $C_1$–$C_4$-alkylsulfinyl as mentioned above, and pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$–$C_4$-haloalkylsulfinyl: a $C_1$–$C_4$-alkylsulfinyl radical as mentioned above which is partially or fully substituted by fluorine, chlorine, bromine and/or iodine, ie. fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl and nonafluorobutylsulfinyl;

$C_1$–$C_6$-haloalkylsulfinyl: $C_1$–$C_4$-haloalkylsulfinyl as mentioned above, and 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl and dodecafluorohexylsulfinyl;

$C_1$–$C_4$-alkylsulfonyl ($C_1$–$C_4$-alkyl-S(=O)$_2$—): methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl: $C_1$–$C_4$-alkylsulfonyl as mentioned above, is and pentylsulfonyl, 1-methylbutylsulfonyl, 2-methylbutylsulfonyl, 3-methylbutylsulfonyl, 2,2-dimethylpropylsulfonyl, l-ethylpropylsulfonyl, 1,1-dimethylpropylsulfonyl, 1,2-dimethylpropylsulfonyl, n-hexylsulfonyl, 1-methylpentylsulfonyl, 2-methylpentylsulfonyl, 3-methylpentylsulfonyl, 4-methylpentylsulfonyl, 1,l-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, l-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_4$-haloalkylsulfonyl: a $C_1$–$C_4$-alkylsulfonyl radical as mentioned above which is partially or fully substituted by fluorine, chlorine, bromine and/or iodine, ie.

fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(choromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl and nonafluorobutylsulfonyl;

$C_1$–$C_6$-haloalkylsulfonyl: $C_1$–$C_4$-haloalkylsulfonyl as mentioned above, and 5-fluorbpentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and didecafluorohexylsulfonyl [sic];

$C_1$–$C_4$-alkoxysulfonyl: methoxysulfonyl, ethoxysulfonyl, propoxysulfonyl, 1-methylethoxysulfonyl, butoxysulfonyl, 1-methylpropoxysulfonyl, 2-methylpropoxysulfonyl and 1,1-dimethylethoxysulfonyl;

$C_1$–$C_6$-alkoxysulfonyl: $C_1$–$C_4$-alkoxysulfonyl as mentioned above, and pentoxysulfonyl, 1-methylbutoxysulfonyl, 2-methylbutoxysulfonyl, 3-methylbutoxysulfonyl, 1,1-dimethylpropoxysulfonyl, 1,2-dimethylpropoxysulfonyl, 2,2-dimethylpropoxysulfonyl, 1-ethylpropoxysulfonyl, hexoxysulfonyl, 1-methylpentoxysulfonyl, 2-methylpentoxysulfonyl, 3-methylpentoxysulfonyl, 4-methylpentoxysulfonyl, 1,1-dimethylbutoxysulfonyl, 1,2-dimethylbutoxysulfonyl, 1,3-dimethylbutoxysulfonyl, 2,2-dimethylbutoxysulfonyl, 2,3-dimethylbutoxysulfonyl, 3,3-dimethylbutoxysulfonyl, 1-ethylbutoxysulfonyl, 2-ethylbutoxysulfonyl, 1,1,2-trimethylpropoxysulfonyl, 1,2,2-trimethylpropoxysulfonyl, 1-ethyl-1-methylpropoxysulfonyl and 1-ethyl-2-methylpropoxysulfonyl;

$C_1$–$C_4$-haloalkoxysulfonyl: a $C_1$–$C_4$-alkoxysulfonyl radical as mentioned above which is partially or fully substituted by fluorine, chlorine, bromine and/or iodine, ie. for example fluoromethoxysulfonyl, difluoromethoxysulfonyl, trifluoromethoxysulfonyl, chlorodifluoromethoxysulfonyl, bromodifluoromethoxysulfonyl, 2-fluoroethoxysulfonyl, 2-chloroethoxysulfonyl, 2-bromoethoxysulfonyl, 2-iodoethoxysulfonyl, 2,2-difluoroethoxysulfonyl, 2,2,2-trifluoroethoxysulfonyl, 2-chloro-2-fluoroethoxysulfonyl, 2-chloro-2,2-difluoroethoxysulfonyl, 2,2-dichloro-2-fluoroethoxysulfonyl, 2,2,2-trichloroethoxysulfonyl, pentafluoroethoxysulfonyl, 2-fluoropropoxysulfonyl, 3-fluoropropoxysulfonyl, 2-chloropropoxysulfonyl, 3-chloropropoxysulfonyl, 2-bromopropoxysulfonyl, 3-bromopropoxysulfonyl, 2,2-difluoropropoxysulfonyl, 2,3-difluoropropoxysulfonyl, 2,3-dichloropropoxysulfonyl, 3,3,3-trifluoropropoxysulfonyl, 3,3,3-trichloropropoxysulfonyl, 2,2,3,3,3-pentafluoropropoxysulfonyl, heptafluoropropoxysulfonyl, 1-(fluoromethyl)-2-fluoroethoxysulfonyl, 1-(chloromethyl)-2-chloroethoxysulfonyl, 1-(bromomethyl)-2-bromoethoxysulfonyl, 4-fluorobutoxysulfonyl, 4-chlorobutoxysulfonyl, 4-bromobutoxysulfonyl and 4-iodobutoxysulfonyl;

$C_1$–$C_6$-haloalkoxysulfonyl: $C_1$–$C_4$-haloalkoxysulfonyl as mentioned above, and 5-fluoropentoxysulfonyl, 5-chloropentoxysulfonyl, 5-bromopentoxysulfonyl, 5-iodopentoxysulfonyl, undecafluoropentoxysulfonyl, 6-fluorohexoxysulfonyl, 6-chlorohexoxysulfonyl, 6-bromohexoxysulfonyl, 6-iodohexoxysulfonyl and dodecafluorohexoxysulfonyl;

$C_3$–$C_4$-alkenyl, and the alkenyl moieties of $C_3$–$C_4$-alkenyloxy, $C_3$–$C_4$-alkenylthio, $C_3$–$C_4$-alkenylsulfinyl, $C_3$–$C_4$-alkenylsulfonyl and $C_3$–$C_4$-alkenyloxysulfonyl: prop---en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl and 2-methylprop-2-en-1-yl;

$C_2$–$C_4$-alkenyl, and the alkenyl moieties of $C_2$–$C_4$-alkenyloxy, $C_2$–$C_4$-alkenylthio, $C_2$–$C_4$-alkenylsulfinyl, $C_2$–$C_4$-alkenylsulfonyl and $C_2$–$C_4$-alkenyloxysulfonyl: $C_3$–$C_4$-alkenyl as mentioned above, and ethenyl;

$C_3$–$C_6$-alkenyl, and the alkenyl moieties of $C_3$–$C_6$-alkenyloxy, $C_3$–$C_6$-alkenylthio, $C_3$–$C_6$-alkenylsulfinyl, $C_2$–$C_6$-alkenylsulfonyl, $C_3$–$C_6$-alkenyloxysulfonyl: $C_3$–$C_4$-alkenyl as mentioned above, and penten-1-yl, penten-2-yl, penten-3-yl, penten-4-yl, 1-methyl-but-1-en-1-yl, 2-methyl-but-1-en-1-yl, 3-methyl-but-1-en-1-yl, 1-methyl-but-2-en-1-yl, 2-methyl-but-2-en-1-yl, 3-methyl-but-2-en-1-yl, 1-methyl-but-3-en-1-yl, 2-methyl-but-3-en-1-yl, 3-methyl-but-3-en-1-yl, 1,1-dimethyl-prop-2-en-1-yl, 1,2-dimethyl-prop-1-en-1-yl, 1,2-dimethyl-prop-2-en-1-yl, 1-ethyl-prop-1-en-2-yl, 1-ethyl-prop-2-en-1-yl, hex---en-1-yl, hex-2-en-1-yl, hex-3-en-1-yl, hex-4-en-1-yl, hex-5-en-1-yl, 1-methylpent---en-i-yl, 2-methylpent-i-en-1-yl, 3-methylpent-i-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-i-en-1-yl, 1,2-dimethylbut-2-en-1-yl, 1,2-dimethylbut-3-en-1-yl, 1,3-dimetylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl and the alkenyl moieties of $C_2$–$C_6$-alkenyloxy, $C_2$–$C_6$-alkenylthio, C2–$C_6$-alkenylsulfinyl, $C_2$–$C_6$-alkenylsulfonyl, $C_2$–$C_6$-alkenyloxysulfonyl: $C_3$–$C_6$-alkenyl as mentioned above, and ethenyl;

$C_3$–$C_4$-alkynyl and the alkynyl radicals of $C_3$–$C_4$-alkynyloxy, $C_3$–$C_4$-alkynylthio, $C_3$–$C_4$-alkynylsulfinyl, $C_3$–$C_4$-alkynylsulfonyl and $C_3$–$C_4$-alkynyloxysulfonyl: prop-1-yn-1-yl, prop-2-yn-1-yl, but-1-yn-1-yl, but-1-yn-3-yl, but-1-yn-4-yl and but-2-yn-1-yl;

$C_2$–$C_4$-alkynyl, and the alkynyl radicals of $C_2$–$C_4$-alkynyloxy, $C_2$–$C_4$-alkynylthio, $C_2$–$C_4$-alkynylsulfinyl, $C_2$–$C_4$-alkynylsulfonyl, $C_2$–$C_4$-alkynyloxysulfonyl: $C_3$–$C_6$-alkynyl as mentioned above, and ethynyl;

$C_3$–$C_6$-alkynyl, and the alkynyl radicals of $C_3$–$C_6$-alkynyloxy, $C_3$–$C_6$-alkynylthio, $C_3$–$C_6$-alkynylsulfinyl, $C_3$–$C_6$-alkynylsulfonyl and $C_3$–$C_6$-alkynyloxysulfonyl: $C_3$–$C_4$-alkynyl as mentioned above, and pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-—-yl, hex-2-yn-4-yl, hex-2-yn-5-yl, hex-2-yn-6-yl, hex-3-yn-—-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_2$–$C_6$-alkynyl, and the alkynyl radicals of C2–$C_6$-alkynyloxy, $C_2$–$C_6$-alkynylthio, $C_2$–$C_6$-alkynylsulfinyl, $C_2$–$C_6$-alkynylsulfonyl, $C_2$–$C_6$-alkynyloxysulfonyl: $C_3$–$C_6$-alkynyl as mentioned above, and ethynyl;

All phenyl rings are preferably unsubstituted or carry one to three halogens and/or a nitro group, a cyano radical, or a methyl, trifluoromethyl, methoxy or trifluoromethoxy substituent.

With respect to the use of the compounds of the formula I according to the invention as herbicides, the variables preferably have the meanings below, in each case on their own or in combination:

$R^1$ is nitro, halogen, hydroxyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylsulfonyl, $C_1$–$C_6$-haloalkylsulfonyl or phenyl, where the last radical is unsubstituted or may carry one to three halogens and/or a nitro group, a cyano radical, or a methyl, trifluoromethyl, methoxy or trifluoromethoxy substituent; particularly preferably nitro, fluorine, chlorine, bromine, hydroxyl, methyl, ethyl, trifluoromethyl, methoxy, ethoxy, difluoromethoxy, trifluoromethoxy, methylsulfonyl, ethylsulfonyl, trifluoromethylsulfonyl, pentafluoroethylsulfonyl or phenyl;

$R^2$ is hydrogen, halogen or $C_1$–$C_6$-alkyl; particularly preferably hydrogen, chlorine, bromine or methyl;

Z is $Z^1$, $Z^2$, $Z^3$, $Z^4$, $Z^5$, $Z^6$, $Z^7$, $Z^8$, $Z^9$, $Z^{10}$, $Z^{11}$ or $Z^{12}$;

$R^3$, $R^5$, $R^7$ and $R^9$ are each hydrogen, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, nitro, cyano, hydroxyl, mercapto, $C_2$–$C_4$-alkenyl, $C_2$–$C_4$-alkynyl, $C_2$–$C_4$-alkenyloxy, $C_2$–$C_4$-alkynyloxy, $C_2$–$C_4$-alkenylthio, $C_2$–$C_4$-alkynylthio, $C_1$–$C_4$-alkylsulfinyl, $C_1$–$C_4$-haloalkylsulfinyl, $C_2$–$C_4$-alkenylsulfinyl, $C_2$–$C_4$-alkynylsulfinyl, $C_1$–$C_4$-alkylsulfonyl, $C_1$–$C_4$-haloalkylsulfonyl, $C_2$–$C_4$-alkenylsulfonyl, $C_2$–$C_4$-alkynyl-sulfonyl, $C_1$–$C_4$-alkoxysulfonyl, $C_1$–$C_4$-haloalkoxysulfonyl, $C_2$–$C_4$-alkenyloxysulfonyl, $C_2$–$C_4$-alkynyloxysulfonyl, -$NR^{12}R^{13}$, —$CO_2R^{12}$, —$CONR^{12}R^{13}$, phenyl, phenoxy, phenylthio, phenyl-sulfinyl or phenylaulfonyl, where the last five substituents may be partially or fully halogenated and may carry one to three of the following groups: nitro, cyano, hydroxyl, $C_1$–$C_4$-alkyl, $C_1$–$C_4$-haloalkyl, $C_1$–$C_4$-alkoxy, $C_1$–$C_4$-haloalkoxy; particularly preferably hydrogen, halogen, $C_1$–$C_4$-alkyl, $C_1$–$C_4$-haloalkyl, $C_1$–$C_4$-alkoxy, $C_1$–$C_4$-haloalkoxy, nitro, cyano, hydroxyl, $C_1$–$C_6$-alkoxycarbonyl or phenyl, where the last radical is unsubstituted or may carry one to three halogens and/or a nitro group, a cyano radical, or a methyl, trifluoromethyl, methoxy or trifluoromethoxy substituent; especially preferably hydrogen, fluorine, chlorine, bromine, methyl, ethyl, trifluoromethyl, methoxy, ethoxy, trifluoromethoxy, difluoromethoxy, nitro, cyano, hydroxyl, methoxycarbonyl, ethoxycarbonyl or phenyl;

$R^4$, $R^6$, $R^8$ and $R^{10}$ are each hydrogen, halogen or $C_1$–$C_4$-alkyl; particularly preferably hydrogen, fluorine, chlorine, methyl or ethyl; especially preferably hydrogen;

$R^{11}$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkylsulfonyl, $C_1$–$C_6$-haloalkylsulfonyl or phenylsulfonyl, where the last phenyl radical may be substituted by a $C_1$–$C_4$-alkyl radical; particularly preferably methyl, ethyl, difluoromethyl, trifluoromethyl, methylcarbonyl, ethylcarbonyl, isopropylcarbonyl, trifluoromethylcarbonyl, methylsulfonyl, trifluoromethylsulfonyl, phenylsulfonyl or 4-methylphenylsulfonyl;

$R^{12}$ is hydrogen or $C_1$–$C_6$-alkyl; particularly preferably hydrogen, methyl or ethyl;

$R^{13}$ is hydrogen, $C_1$–$C_6$-alkyl, $C_1$–$C_6$-alkoxy, $C_3$–$C_6$-alkenyloxy or $C_3$–$C_6$-alkynyloxy; particularly preferably methyl, ethyl, methoxy, ethoxy, 2-propen-1-yloxy, 2-propyn-1-yloxy or 1-methyl-2-propyn-1-yloxy;

$R^{14}$ is $C_1$–$C_6$-alkyl or $C_1$–$C_6$-haloalkyl; particularly preferably methyl, ethyl, propyl, isopropyl, butyl or isobutyl;

$R^{15}$ is hydrogen, $C_1$–$C_6$-alkyl, $C_1$–$C_6$-haloalkyl, $C_1$–$C_6$-alkyl-carbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonyl, phenoxycarbonyl or phenylsulfonyl, where the last three substituents may be partially or fully halogenated and may carry one to three of the following radicals: nitro, cyano, cl–$C_4$-alkyl, $C_1$–$C_4$-haloalkyl, $C_1$–$C_4$-alkoxy, $C_1$–$C_4$-haloalkoxy; particularly preferably hydrogen, $C_1$–$C_6$-alkyl, $C_1$–$C_6$-alkyl-carbonyl, $C_1$–Cf-haloalkylcarbonyl, $C_1$–C6-alkoxycarbonyl, $C_1$–$C_6$-alkylsulfonyl, $C_1$–$C_6$-haloalkylsulfonyl or phenylsulfonyl, where the phenyl ring of the last substituent may be partially or fully halogenated and may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

$R^{16}$ is hydrogen, $C_1$–$C_6$-alkyl or $C_1$–$C_6$-haloalkyl; particularly preferably hydrogen, methyl, ethyl or trifluoromethyl.

Preference is given to compounds of the formula I where the variable Z is $Z^1$, $Z^2$, $Z^{11}$ or $Z^{12}$, especially $Z^1$ or $Z^2$.

Likewise preferred are compounds of the formula I where the variable Z is $Z^3$, $Z^4$, $Z^5$, $Z^6$, $Z^7$ or $Z^8$, especially $Z^3$, $Z^5$, $Z^6$, $Z^7$ or $Z^8$.

Likewise preferred are the compounds of the formula I where the variable z is $Z^9$ or $Z^{10}$.

Particular preference is given to compounds of the formulae Ia–Ic (Z=$Z^1$) and Id—Ie (Z=$Z^2$) and their N-oxides Ia'–Ic' (Z=$Z^{11}$) and Id'–Ie' (Z=$Z^{12}$) and particular preference is also given to compounds of the formulae If (Z=$Z^9$) and Ig (z=$Z^{10}$).

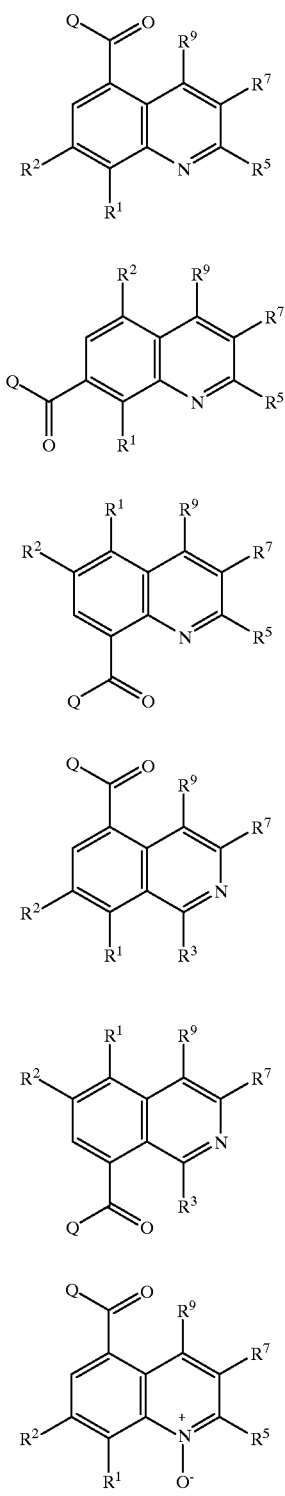

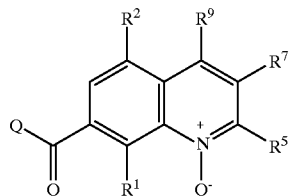

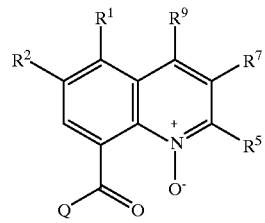

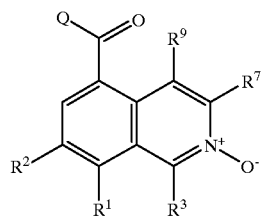

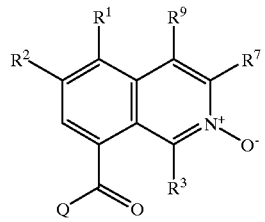

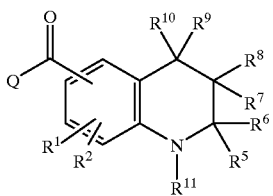

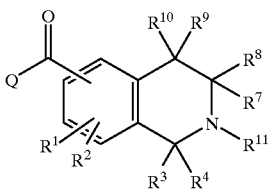

Futhemor, preference is given to the compounds Ia, Ib, Ic, Id and Ie. Likewise, preference is given to the compounds If and Ig where $CR^3R^4$, $CR^5R^6$, $CR^7R^8$ and/or $CR^9R^{10}$ may not be replaced by C=O or C=$NR^{13}$.

Furthermore, preference is given to the compounds If where $CR^5R^6$ is replaced by C=O or C=$NR^{13}$ and to the compounds Ig where $CR^7R^8$ is replaced by C=o or C=$NR^{13}$.

Very particular preference is given to the compounds Ia1 (= I where $R^2$, $R^{15}$ and $R^{16}$=H and $R^{14}$=CH$_3$ and where the "Q—CO—fragment" is attached in position a, $R^1$ is attached in position d and $Z^1$ is attached in positions b and c) listed in Table 1.

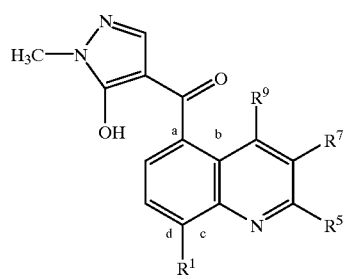

Ia1

TABLE 1

| No. | R¹ | R⁵ | R⁷ | R⁹ |
|---|---|---|---|---|
| Ia1.001 | Br | H | H | H |
| Ia1.002 | Cl | H | H | H |
| Ia1.003 | SO₂CH₃ | H | H | H |
| Ia1.004 | CH₃ | H | H | H |
| Ia1.005 | OH | H | H | H |
| Ia1.006 | OCH₃ | H | H | H |
| Ia1.007 | CF₃ | H | H | H |
| Ia1.008 | NO₂ | H | H | H |
| Ia1.009 | F | H | H | H |
| Ia1.010 | OCF₃ | H | H | H |
| Ia1.011 | C₆H₅ | H | H | H |
| Ia1.012 | Br | H | CH₃ | H |
| Ia1.013 | Cl | H | CH₃ | H |
| Ia1.014 | SO₂CH₃ | H | CH₃ | H |
| Ia1.015 | CH₃ | H | CH₃ | H |
| Ia1.016 | OH | H | CH₃ | H |
| Ia1.017 | OCH₃ | H | CH₃ | H |
| Ia1.018 | CF₃ | H | CH₃ | H |
| Ia1.019 | NO₂ | H | CH₃ | H |
| Ia1.020 | F | H | CH₃ | H |
| Ia1.021 | OCF₃ | H | CH₃ | H |
| Ia1.022 | C₆H₅ | H | CH₃ | H |
| Ia1.023 | Br | CH₃ | H | H |
| Ia1.024 | Cl | CH₃ | H | H |
| Ia1.025 | SO₂CH₃ | CH₃ | H | H |
| Ia1.026 | CH₃ | CH₃ | H | H |
| Ia1.027 | OH | CH₃ | H | H |
| Ia1.028 | OCH₃ | CH₃ | H | H |
| Ia1.029 | CF₃ | CH₃ | H | H |
| Ia1.030 | NO₂ | CH₃ | H | H |
| Ia1.031 | F | CH₃ | H | H |
| Ia1.032 | OCF₃ | CH₃ | H | H |
| Ia1.033 | C₆H₅ | CH₃ | H | H |
| Ia1.034 | Br | H | H | CH₃ |
| Ia1.035 | Cl | H | H | CH₃ |
| Ia1.036 | SO₂CH₃ | H | H | CH₃ |
| Ia1.037 | CH₃ | H | H | CH₃ |
| Ia1.038 | OH | H | H | CH₃ |
| Ia1.039 | OCH₃ | H | H | CH₃ |
| Ia1.040 | CF₃ | H | H | CH₃ |
| Ia1.041 | NO₂ | H | H | CH₃ |
| Ia1.042 | F | H | H | CH₃ |
| Ia1.043 | OCF₃ | H | H | CH₃ |
| Ia1.044 | C₆H₅ | H | H | CH₃ |
| Ia1.045 | Br | CH₃ | CH₃ | CH₃ |
| Ia1.046 | Cl | CH₃ | CH₃ | CH₃ |
| Ia1.047 | SO₂CH₃ | CH₃ | CH₃ | CH₃ |
| Ia1.048 | CH₃ | CH₃ | CH₃ | CH₃ |
| Ia1.049 | OH | CH₃ | CH₃ | CH₃ |
| Ia1.050 | OCH₃ | CH₃ | CH₃ | CH₃ |
| Ia1.051 | CF₃ | CH₃ | CH₃ | CH₃ |
| Ia1.052 | NO₂ | CH₃ | CH₃ | CH₃ |
| Ia1.053 | F | CH₃ | CH₃ | CH₃ |
| Ia1.054 | OCF₃ | CH₃ | CH₃ | CH₃ |
| Ia1.055 | C₆H₅ | CH₃ | CH₃ | CH₃ |
| Ia1.056 | Br | H | Cl | H |
| Ia1.057 | Cl | H | Cl | H |
| Ia1.058 | SO₂CH₃ | H | Cl | H |
| Ia1.059 | CH₃ | H | Cl | H |

TABLE 1-continued

| No. | R¹ | R⁵ | R⁷ | R⁹ |
|---|---|---|---|---|
| Ia1.060 | OH | H | Cl | H |
| Ia1.061 | OCH₃ | H | Cl | H |
| Ia1.062 | CF₃ | H | Cl | H |
| Ia1.063 | NO₂ | H | Cl | H |
| Ia1.064 | F | H | Cl | H |
| Ia1.065 | OCF₃ | H | Cl | H |
| Ia1.066 | C₆H₅ | H | Cl | H |
| Ia1.067 | Br | Cl | H | H |
| Ia1.068 | Cl | Cl | H | H |
| Ia1.069 | SO₂CH₃ | Cl | H | H |
| Ia1.070 | CH₃ | Cl | H | H |
| Ia1.071 | OH | Cl | H | H |
| Ia1.072 | OCH₃ | Cl | H | H |
| Ia1.073 | CF₃ | Cl | H | H |
| Ia1.074 | NO₂ | Cl | H | H |
| Ia1.075 | F | Cl | H | H |
| Ia1.076 | OCF₃ | Cl | H | H |
| Ia1.077 | C₆H₅ | Cl | H | H |
| Ia1.078 | Br | H | H | Cl |
| Ia1.079 | Cl | H | H | Cl |
| Ia1.080 | SO₂CH₃ | H | H | Cl |
| Ia1.081 | CH₃ | H | H | Cl |
| Ia1.082 | OH | H | H | Cl |
| Ia1.083 | OCH₃ | H | H | Cl |
| Ia1.084 | CF₃ | H | H | Cl |
| Ia1.085 | NO₂ | H | H | Cl |
| Ia1.086 | F | H | H | Cl |
| Ia1.087 | OCF₃ | H | H | Cl |
| Ia1.088 | C₆H₅ | H | H | Cl |
| Ia1.089 | Br | Cl | Cl | Cl |
| Ia1.090 | Cl | Cl | Cl | Cl |
| Ia1.091 | SO₂CH₃ | Cl | Cl | Cl |
| Ia1.092 | CH₃ | Cl | Cl | Cl |
| Ia1.093 | OH | Cl | Cl | Cl |
| Ia1.094 | OCH₃ | Cl | Cl | Cl |
| Ia1.095 | CF₃ | Cl | Cl | Cl |
| Ia1.096 | NO₂ | Cl | Cl | Cl |
| Ia1.097 | F | Cl | Cl | Cl |
| Ia1.098 | OCF₃ | Cl | Cl | Cl |
| Ia1.099 | C₆H₅ | Cl | Cl | Cl |
| Ia1.100 | Br | C₆H₅ | H | H |
| Ia1.101 | Cl | C₆H₅ | H | H |
| Ia1.102 | SO₂CH₃ | C₆H₅ | H | H |
| Ia1.103 | CH₃ | C₆H₅ | H | H |
| Ia1.104 | OH | C₆H₅ | H | H |
| Ia1.105 | OCH₃ | C₆H₅ | H | H |
| Ia1.106 | CF₃ | C₆H₅ | H | H |
| Ia1.107 | NO₂ | C₆H₅ | H | H |
| Ia1.108 | F | C₆H₅ | H | H |
| Ia1.109 | OCF₃ | C₆H₅ | H | H |
| Ia1.110 | C₆H₅ | C₆H₅ | H | H |
| Ia1.111 | Br | CH₃ | OH | H |
| Ia1.112 | Cl | CH₃ | OH | H |
| Ia1.113 | SO₂CH₃ | CH₃ | OH | H |
| Ia1.114 | CH₃ | CH₃ | OH | H |
| Ia1.115 | OH | CH₃ | OH | H |
| Ia1.116 | OCH₃ | CH₃ | OH | H |
| Ia1.117 | CF₃ | CH₃ | OH | H |
| Ia1.118 | NO₂ | CH₃ | OH | H |
| Ia1.119 | F | CH₃ | OH | H |
| Ia1.120 | OCF₃ | CH₃ | OH | H |
| Ia1.121 | C₆H₅ | CH₃ | OH | H |
| Ia1.122 | Br | CF₃ | H | H |
| Ia1.123 | Cl | CF₃ | H | H |
| Ia1.124 | SO₂CH₃ | CF₃ | H | H |
| Ia1.125 | CH₃ | CF₃ | H | H |
| Ia1.126 | OH | CF₃ | H | H |
| Ia1.127 | OCH₃ | CF₃ | H | H |
| Ia1.128 | CF₃ | CF₃ | H | H |
| Ia1.129 | NO₂ | CF₃ | H | H |
| Ia1.130 | F | CF₃ | H | H |
| Ia1.131 | OCF₃ | CF₃ | H | H |
| Ia1.132 | C₆H₅ | CF₃ | H | H |
| Ia1.133 | Br | CH₃ | H | OH |
| Ia1.134 | Cl | CH₃ | H | OH |
| Ia1.135 | SO₂CH₃ | CH₃ | H | OH |
| Ia1.136 | CH₃ | CH₃ | H | OH |

TABLE 1-continued

| No. | R¹ | R⁵ | R⁷ | R⁹ |
|---|---|---|---|---|
| Ia1.137 | OH | CH₃ | H | OH |
| Ia1.138 | OCH₃ | CH₃ | H | OH |
| Ia1.139 | CF₃ | CH₃ | H | OH |
| Ia1.140 | NO₂ | CH₃ | H | OH |
| Ia1.141 | F | CH₃ | H | OH |
| Ia1.142 | OCF₃ | CH₃ | H | OH |
| Ia1.143 | C₆H₅ | CH₃ | H | OH |
| Ia1.144 | Br | H | H | OCH₃ |
| Ia1.145 | Cl | H | H | OCH₃ |
| Ia1.146 | SO₂CH₃ | H | H | OCH₃ |
| Ia1.147 | CH₃ | H | H | OCH₃ |
| Ia1.148 | OH | H | H | OCH₃ |
| Ia1.149 | OCH₃ | H | H | OCH₃ |
| Ia1.150 | CF₃ | H | H | OCH₃ |
| Ia1.151 | NO₂ | H | H | OCH₃ |
| Ia1.152 | F | H | H | OCH₃ |
| Ia1.153 | H | H | H | OCH₃ |
| Ia1.154 | OCF₃ | H | H | OCH₃ |
| Ia1.155 | C₆H₅ | H | H | OCH₃ |
| Ia1.156 | Br | Cl | Cl | CH₃ |
| Ia1.157 | Cl | Cl | Cl | CH₃ |
| Ia1.158 | SO₂CH₃ | Cl | Cl | CH₃ |
| Ia1.159 | CH₃ | Cl | Cl | CH₃ |
| Ia1.160 | OH | Cl | Cl | CH₃ |
| Ia1.161 | OCH₃ | Cl | Cl | CH₃ |
| Ia1.162 | CF₃ | Cl | Cl | CH₃ |
| Ia1.163 | NO₂ | Cl | Cl | CH₃ |
| Ia1.164 | F | Cl | Cl | CH₃ |
| Ia1.165 | OCF₃ | Cl | Cl | CH₃ |
| Ia1.166 | C₆H₅ | Cl | Cl | CH₃ |
| Ia1.167 | Br | CF₃ | H | Br |
| Ia1.168 | Cl | CF₃ | H | Br |
| Ia1.169 | SO₂CH₃ | CF₃ | H | Br |
| Ia1.170 | CH₃ | CF₃ | H | Br |
| Ia1.171 | OH | CF₃ | H | Br |
| Ia1.172 | OCH₃ | CF₃ | H | Br |
| Ia1.173 | CF₃ | CF₃ | H | Br |
| Ia1.174 | NO₂ | CF₃ | H | Br |
| Ia1.175 | F | CF₃ | H | Br |
| Ia1.176 | H | CF₃ | H | Br |
| Ia1.177 | OCF₃ | CF₃ | H | Br |
| Ia1.178 | C₆H₅ | CF₃ | H | Br |
| Ia1.179 | Br | OH | CN | H |
| Ia1.180 | Cl | OH | CN | H |
| Ia1.181 | SO₂CH₃ | OH | CN | H |
| Ia1.182 | CH₃ | OH | CN | H |
| Ia1.183 | OH | OH | CN | H |
| Ia1.184 | OCH₃ | OH | CN | H |
| Ia1.185 | CF₃ | OH | CN | H |
| Ia1.186 | NO₂ | OH | CN | H |
| Ia1.187 | F | OH | CN | H |
| Ia1.188 | OCF₃ | OH | CN | H |
| Ia1.189 | C₆H₅ | OH | CN | H |
| Ia1.190 | Br | H | CF₃ | H |
| Ia1.191 | Cl | H | CF₃ | H |
| Ia1.192 | SO₂CH₃ | H | CF₃ | H |
| Ia1.193 | CH₃ | H | CF₃ | H |
| Ia1.194 | OH | H | CF₃ | H |
| Ia1.195 | OCH₃ | H | CF₃ | H |
| Ia1.196 | CF₃ | H | CF₃ | H |
| Ia1.197 | NO₂ | H | CF₃ | H |
| Ia1.198 | F | H | CF₃ | H |
| Ia1.199 | OCF₃ | H | CF₃ | H |
| Ia1.200 | C₆H₅ | H | CF₃ | H |
| Ia1.201 | Br | H | H | NO₂ |
| Ia1.202 | Cl | H | H | NO₂ |
| Ia1.203 | SO₂CH₃ | H | H | NO₂ |
| Ia1.204 | CH₃ | H | H | NO₂ |
| Ia1.205 | OH | H | H | NO₂ |
| Ia1.206 | OCH₃ | H | H | NO₂ |
| Ia1.207 | CF₃ | H | H | NO₂ |
| Ia1.208 | NO₂ | H | H | NO₂ |
| Ia1.209 | F | H | H | NO₂ |
| Ia1.210 | OCF₃ | H | H | NO₂ |
| Ia1.211 | C₆H₅ | H | H | NO₂ |

Furthermore, very particular preference is given to the following hetaroyl derivatives of the formula I:

the compounds Ia2.001–Ia2.211, which differ from the corresponding compounds Ia1.001–Ia1.211 in that $R^{14}$ is ethyl:

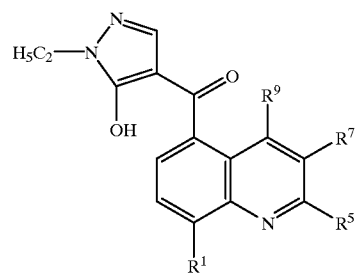

Ia2 the compounds Ia3.001–Ia3.211, which differ from the corresponding compounds Ia1.001–Ia1.211 in that $R^{15}$ is methyl:

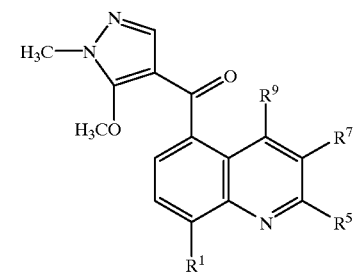

Ia3 the compounds Ia4.001–Ia4.211, which differ from the corresponding compounds Ia1.001–Ia1.211 in that $R^{14}$ is ethyl and $R^{15}$ is methyl:

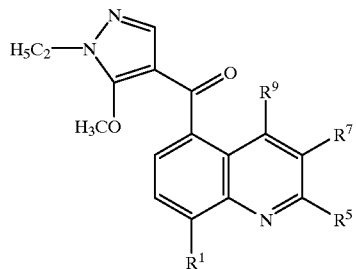

Ia4 the compounds Ia5.001–Ia5.211, which differ from the corresponding compounds Ia1.001–Ia1.211 in that $R^{15}$ is ethyl:

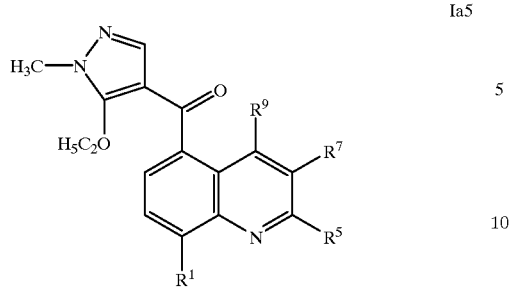

Ia5 the compounds Ia6.001–Ia6.211, which differ from the corresponding compounds Ia1.001–Ia1.211 in that $R^{14}$ and $R^{15}$ are each ethyl:

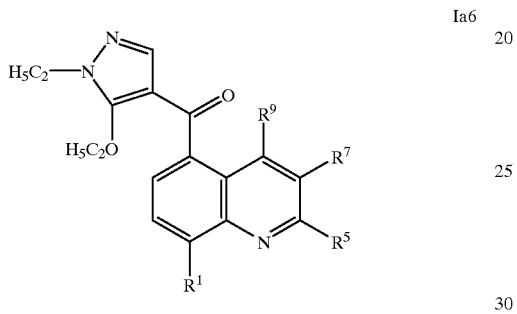

Ia6 the compounds Ia7.001–Ia7.211, which differ from the corresponding compounds Ia1.001–Ia1.211 in that $R^{15}$ is n-propyl:

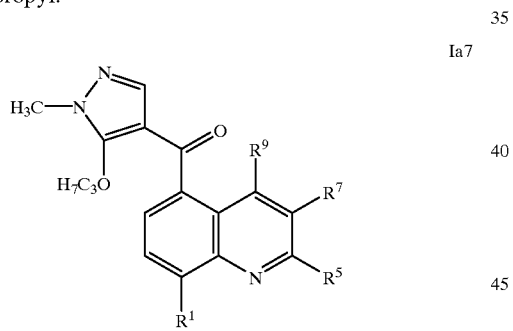

Ia7 the compounds Ia8.001–Ia8.211, which differ from the compounds Ia1.001–Ia1.211 in that $R^{14}$ is ethyl and $R^{15}$ is n-propyl:

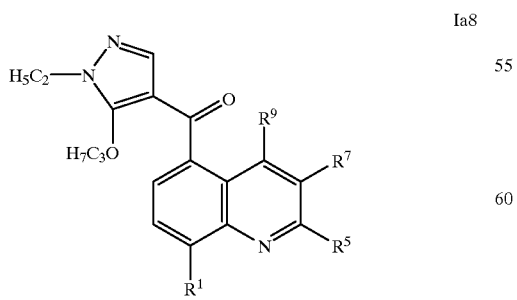

Ia8 the compounds Ia9.001–Ia9.211, which differ from the compounds Ia1.001–Ia1.211 in that $R^{15}$ is n-butyl:

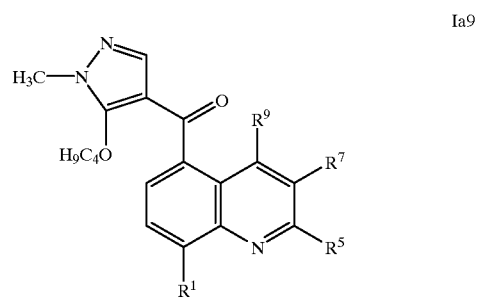

Ia9 the compounds Ia10.001–Ia10.211, which differ from the compounds Ia1.001–Ia1.211 in that $R^{14}$ is ethyl and $R^{15}$ is n-butyl:

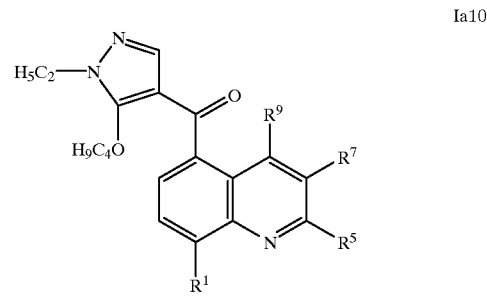

Ia10 the compounds Ia11.001–Ia11.211, which differ from the compounds Ia1.001–Ia1.211 in that $R^{15}$ is methylcarbonyl:

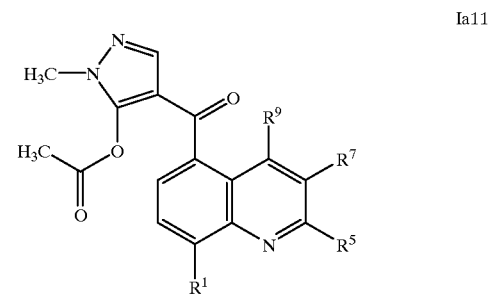

Ia11 the compounds Ia12.001–Ia12.211, which differ from the compounds Ia1.001–Ia1.211 in that $R^{14}$ is ethyl and $R^{15}$ is methylcarbonyl:

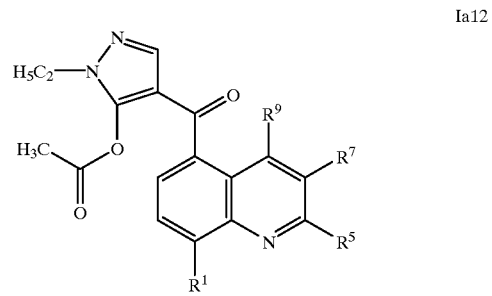

Ia12 the compounds Ia13.001–Ia13.211, which differ from the compounds Ia1.001–Ia1.211 in that $R^{15}$ is ethylcarbonyl:

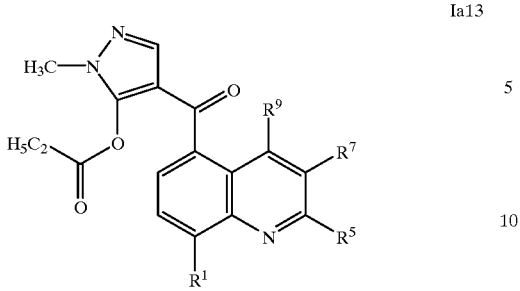

Ia13 the compounds Ia14.001–Ia14.211, which differ from the compounds Ia1.001–Ia1.211 in that $R^{14}$ is ethyl and $R^{15}$ is ethylcarbonyl:

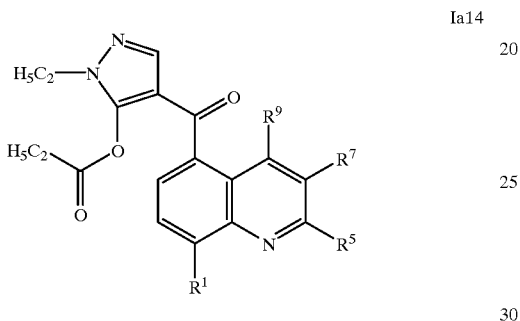

Ia14 the compounds Ia15.001–Ia15.211, which differ from the compounds Ia1.001–Ia1.211 in that $R^{15}$ is n-propylcarbonyl:

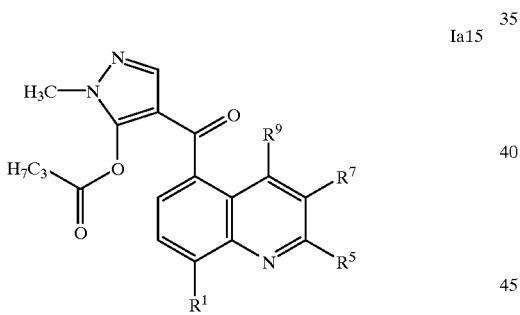

Ia15 the compounds Ia1.6.001–Ia16.211, which differ from the compounds Ia1.001–Ia1.211 in that $R^{14}$ is ethyl and $R^{15}$ is n-propylcarbonyl:

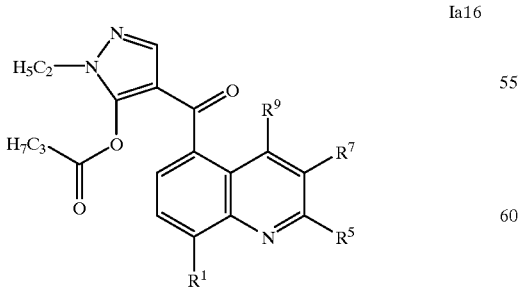

Ia16 the compounds Ia17.001–Ia17.211, which differ from the compounds Ia1.001–Ia1.211 in that $R^{15}$ is n-butylcarbonyl:

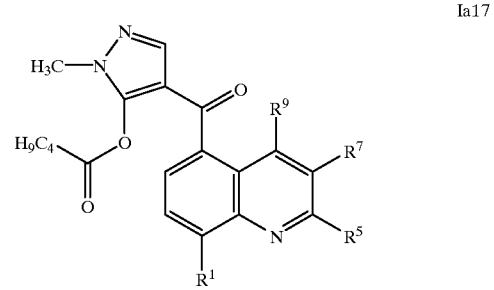

Ia17 the compounds Ia18.001–Ia18.211, which differ from the compounds Ia1.001–Ia1.211 in that $R^{14}$ is ethyl and $R^{15}$ is n-butylcarbonyl:

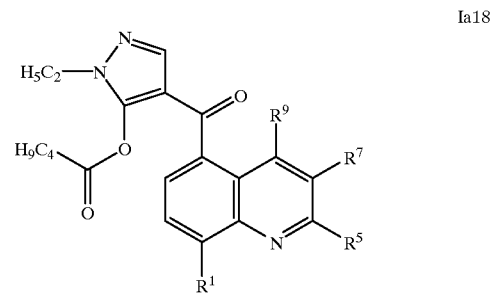

Ia18 the compounds Ia19.001–Ia19.211, which differ from the compounds Ia1.001–Ia1.211 in that $R^{15}$ is trifluoromethylcarbonyl:

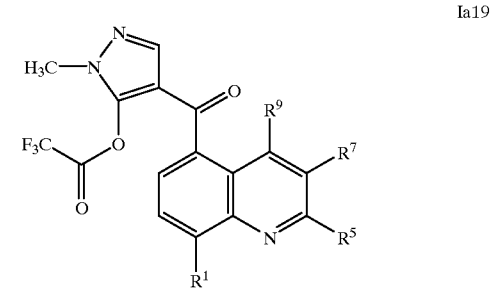

Ia19 the compounds Ia20.001–Ia20.211, which differ from the compounds Ia1.001–Ia1.211 in that $R^{14}$ is ethyl and $R^{15}$ is trifluorocarbonyl:

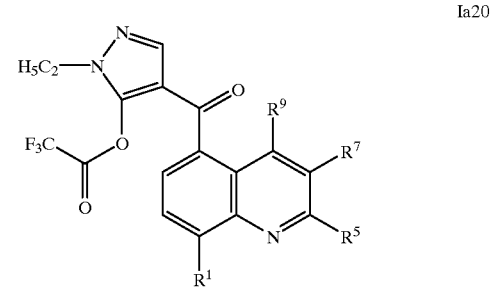

Ia20 the compounds Ia21.001–Ia21.211, which differ from the compounds Ia1.001–Ia1.211 in that $R^{15}$ is methylsulfonyl:

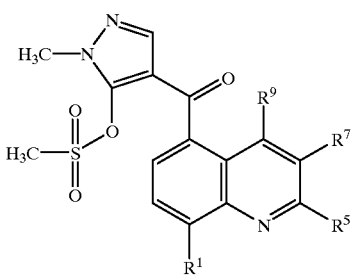

Ia21 the compounds Ia22.001–Ia22.211, which differ from the compounds Ia1.001–Ia1.211 in that $R^{14}$ is ethyl and $R^{15}$ is methylsulfonyl:

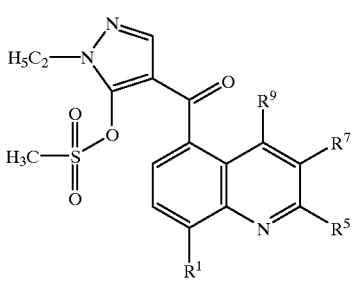

Ia22 the compounds Ia23.001–Ia23.211, which differ from the compounds Ia1.001–Ia1.211 in that $R^{15}$ is ethylsulfonyl:

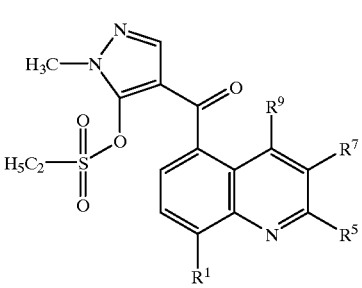

Ia23 the compounds Ia24.001–Ia24.211, which differ from the compounds Ia1.001–Ia1.211 in that $R^{14}$ is ethyl and $R^{15}$ is ethylsulfonyl:

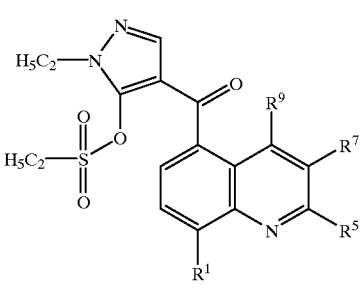

Ia24 the compounds Ia25.001–Ia25.211, which differ from the compounds Ia1.001–Ia1.211 in that $R^{15}$ is n-propylsulfonyl:

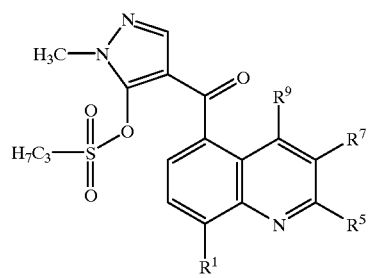

Ia25 the compounds Ia26.001–Ia26.211, which differ from the compounds Ia1.001–Ia1.211 in that $R^{14}$ is ethyl and $R^{15}$ is n-propylsulfonyl:

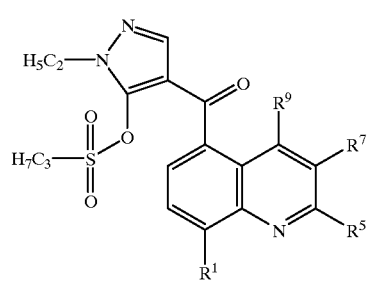

Ia26 the compounds Ia27.001–Ia27.211, which differ from the compounds Ia1.001–Ia1.211 in that $R^{15}$ is n-butylsulfonyl:

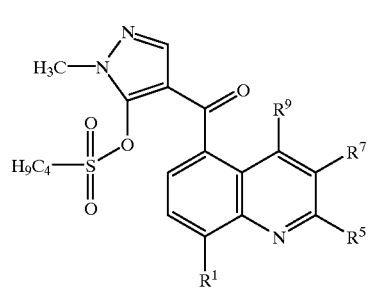

Ia27 the compounds Ia28.001–Ia28.211, which differ from the compounds Ia1.001–Ia1.211 in that $R^{14}$ is ethyl and $R^{15}$ is n-butylsulfonyl:

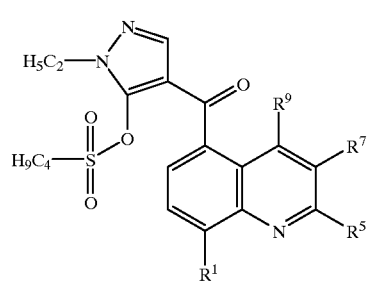

Ia28 the compounds Ia29.001–Ia29.211, which differ from the compounds Ia1.001–Ia1.211 in that $R^{15}$ is triofluoromethylsulfonyl:

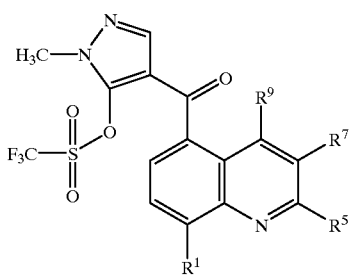

Ia29 the compounds Ia30.001–Ia30.211, which differ from the compounds Ia001–Ia211 in that $R^{14}$ is ethyl and $R^{15}$ is trifluoromethylsulfonyl:

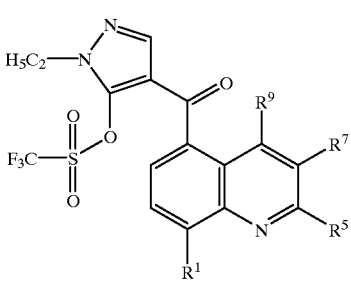

Ia30 the compounds Ia31.001–Ia31.211, which differ from the compounds Ia1.001–Ia1.211 in that $R^{15}$ is phenylsulfonyl:

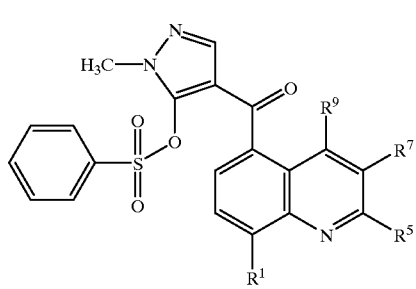

Ia31 the compounds Ia32.001–Ia32.211, which differ from the compounds Ia1.001–Ia1.211 in that $R^{14}$ is ethyl and $R^{15}$ is phenylsulfonyl:

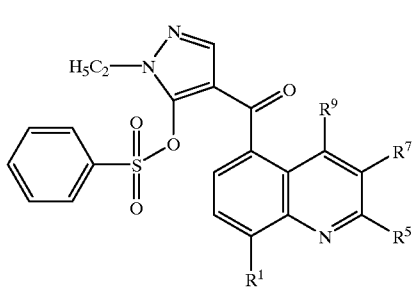

Ia32 the compounds Ia33.001–Ia33.211, which differ from the compounds Ia1.001–Ia1.211 in that $R^{15}$ is 4-methylphenylsulfonyl:

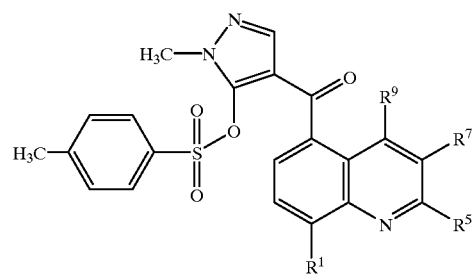

Ia33 the compounds Ia34.001–Ia34.211, which differ from the compounds Ia1.001–Ia1.211 in that $R^{14}$ is ethyl and $R^{15}$ is 4-methylphenylsulfonyl:

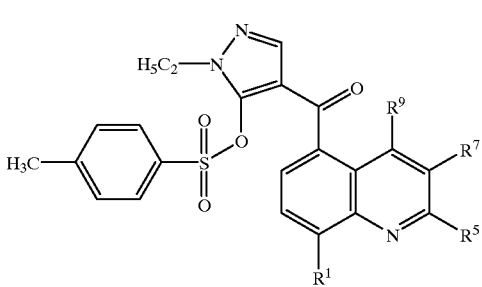

Ia34 the compounds Ia35.001–Ia35.211, which differ from the compounds Ia1.001–Ia1.211 in that $R^{16}$ is methyl:

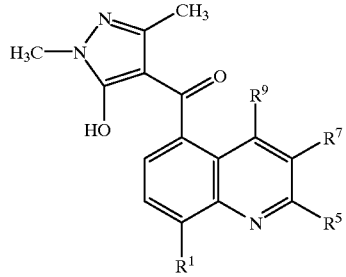

Ia35 the compounds Ia36.001–Ia36.211, which differ from the compounds Ia1.001–Ia1.211 in that $R^{14}$ is ethyl and $R^{16}$ is methyl:

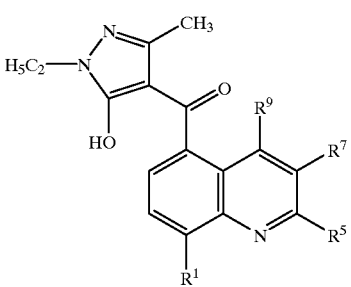

Ia36 the compounds Ia37.001–Ia37.211, which differ from the compounds Ia1.001–Ia1.211 in that $R^{15}$ and $R^{16}$ are each methyl:

Ia37

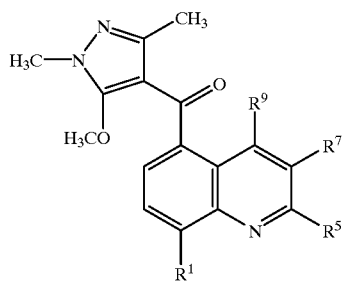

the compounds Ia38.001–Ia38.211, which differ from the compounds Ia1.001–Ia1.211 in that $R^{14}$ is ethyl and $R^{15}$ and $R^{16}$ are each methyl:

Ia38

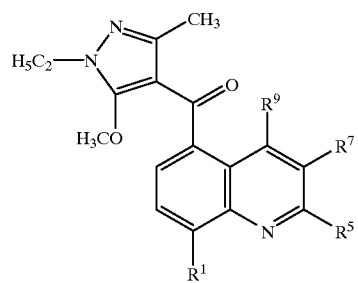

the compounds Ia39.001–Ia39.211, which differ from the compounds Ia1.001–Ia1.211 in that $R^{15}$ is ethyl and $R^{16}$ is methyl:

Ia39

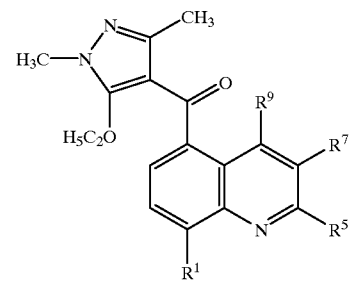

the compounds Ia40.001–Ia40.211, which differ from the compounds Ia1.001–Ia1.211 in that $R^{14}$ and $R^{15}$ are each ethyl and $R^{16}$ is methyl:

Ia40 the compounds Ia41.001–Ia41.211, which differ from the compounds Ia1.001–Ia1.211 in that $R^{15}$ is n-propyl and $R^{16}$ is methyl:

Ia41

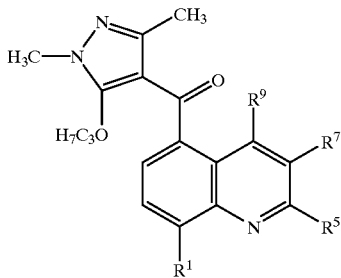

the compounds Ia42.001–Ia42.211, which differ from the compounds Ia001–Ia211 in that $R^{14}$ is ethyl, $R^{15}$ is n-propyl and $R^{16}$ is methyl:

Ia42

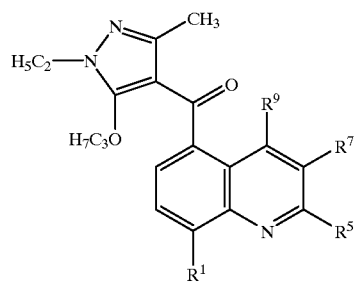

the compounds Ia43.001–Ia43.211, which differ from the compounds Ia1.001–Ia1.211 in that $R^{15}$ is n-butyl and $R^{16}$ is methyl:

Ia43

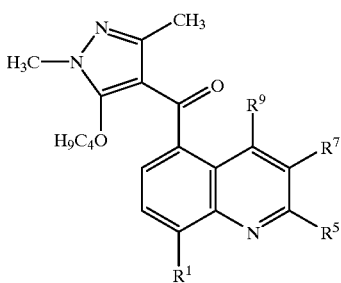

the compounds Ia44.001–Ia44.211, which differ from the compounds Ia1.001–Ia1.211 in that $R^{14}$ is ethyl, $R^{15}$ is n-butyl and $R^{16}$ is methyl:

Ia44

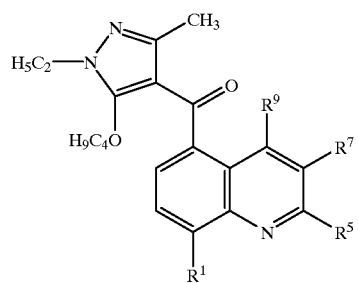

the compounds Ia45.001–Ia45.211, which differ from the compounds Ia1.001–Ia1.211 in that $R^{15}$ is methylcarbonyl and $R^{16}$ is methyl:

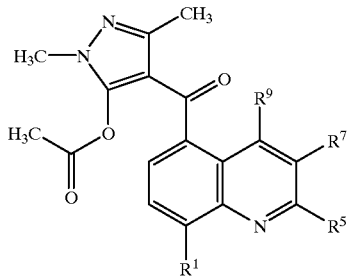

Ia45 the compounds Ia46.001–Ia46.211, which differ from the compounds Ia1.001–Ia1.211 in that $R^{14}$ is ethyl, $R^{15}$ is methylcarbonyl and $R^{16}$ is methyl:

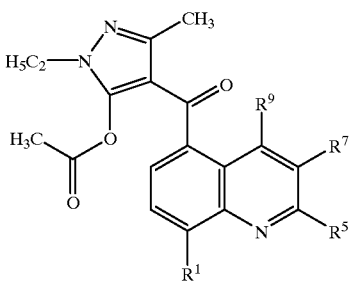

Ia46 the compounds Ia47.001–Ia47.211, which differ from the compounds Ia1.001–Ia1.211 in that $R^{15}$ is ethylcarbonyl and $R^{16}$ is methyl:

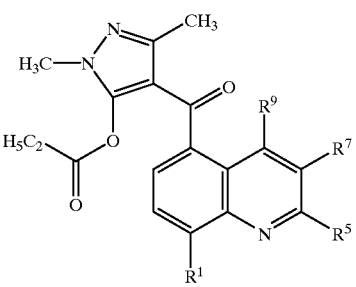

Ia47 the compounds Ia48.001–Ia48.211, which differ from the compounds Ia1.001–Ia1.211 in that $R^{14}$ is ethyl, $R^{15}$ is ethylcarbonyl and $R^{16}$ is methyl:

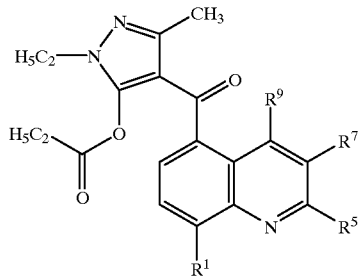

Ia48 the compounds Ia49.001–Ia49.211, which differ from the compounds Ia1.001–Ia1.211 in that $R^{15}$ is n-propylcarbonyl and $R^{16}$ is methyl:

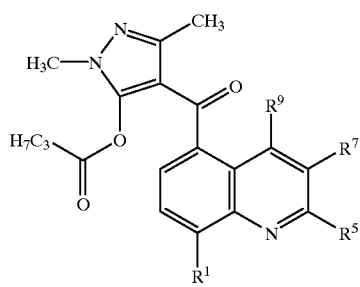

Ia49 the compounds Ia50.001–Ia50.211, which differ from the compounds Ia1.001–Ia1.211 in that $R^{14}$ is ethyl, $R^{15}$ is n-propylcarbonyl and $R^{16}$ is methyl:

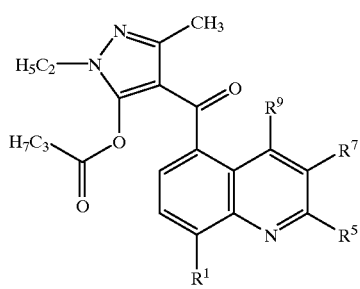

Ia50 the compounds Ia51.001–Ia51.211, which differ from the compounds Ia1.001–Ia1.211 in that $R^{15}$ is n-butylcarbonyl and $R^{16}$ is methyl:

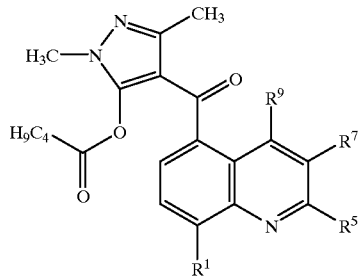

Ia51 the compounds Ia52.001–Ia52.211, which differ from the compounds Ia1.001–Ia1.211 in that $R^{14}$ is ethyl, $R^{15}$ is n-butylcarbonyl and $R^{16}$ is methyl:

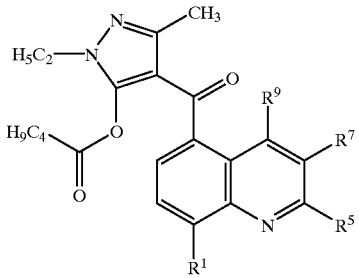

Ia52 the compounds Ia53.001–Ia53.211, which differ from the compounds Ia1.001–Ia1.211 in that $R^{15}$ is trifluoromethylcarbonyl and $R^{16}$ is methyl:

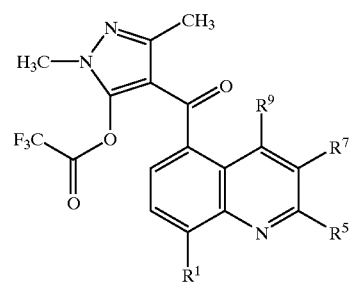

Ia53 the compounds Ia54.001–Ia54.211, which differ from the compounds Ia1.001–Ia1.211 in that $R^{14}$ is ethyl, $R^{15}$ is trifluoromethylcarbonyl and $R^{16}$ is methyl:

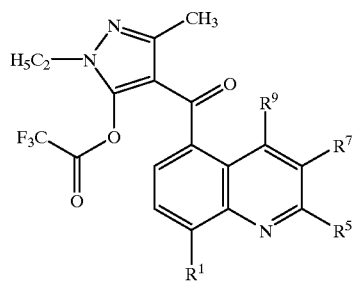

Ia54 the compounds Ia55.001–Ia55.211, which differ from the compounds Ia1.001–Ia1.211 in that $R^{15}$ is methylsulfonyl and $R^{16}$ is methyl:

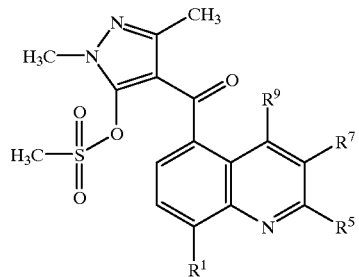

Ia55 the compounds Ia56.001–Ia56.211, which differ from the compounds Ia1.001–Ia1.211 in that $R^{14}$ is ethyl, $R^{15}$ is methylsulfonyl and $R^{16}$ is methyl:

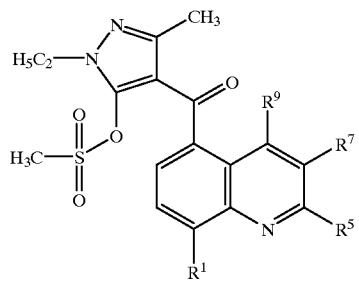

Ia56 the compounds Ia57.001–Ia57.211, which differ from the compounds Ia1.001–Ia1.211 in that $R^{15}$ is ethylsulfonyl and $R^{16}$ is methyl:

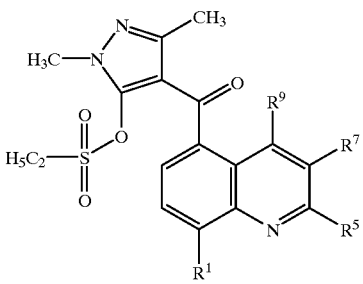

Ia57 the compounds Ia58.001–Ia58.211, which differ from the compounds Ia1.001–Ia1.211 in that $R^{14}$ is ethyl, $R^{15}$ is ethylsulfonyl and $R^{16}$ is methyl:

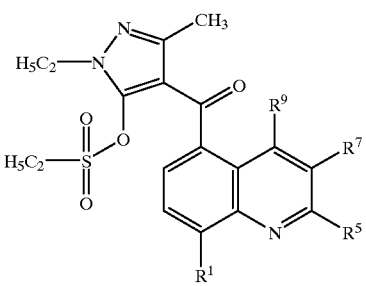

Ia58 the compounds Ia59.01–Ia59.211, which differ from the compounds Ia1.001–Ia1.211 in that $R^{15}$ is n-propylsulfonyl and $R^{16}$ is methyl:

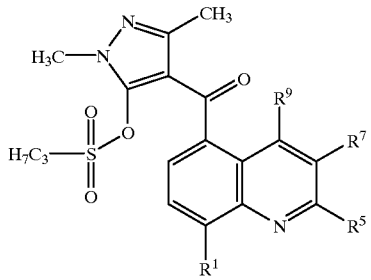

Ia59 the compounds Ia60.001–Ia60.211, which differ from the compounds Ia1.001–Ia1.211 in that $R^{14}$ is ethyl, $R^{15}$ is n-propylsulfonyl and $R^{16}$ is methyl:

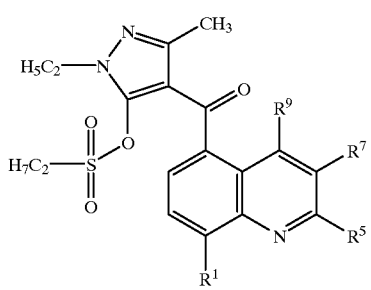

Ia60 the compounds Ia61.001–Ia61.211, which differ from the compounds Ia1.001–Ia1.211 in that $R^{15}$ is n-butylsulfonyl and $R^{16}$ is methyl:

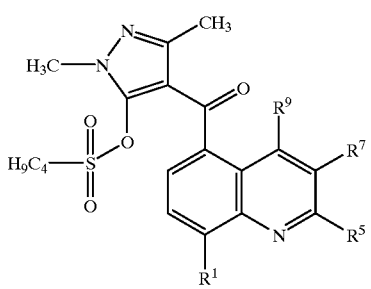

Ia61 the compounds Ia62.001–Ia62.211, which differ from the compounds Ia1.001–Ia1.211 in that $R^{14}$ is ethyl, $R^{15}$ is n-butylsulfonyl and $R^{16}$ is methyl:

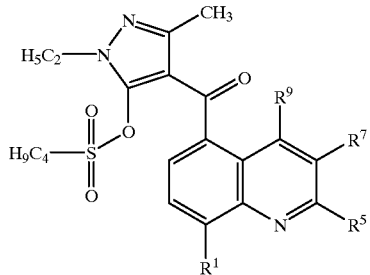

Ia62 the compounds Ia63.001–Ia63.211, which differ from the compounds Ia1.001–Ia1.211 in that $R^{15}$ is trifluoromethylsulfonyl and $R^{16}$ is methyl:

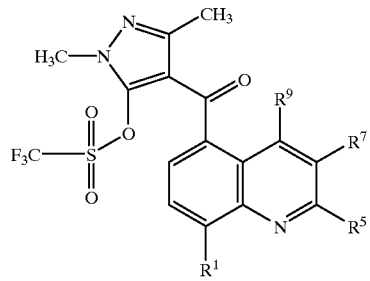

Ia63 the compounds Ia64.001–Ia64.211, which differ from the compounds Ia1.001–Ia1.211 in that $R^{14}$ is ethyl, $R^{15}$ is trifluoromethylsulfonyl and $R^{16}$ is methyl:

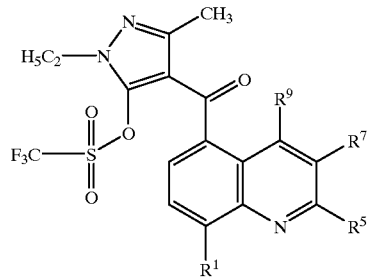

Ia64 the compounds Ia65.001–Ia65.211, which differ from the compounds Ia1.001–Ia1.211 in that $R^{15}$ is phenylsulfonyl and $R^{16}$ is methyl:

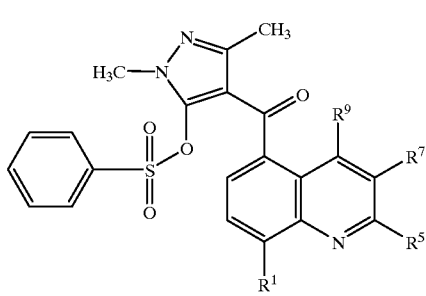

Ia65 the compounds Ia66.001–Ia66.211, which differ from the compounds Ia1.001–Ia1.211 in that $R^{14}$ is ethyl, $R^{15}$ is phenylsulfonyl and $R^{16}$ is methyl:

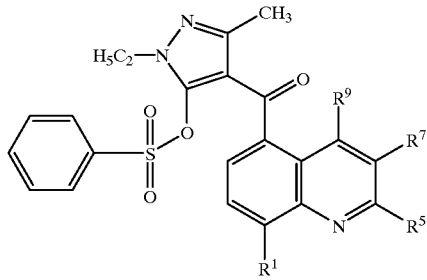

Ia66 the compounds Ia67.001–Ia67.211, which differ from the compounds Ia1.001–Ia1.211 in that $R^{15}$ is 4-methylphenylsulfonyl and $R^{16}$ is methyl:

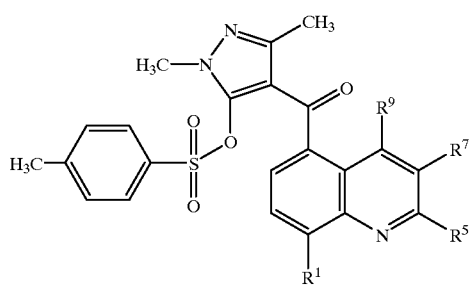

Ia67 the compounds Ia68.001–Ia68.211, which differ from the compounds Ia1.001–Ia1.211 in that $R^{14}$ is ethyl, $R^{15}$ is 4-methylphenylsulfonyl and $R^{16}$ is methyl:

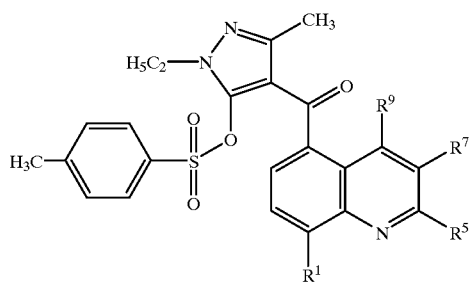

Ia68 the compounds Ia'1-001–Ia'1.211, which differ from the compounds Ia1.001–Ia1.211 in that they are the N-oxides (z=$Z^{11}$):

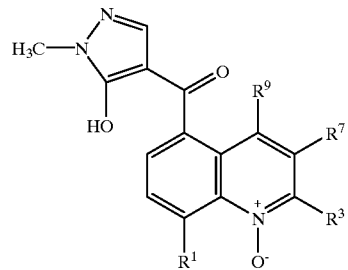

Ia'1 the compounds Ia'2-001–Ia'2.211, which differ from the compounds Ia1.001–Ia1.211 in that $R^{14}$ is ethyl and in that they are the N-oxides (Z=$Z^{11}$):

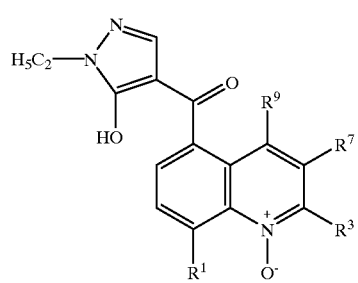

Ia'2 the compounds Ia'3.001–Ia'3.211, which differ from the compounds Ia1.001–Ia1.211 in that $R^{15}$ is methyl and in that they are the N-oxides (Z=$Z^{11}$):

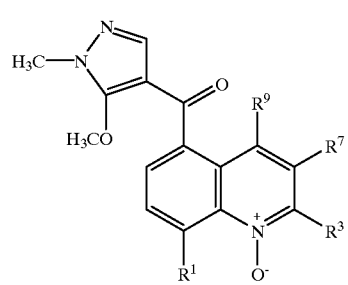

Ia'3 the compounds Ia'4.001–Ia'4.211, which differ from the compounds Ia1.001–Ia1.211 in that $R^{14}$ is ethyl and $R^{15}$ is methyl and in that they are the N-oxides (Z=$Z^{11}$):

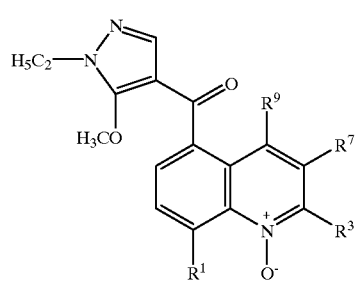

Ia'4 the compounds Ia'5.001–Ia'5.211, which differ from the compounds Ia1.001–Ia1.211 in that $R^{15}$ is ethyl and in that they are the N-oxides ($Z=Z^{11}$):

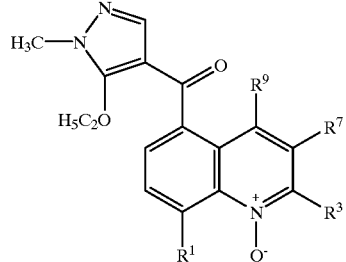

Ia'5 the compounds Ia'6.001–Ia'6.211, which differ from the compounds Ia1.001–Ia1.211 in that $R^{14}$ and $R^{15}$ are each ethyl and in that they are the N-oxides ($Z=Z^{11}$):

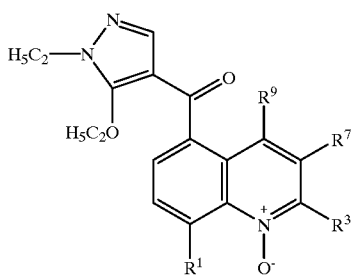

Ia'6 the compounds Ia'7.001–Ia'7.211, which differ from the compounds Ia1.001–Ia1.211 in that $R^{15}$ is n-propyl and in that they are the N-oxides ($Z=Z^{11}$):

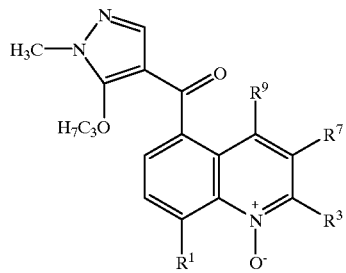

Ia'7 the compounds Ia'8.001–Ia'8.211, which differ from the compounds Ia1.001–Ia1.211 in that $R^{14}$ is ethyl and $R^{15}$ is n-propyl and in that they are the N-oxides ($Z=Z^{11}$):

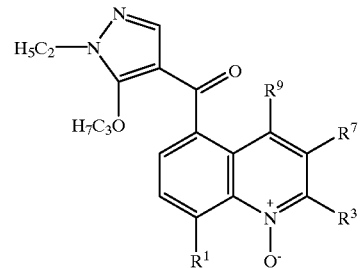

Ia'8 the compounds Ia'9.001–Ia'9.211, which differ from the compounds Ia1.001–Ia1.211 in that $R^{15}$ is n-butyl and in that they are the N-oxides ($Z=Z^{11}$):

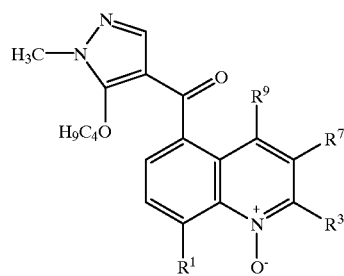

Ia'9 the compounds Ia'10.001–Ia'10.211, which differ from the compounds Ia1.001–Ia1.211 in that $R^{14}$ is ethyl and $R^{15}$ is n-butyl and in that they are the N-oxides ($Z=Z^{11}$):

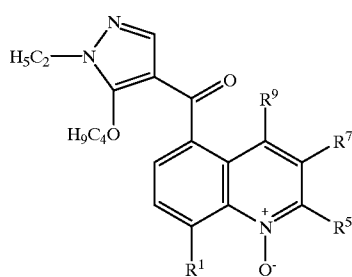

Ia'10 the compounds Ia'11.001–Ia'11.211, which differ from the compounds Ia1.001–Ia1.211 in that $R^{15}$ is methylcarbonyl and in that they are the N-oxides ($Z=Z^{11}$):

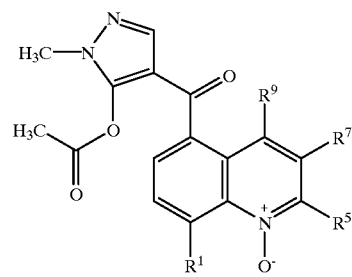

Ia'11 the compounds Ia'12.001–Ia'12.211, which differ from the compounds Ia1.001–Ia1.211 in that $R^{14}$ is ethyl and $R^{15}$ is methylcarbonyl and in that they are the N-oxides ($Z=Z^{11}$):

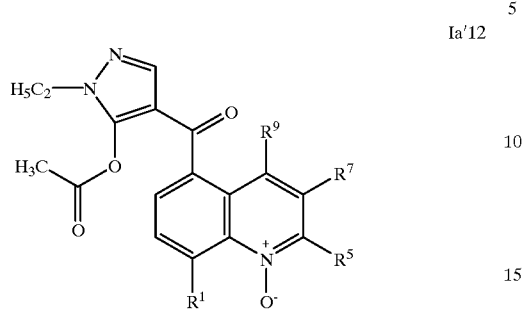

Ia'12 the compounds Ia'13.001–Ia'13.211, which differ from the compounds Ia1.001–Ia1.211 in that $R^{15}$ is ethylcarbonyl and in that they are the N-oxides ($Z=Z^{11}$):

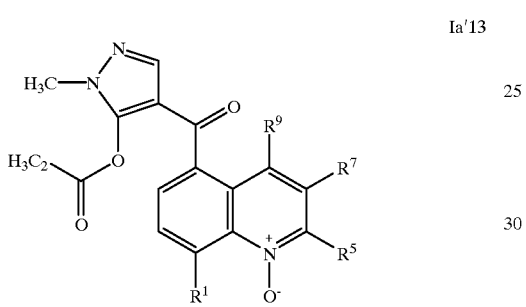

Ia'13 the compounds Ia'14.001–Ia'14.211, which differ from the compounds Ia1.001–Ia1.211 in that $R^{14}$ is ethyl and $R^{15}$ is ethylcarbonyl and in that they are the N-oxides ($Z=Z^{11}$):

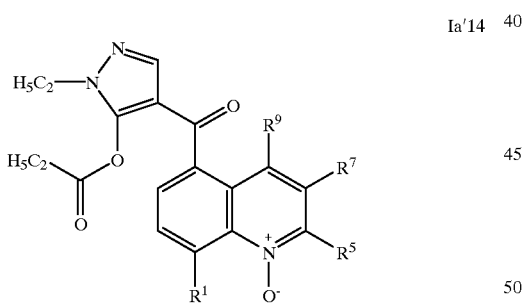

Ia'14 the compounds Ia'15.001–Ia'15.211, which differ from the compounds Ia1.001–Ia1.211 in that $R^{15}$ is n-propylcarbonyl and in that they are the N-oxides ($Z=Z^{11}$):

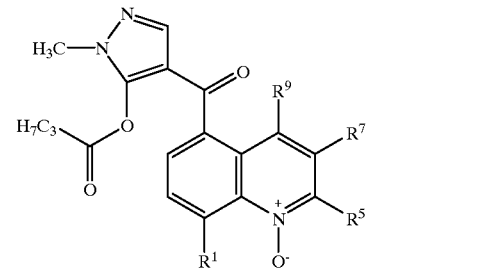

Ia'15 the compounds Ia'16.001–Ia'16.211, which differ from the compounds Ia1.001–Ia1.211 in that $R^{14}$ is ethyl and $R^{15}$ is n-propylcarbonyl and in that they are the N-oxides ($Z=Z^{11}$):

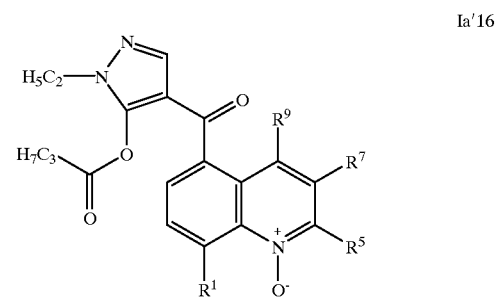

Ia'16 the compounds Ia'17.001–Ia'17.211, which differ from the compounds Ia1.001–Ia1.211 in that $R^{15}$ is n-butylcarbonyl and in that they are the N-oxides ($Z=Z^{11}$):

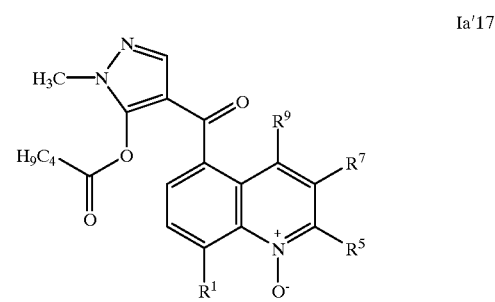

Ia'17 the compounds Ia'18.001–Ia'18.211, which differ from the compounds Ia1.001–Ia1.211 in that $R^{14}$ is ethyl and $R^{15}$ is n-butylcarbonyl and in that they are the N-oxides ($Z=Z^{11}$):

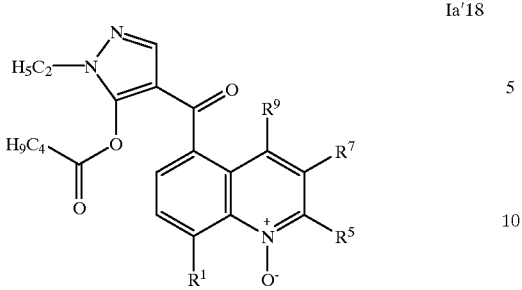

Ia'18 the compounds Ia'19.001–Ia'19.211, which differ from the compounds Ia1.001–Ia1.211 in that $R^{15}$ is trifluoromethylcarbonyl and in that they are the N-oxides ($Z=Z^{11}$):

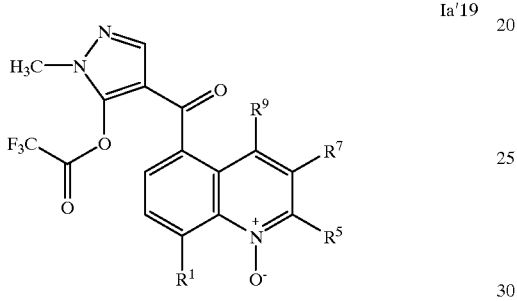

Ia'19 the compounds Ia'20.001–Ia'20.211, which differ from the compounds Ia1.001–Ia1.211 in that $R^{14}$ is ethyl and $R^{15}$ is trifluoromethylcarbonyl and in that they are the N-oxides ($Z=Z^{11}$):

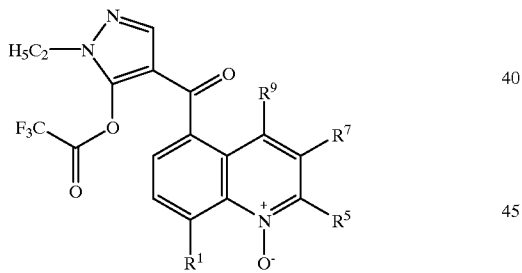

Ia'20 the compounds Ia'21.001–Ia'21.211, which differ from the compounds Ia1.001–Ia1.211 in that $R^{15}$ is methylsulfonyl and in that they are the N-oxides ($Z=Z^{11}$):

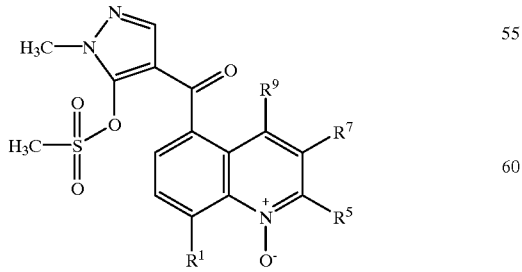

Ia'21 the compounds Ia'22.001–Ia'22.211, which differ from the compounds Ia1.001–Ia1.211 in that $R^{14}$ is ethyl and $R^{15}$ is methylsulfonyl and in that they are the N-oxides ($Z=Z^{11}$):

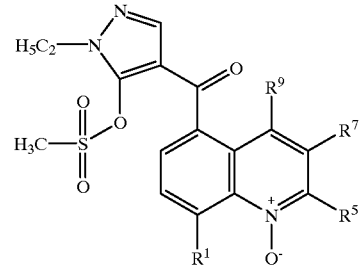

Ia'22 the compounds Ia'23.001–Ia'23.211, which differ from the compounds Ia1.001–Ia1.211 in that $R^{15}$ is ethylsulfonyl and in that they are the N-oxides ($Z=Z^{11}$):

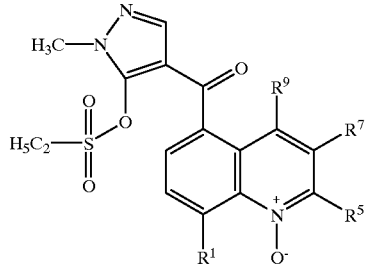

Ia'23 the compounds Ia'24.001–Ia'24.211, which differ from the compounds Ia1.001–Ia1.211 in that $R^{14}$ is ethyl and $R^{15}$ is ethylsulfonyl and in that they are the N-oxides ($Z=Z^{11}$):

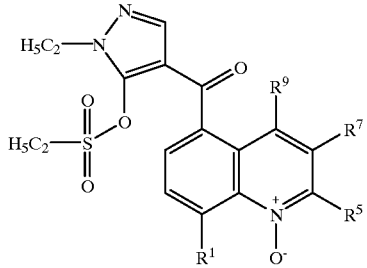

Ia'24 the compounds Ia'25.001–Ia'25.211, which differ from the compounds Ia1.001–Ia1.211 in that $R^{15}$ is n-propylsulfonyl and in that they are the N-oxides ($Z=Z^{11}$):

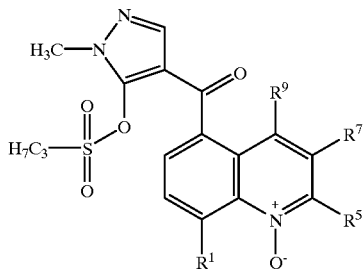

Ia'25 the compounds Ia'26.001–Ia'26.211, which differ from the compounds Ia1.001–Ia1.211 in that $R^{14}$ is ethyl and $R^{15}$ is n-propylsulfonyl and in that they are the N-oxides $(Z=Z^{11})$:

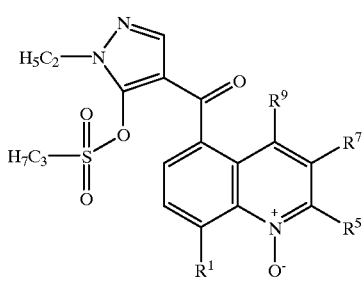

Ia'26 the compounds Ia'27.001–Ia'27.211, which differ from the compounds Ia1.001–Ia1.211 in that $R^{15}$ is n-butylsulfonyl and in that they are the N-oxides $(Z=Z^{11})$:

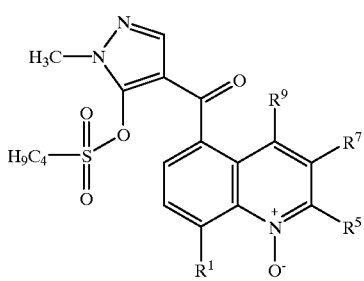

Ia'27 the compounds Ia'28.001–Ia'28.211, which differ from the compounds Ia1.001–Ia1.211 in that $R^{14}$ is ethyl and $R^{15}$ is n-butylsulfonyl and in that they are the N-oxides $(Z=Z^{11})$:

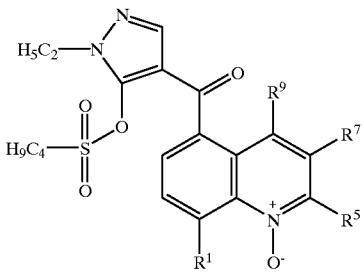

Ia'28 the compounds Ia'29.001–Ia'29.211, which differ from the compounds Ia1.001–Ia1.211 in that $R^{15}$ is trifluoromethylsulfonyl and in that they are the N-oxides $(Z=Z^{11})$:

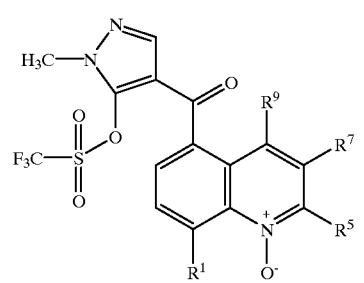

Ia'29 the compounds Ia'30.001–Ia'30.211, which differ from the compounds Ia1.001–Ia1.211 in that $R^{14}$ is ethyl and $R^{15}$ is trifluoromethylsulfonyl and in that they are the N-oxides $(Z=Z^{11})$:

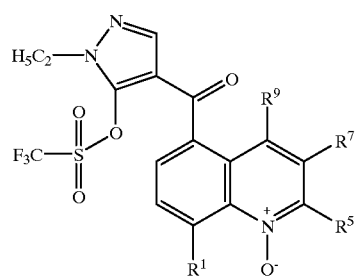

Ia'30 the compounds Ia'31.001–Ia'31.211, which differ from the compounds Ia1.001–Ia1.211 in that $R^{15}$ is phenylsulfonyl and in that they are the N-oxides $(Z=Z^{11})$:

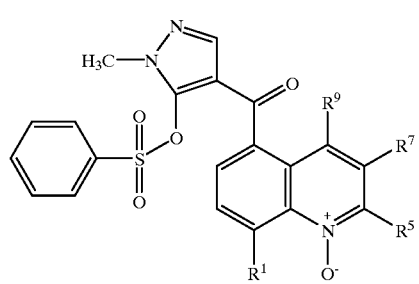

Ia'31 the compounds Ia'32.001–Ia'32.211, which differ from the compounds Ia1.001–Ia1.211 in that $R^{14}$ is ethyl and $R^{15}$ is phenylsulfonyl and in that they are the N-oxides ($Z=Z^{11}$):

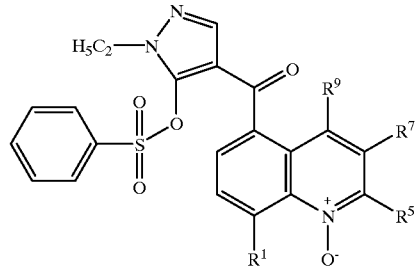

Ia'32 the compounds Ia'33.001–Ia'33.211, which differ from the compounds Ia1.001–Ia1.211 in that $R^{15}$ is 4-methylphenylsulfonyl and in that they are the N-oxides ($Z=Z^{11}$):

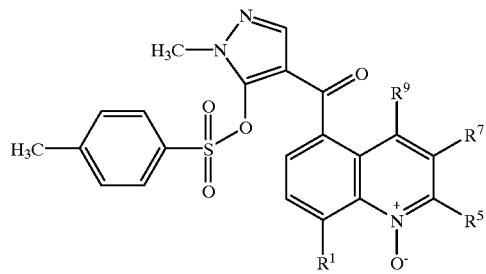

Ia'33 the compounds Ia'34.001–Ia'34.211, which differ from the compounds Ia1.001–Ia1.211 in that $R^{14}$ is ethyl and $R^{15}$ is 4-methylphenylsulfonyl and in that they are the N-oxides ($Z=Z^{11}$):

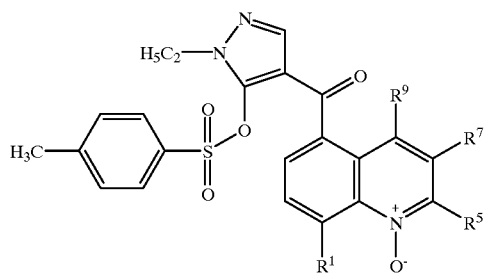

Ia'34 the compounds Ia'35.001–Ia'35.211, which differ from the compounds Ia1.001–Ia1.211 in that $R^{16}$ is methyl and in that they are the N-oxides ($Z=Z^{11}$):

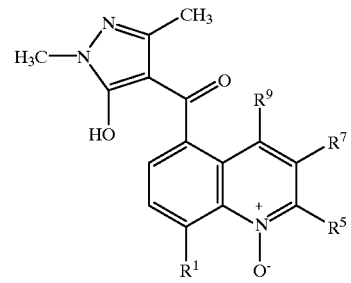

Ia'35 the compounds Ia'36.001–Ia'36.211, which differ from the compounds Ia1.001–Ia1.211 in that $R^{14}$ is ethyl and $R^{16}$ is methyl and in that they are the N-oxides ($Z=Z^{11}$):

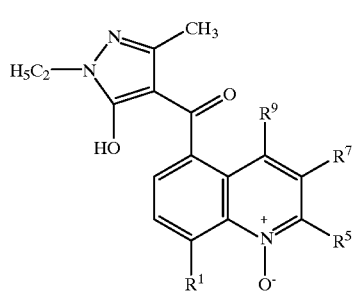

Ia'36 the compounds Ia'37.001–Ia'37.211, which differ from the compounds Ia1.001–Ia1.211 in that $R^{15}$ and $R^{16}$ are each methyl and in that they are the N-oxides ($Z=Z^{11}$):

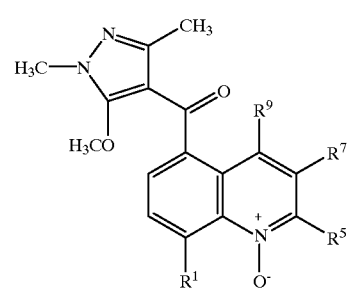

Ia'37 the compounds Ia'38.001–Ia'38.211, which differ from the compounds Ia1.001–Ia1.211 in that $R^{14}$ is ethyl, $R^{15}$ and $R^{16}$ are each methyl and in that they are the N-oxides ($Z=Z^{11}$):

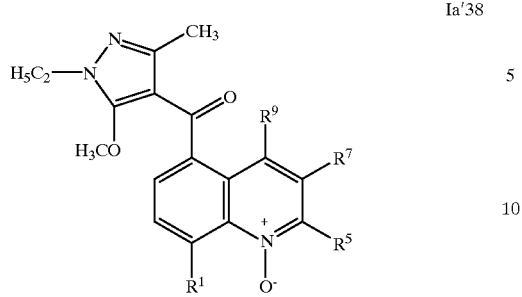

Ia'38 the compounds Ia'39.001–Ia'39.211, which differ from the compounds Ia1.001–Ia1.211 in that $R^{15}$ is ethyl and $R^{16}$ is methyl and in that they are the N-oxides ($Z=Z^{11}$)

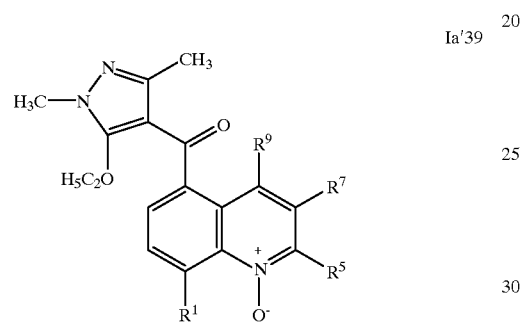

Ia'39 the compounds Ia'40.001–Ia'40.211, which differ from the compounds Ia1.001–Ia1.211 in that $R^{14}$ and $R^{15}$ are each ethyl and $R^{16}$ is methyl and in that they are the N-oxides ($Z=Z^{11}$):

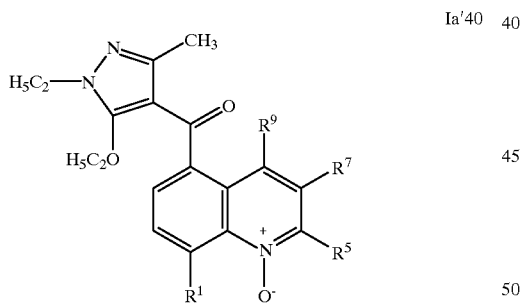

Ia'40 the compounds Ia'41.001–Ia'41.211, which differ from the compounds Ia1.001–Ia1.211 in that $R^{15}$ is n-propyl and $R^{16}$ is methyl and in that they are the N-oxides ($Z=Z^{11}$):

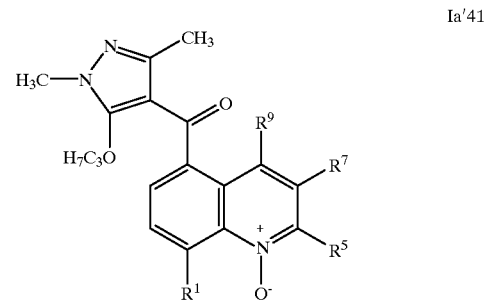

Ia'41 the compounds Ia'42.001–Ia'42.211, which differ from the compounds Ia1.001–Ia1.211 in that $R^{14}$ is ethyl, $R^{15}$ is n-propyl and $R^{16}$ is methyl and in that they are the N-oxides ($Z=Z^{11}$):

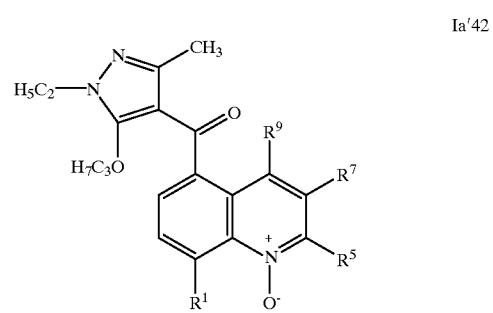

Ia'42 the compounds Ia'43.001–Ia'43.211, which differ from the compounds Ia1.001-Ia1.211 in that $R^{15}$ is n-butyl and $R^{16}$ is methyl and in that they are the N-oxides ($Z=Z^{11}$):

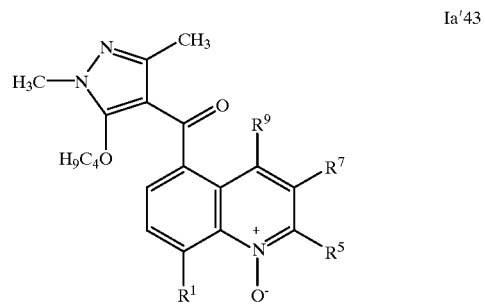

Ia'43 the compounds Ia'44.001–Ia'44.211, which differ from the compounds Ia1.001–Ia1.211 in that $R^{14}$ is ethyl, $R^{15}$ is n-butyl and $R^{16}$ is methyl and in that they are the N-oxides ($Z=Z^{11}$):

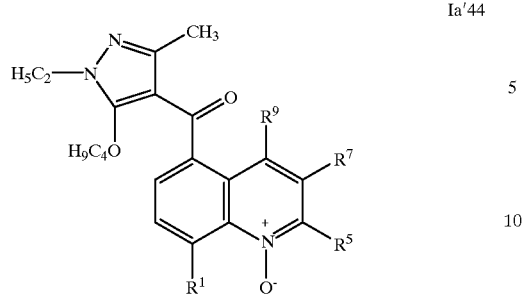

Ia'44

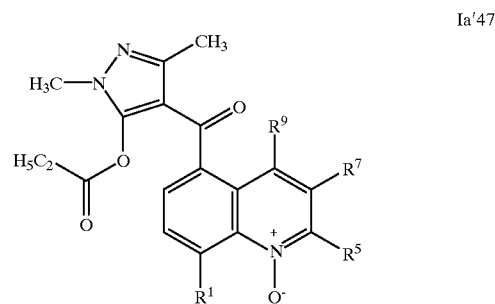

Ia'47 the compounds Ia'45.001–Ia'45.211, which differ from the compounds Ia1.001–Ia1.211 in that $R^{15}$ is methylcarbonyl and $R^{16}$ is methyl and in that they are the N-oxides ($z=Z^{11}$):

the compounds Ia'48.001–Ia'48.211, which differ from the compounds Ia1.001–Ia1.211 in that $R^{14}$ is ethyl, $R^{15}$ is ethylcarbonyl and $R^{16}$ is methyl and in that they are the N-oxides ($Z=Z^{11}$):

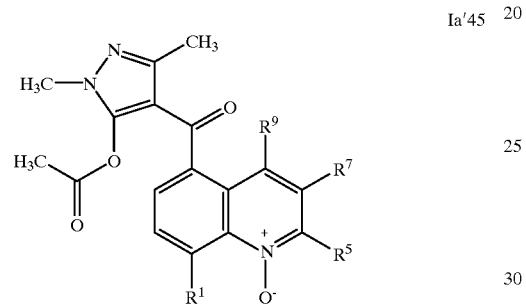

Ia'45

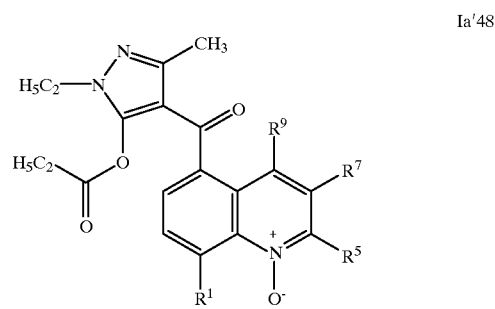

Ia'48 the compounds Ia'46.001–Ia'46.2111, which differ from the compounds Ia1.001–Ia1.211 in that $R^{14}$ is ethyl, $R^{15}$ is methylcarbonyl and $R^{16}$ is methyl and in that they are the N-oxides ($Z=Z^{11}$):

the compounds Ia'49.001–Ia'49.211, which differ from the compounds Ia1.001–Ia1.211 in that $R^{15}$ is n-propylcarbonyl and $R^{16}$ is methyl and in that they are the N-oxides ($Z=Z^{11}$):

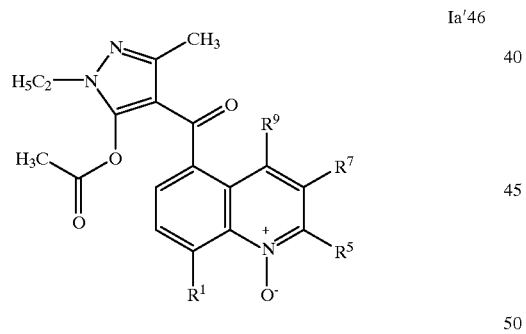

Ia'46

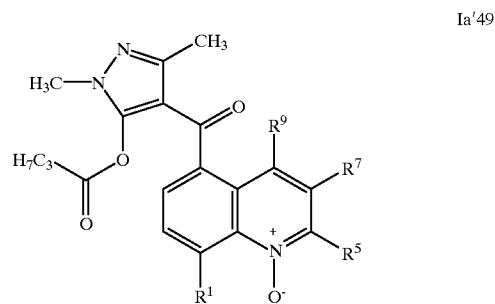

Ia'49 the compounds Ia'47.001–Ia'47.211, which differ from the compounds Ia1.001–Ia1.211 in that $R^{15}$ is ethylcarbonyl and $R^{16}$ is methyl and in that they are the N-oxides ($Z=Z^{11}$):

the compounds Ia'50.001–Ia'50.211, which differ from the compounds Ia1.001–Ia1.211 in that $R^{14}$ is ethyl, $R^{15}$ is n-propylcarbonyl and $R^{16}$ is methyl and in that they are the N-oxides ($Z=Z^{11}$):

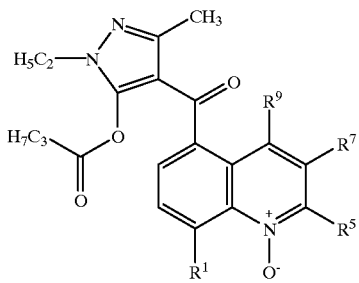

Ia'50 the compounds Ia'51.001–Ia'51.211, which differ from the compounds Ia1.001–Ia1.211 in that $R^{15}$ is n-butylcarbonyl and $R^{16}$ is methyl and in that they are the N-oxides (Z=$Z^{11}$):

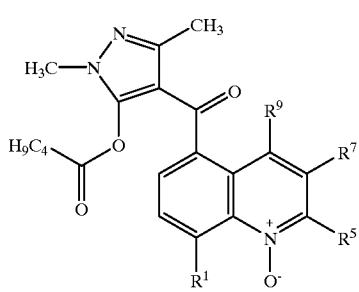

Ia'51 the compounds Ia'52.001–Ia'52.211, which differ from the compounds Ia1.001–Ia1.211 in that $R^{14}$ is ethyl, $R^{15}$ is n-butylcarbonyl and $R^{16}$ is methyl and in that they are the N-oxides (Z=$Z^{11}$):

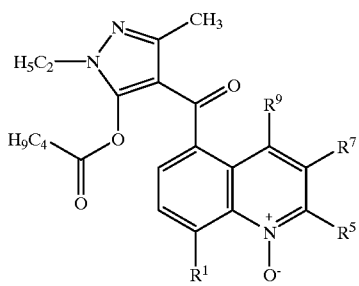

Ia'52 the compounds Ia'53.001–Ia'53.211, which differ from the compounds Ia001–Ia211 in that $R^{15}$ is trifluoromethylcarbonyl and $R^{16}$ is methyl and in that they are the N-oxides (Z=$Z^{11}$):

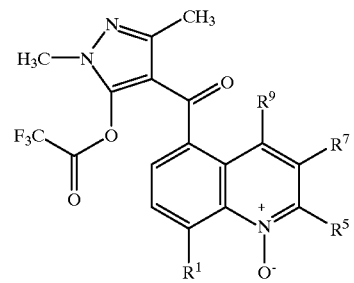

Ia'53 the compounds Ia'54.001–Ia'54.211, which differ from the compounds Ia1.001–Ia211 in that $R^{14}$ is ethyl, $R^{15}$ is trifluoromethylcarbonyl and $R^{16}$ is methyl and in that they are the N-oxides (Z=$Z^{11}$):

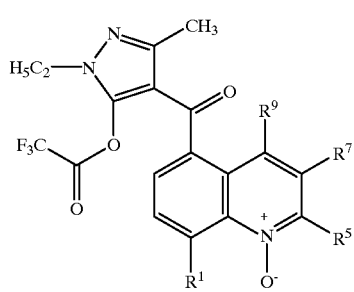

Ia'54 the compounds Ia'55.001–Ia'55.211, which differ from the compounds Ia1.001–Ia1.211 in that $R^{15}$ is methylsulfonyl and $R^{16}$ is methyl and in that they are the N-oxides (Z=$Z^{11}$):

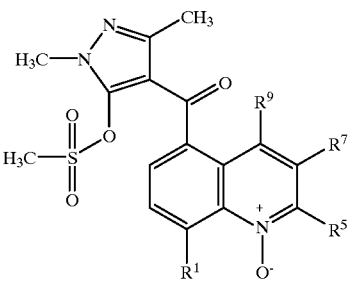

Ia'55 the compounds Ia'56.001–Ia'56.211, which differ from the compounds Ia1.001–Ia1.211 in that $R^{14}$ is ethyl, $R^{15}$ is methylsulfonyl and $R^{16}$ is methyl and in that they are the N-oxides (Z=$Z^{11}$):

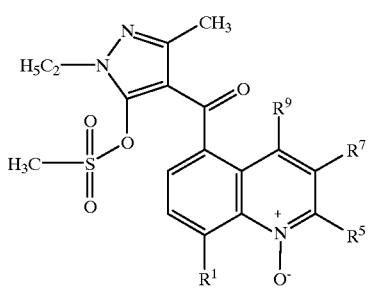

Ia′56 the compounds Ia′57.001–Ia′57.211, which differ from the compounds Ia1.001–Ia1.211 in that $R^{15}$ is ethylsulfonyl and $R^{16}$ is methyl and in that they are the N-oxides $(Z=Z^{11})$:

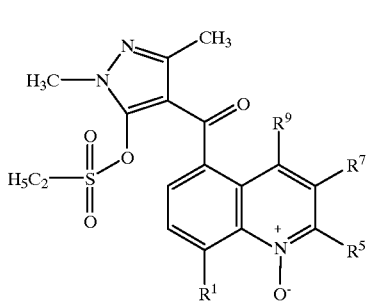

Ia′57 the compounds Ia′58.001–Ia′58.211, which differ from the compounds Ia1.001–Ia1.211 in that $R^{14}$ is ethyl, $R^{15}$ is ethylsulfonyl and $R^{16}$ is methyl and in that they are the N-oxides $(Z=Z^{11})$:

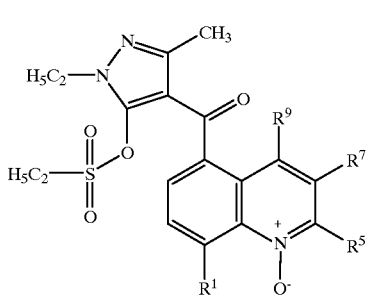

Ia′58 the compounds Ia′59.001–Ia′59.211, which differ from the compounds Ia1.001–Ia1.211 in that $R^{15}$ is n-propylsulfonyl and $R^{16}$ is methyl and in that they are the N-oxides $(Z=Z^{11})$:

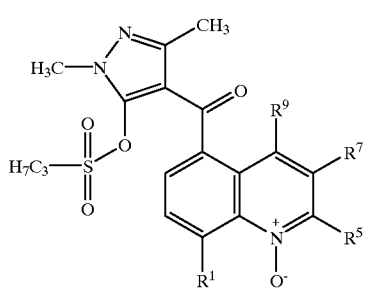

Ia′59 the compounds Ia′60.001–Ia′60.211, which differ from the compounds Ia1.001–Ia1.211 in that $R^{14}$ is ethyl, $R^{15}$ is n-propylsulfonyl and $R^{16}$ is methyl and in that they are the N-oxides $(Z=Z^{11})$:

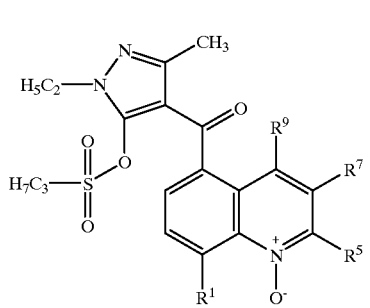

Ia′60 the compounds Ia′61.001–Ia′61.211, which differ from the compounds Ia1.001–Ia1.211 in that $R^{15}$ is n-butylsulfonyl and $R^{16}$ is methyl and in that they are the N-oxides $(Z=Z^{11})$:

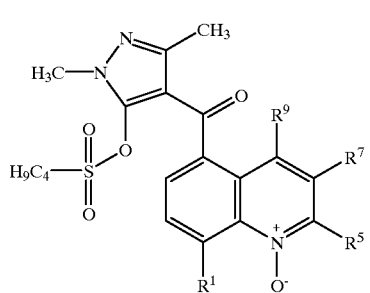

Ia′61 the compounds Ia′62.001–Ia′62.211, which differ from the compounds Ia1.001–Ia1.211 in that $R^{14}$ is ethyl, $R^{15}$ is n-butylsulfonyl and $R^{16}$ is methyl and in that they are the N-oxides $(Z=Z^{11})$:

Ia'62

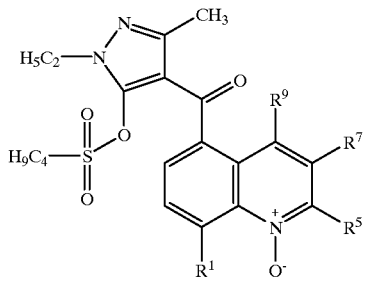

the compounds Ia'63.001–Ia'63.211, which differ from the compounds Ia1.001–Ia1.211 in that $R^{15}$ is trifluoromethylsulfonyl and $R^{16}$ is methyl and in that they are the N-oxides ($Z=Z^{11}$):

Ia'63

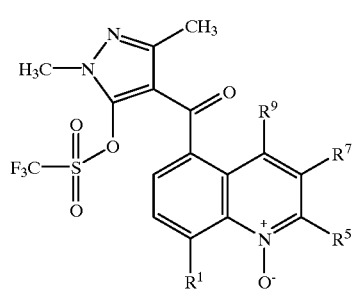

the compounds Ia'64.001–Ia'64.211, which differ from the compounds Ia1.001–Ia1.211 in that $R^{14}$ is ethyl, $R^{15}$ is trifluoromethylsulfonyl and $R^{16}$ is methyl and in that they are the N-oxides ($Z=Z^{11}$):

Ia'64

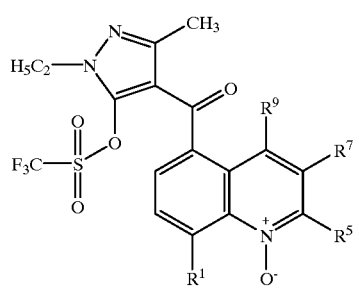

the compounds Ia'65.001–Ia'65.211, which differ from the compounds Ia1.001–Ia1.211 in that $R^{15}$ is phenylsulfonyl and $R^{16}$ is methyl and in that they are the N-oxides ($Z=Z^{11}$):

Ia'65

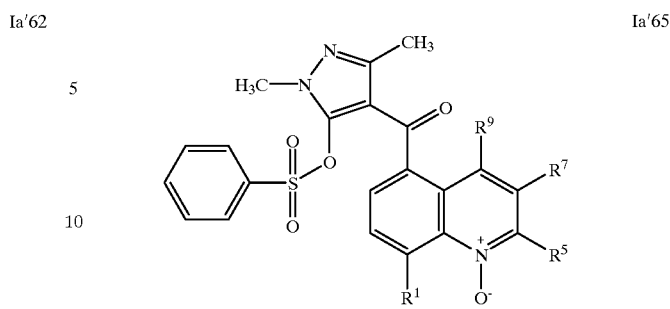

the compounds Ia'66.001–Ia'66.211, which differ from the compounds Ia1.001–Ia1.211 in that $R^{14}$ is ethyl, $R^{15}$ is phenylsulfonyl and $R^{16}$ is methyl and in that they are the N-oxides ($Z=Z^{11}$):

Ia'66

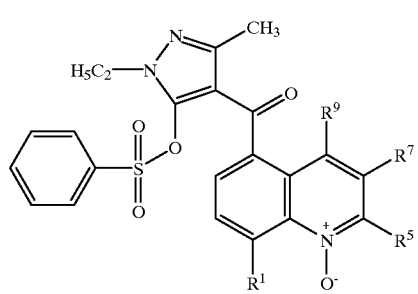

the compounds Ia'67.001–Ia'67.211, which differ from the compounds Ia1.001–Ia1.211 in that $R^{15}$ is 4-methylphenylsulfonyl and $R^{16}$ is methyl and in that they are the N-oxides ($Z=Z^{11}$):

Ia'67

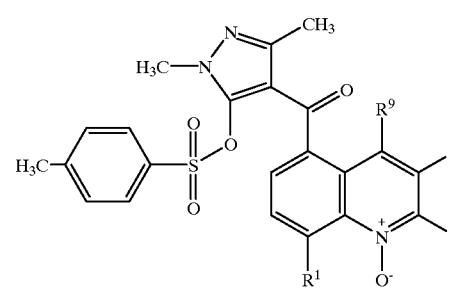

the compounds Ia'68.001–Ia'68.211, which differ from the compounds Ia1.001–Ia1.211 in that $R^{14}$ is ethyl, $R^{15}$ is 4-methylphenylsulfonyl and $R^{16}$ is methyl and in that they are the N-oxides ($Z=Z^{11}$):

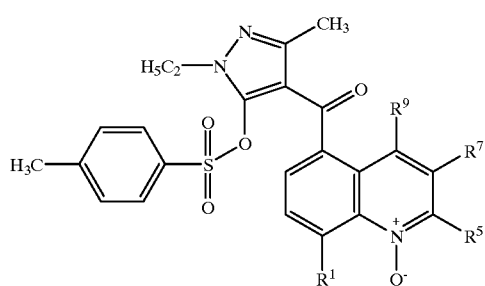

Ia'68

Likewise, very particular preference is given to the compounds Ib1(= I where $R^{14}$ $CH_3$ and $R^{15}$=H and where the "Q—CO— fragment" is attached in position e, RI is attached in position d, $R^2$ is attached in position a and $Z^1$ is attached in positions b and c) listed in Table 2 below.

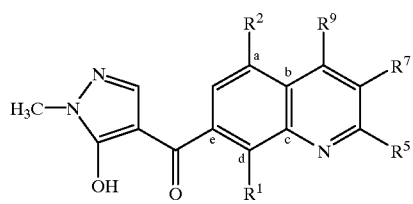

Ib1

TABLE 2

| No. | $R^1$ | $R^2$ | $R^5$ | $R^7$ | $R^9$ |
|---|---|---|---|---|---|
| Ib1.01 | $CH_3$ | H | H | H | H |
| Ib1.02 | $CH_3$ | H | H | H | $CH_3$ |
| Ib1.03 | $CH_3$ | H | H | $CH_3$ | H |
| Ib1.04 | $CH_3$ | H | $CH_3$ | H | H |
| Ib1.05 | $CH_3$ | $CH_3$ | H | H | H |
| Ib1.06 | $CH_3$ | H | H | H | Cl |
| Ib1.07 | $CH_3$ | H | H | Cl | H |
| Ib1.08 | $CH_3$ | H | Cl | H | H |
| Ib1.09 | $CH_3$ | Cl | H | H | H |
| Ib1.10 | $CH_3$ | H | H | H | $CF_3$ |
| Ib1.11 | $CH_3$ | H | H | $CF_3$ | H |
| Ib1.12 | $CH_3$ | H | $CF_3$ | H | H |
| Ib1.13 | Cl | H | H | H | H |
| Ib1.14 | Cl | H | H | H | $CH_3$ |
| Ib1.15 | Cl | H | H | $CH_3$ | H |
| Ib1.16 | Cl | H | $CH_3$ | H | H |
| Ib1.17 | Cl | H | H | H | Cl |
| Ib1.18 | Cl | H | H | Cl | H |
| Ib1.19 | Cl | H | Cl | H | H |
| Ib1.20 | Cl | H | Cl | Cl | Cl |
| Ib1.21 | $CH_3$ | H | $CH_3$ | $CH_3$ | $CH_3$ |

Furthermore, very particular preference is given to the following hetaroyl derivatives of the formula I:

the compounds Ib2.01–Ib2.21, which differ from the corresponding compounds Ib1.01–Ib1.21 in that $R^{14}$ is ethyl:

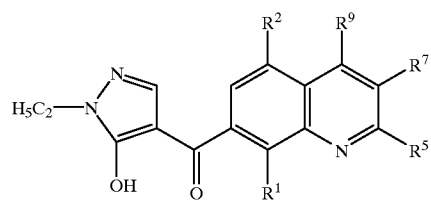

Ib2 the compounds Ib3.01–Ib3.21 which differ from the corresponding compounds Ib1.01–Ib1.21 in that $R^{15}$ is methyl:

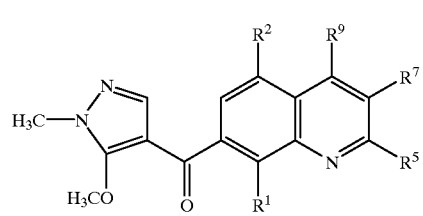

Ib3 the compounds Ib4.01–Ib4.21, which differ from the corresponding compounds Ib1.01–Ib1.21 in that $R^{14}$ is ethyl and $R^{15}$ is methyl:

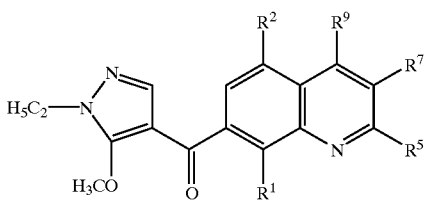

Ib4 the compounds Ib5.01–Ib5.21, which differ from the corresponding compounds Ib1.01–Ib1.21 in that $R^{15}$ is ethyl:

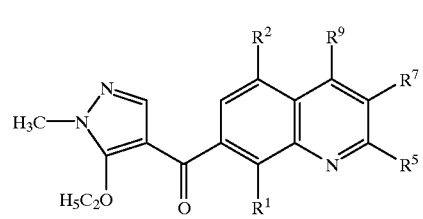

Ib5 the compounds Ib6.01–Ib6.21, which differ from the corresponding compounds Ib1.01–Ib1.21 in that $R^{14}$ and $R^{15}$ are ehyl:

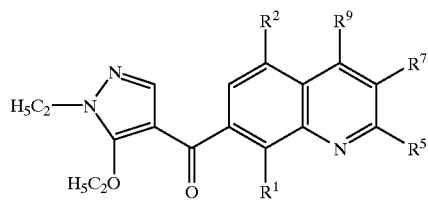
Ib6 the compounds Ib7.01–Ib7.21, which differ from the corresponding compounds Ib1.01–Ib1.21 in that $R^{15}$ is n-propyl:

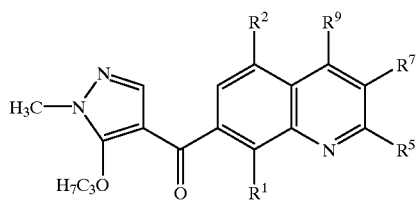
Ib7 the compounds Ib8.01–Ib8.21, which differ from the compounds Ib1.01–Ib1.21 in that $R^{14}$ is ethyl and $R^{15}$ is n-propyl:

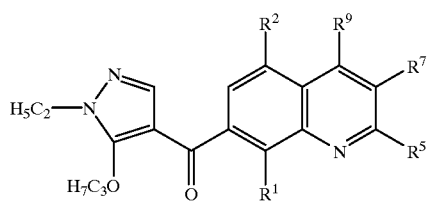
Ib8 the compounds Ib9.01–Ib9.21, which differ from the compounds Ib1.01–Ib1.21 in that $R^{15}$ is n-butyl:

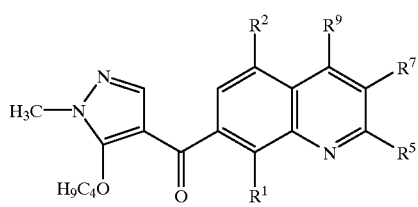
Ib9 the compounds Ib11.01–Ib11.21, which differ from the compounds Ib1.01–Ib1.21 in that $R^{14}$ is ethyl and $R^{15}$ is n-butyl:

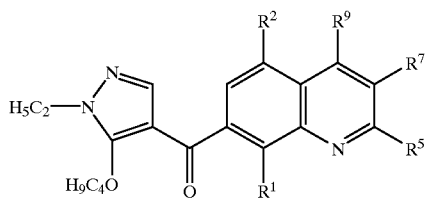
Ib10 the compounds Ib11.01–Ib11.21 which differ from the compounds Ib1.01–Ib1.21 in that $R^{15}$ is methylcarbonyl:

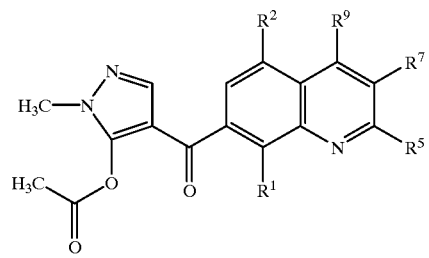
Ib11 the compounds Ib12.01–Ib12.21, which differ from the compounds Ib1.01–Ib1.21 in that $R^{14}$ is ethyl and $R^{15}$ is methylcarbonyl:

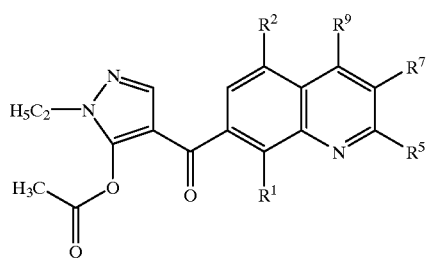
Ib12 the compounds Ib13.01–Ib13.21, which differ from the compounds Ib1.01–Ib1.21 in that $R^{15}$ is ethylcarbonyl:

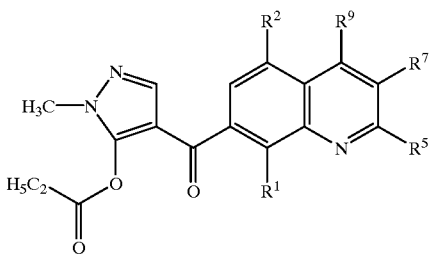
Ib13 the compounds Ib14.01–Ib14.21, which differ from the compounds Ib1.01–Ib1.21 in that $R^{14}$ is ethyl and $R^{15}$ is ethylcarbonyl:

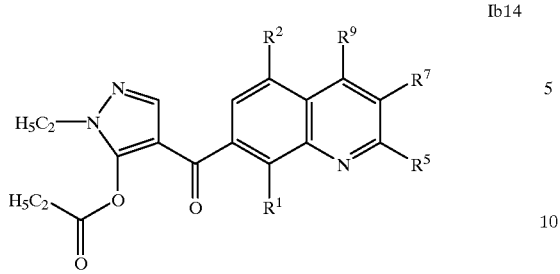

Ib14 the compounds Ib15.01–Ib15.21, which differ from the compounds Ib1.01–Ib1.21 in that $R^{15}$ is n-propylcarbonyl:

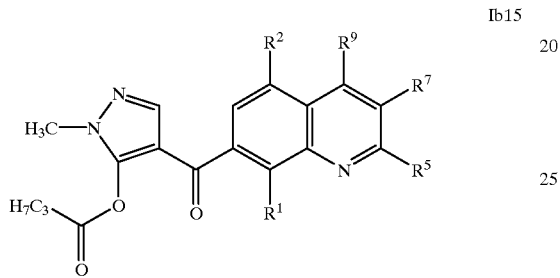

Ib15 the compounds Ib16.01–Ib16.21, which differ from the compounds Ib1.01–Ib1.21 in that $R^{14}$ is ethyl and $R^{15}$ is n-propylcarbonyl:

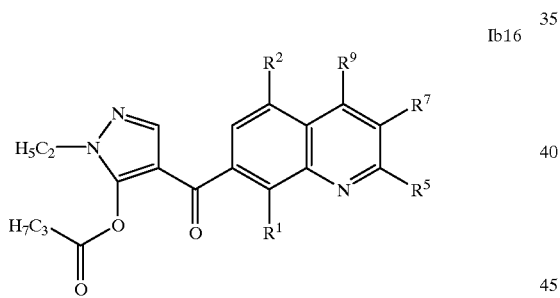

Ib16 the compounds Ib17.01–Ib17.21, which differ from the compounds Ib1.01–Ib1.21 in that $R^{15}$ is n-butylcarbonyl:

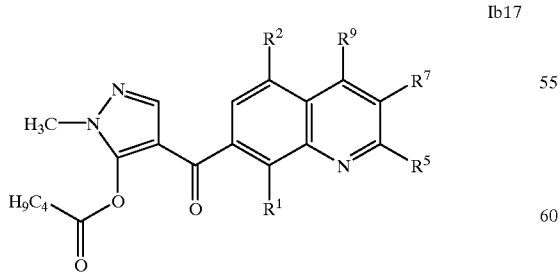

Ib17 the compounds Ib18.01–Ib18.21, which differ from the compounds Ib1.01–Ib1.21 in that $R^{14}$ is ethyl and $R^{15}$ is n-butylcarbonyl:

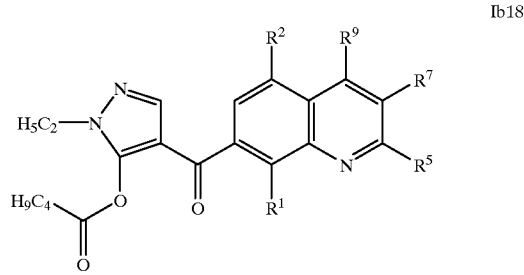

Ib18 the compounds Ib19.01–Ib19.21, which differ from the compounds Ib1.01–Ib1.21 in that $R^{15}$ is trifluoromethylcarbonyl:

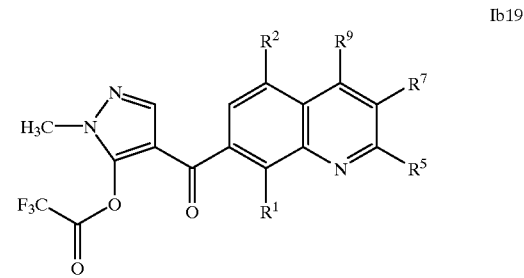

Ib19 the compounds Ib20.01–Ib20.21, which differ from the compounds Ib1.01–Ib1.21 in that $R^{14}$ is ethyl and $R^{15}$ is trifluorocarbonyl:

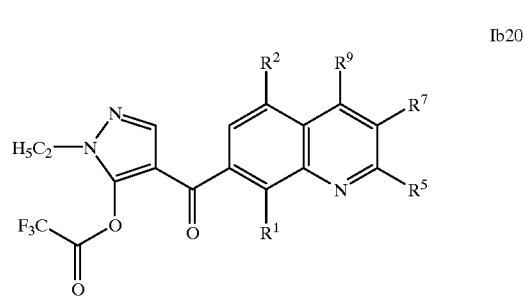

Ib20 the compounds Ib21.01–Ib21.21, which differ from the compounds Ib1.01–Ib1.21 in that $R^{15}$ is methylsulfonyl:

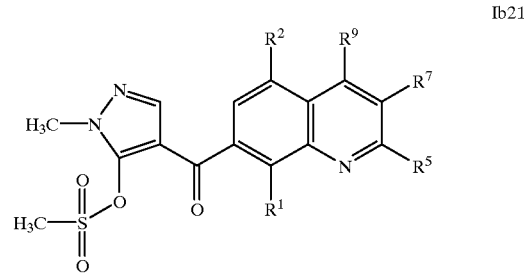

Ib21 the compounds Ib22.01–Ib22.21, which differ from the compounds Ib1.01–Ib1.21 in that $R^{14}$ is ethyl and $R^{15}$ is methylsulfonyl:

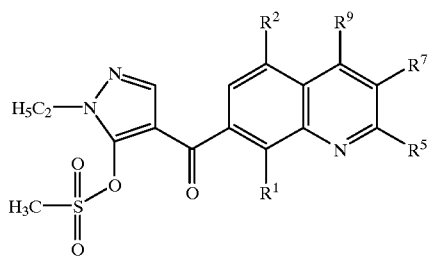

Ib22 the compounds Ib23.01–Ib23.21, which differ from the compounds Ib1.01–Ib1.21 in that $R^{15}$ is ethylsulfonyl:

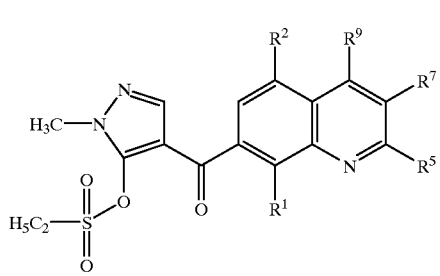

Ib23 the compounds Ib24.01–Ib24.21, which differ from the compounds Ib1.01–Ib1.21 in that $R^{14}$ is ethyl and $R^{15}$ is ethylsulfonyl:

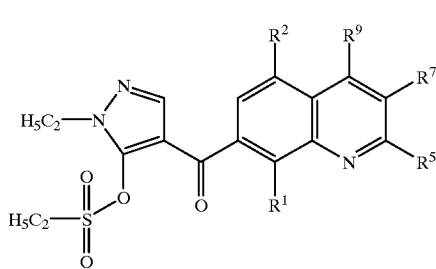

Ib24 the compounds Ib25.01–Ib25.21, which differ from the compounds Ib1.01–Ib1.21 in that $R^{15}$ is n-propylsulfonyl:

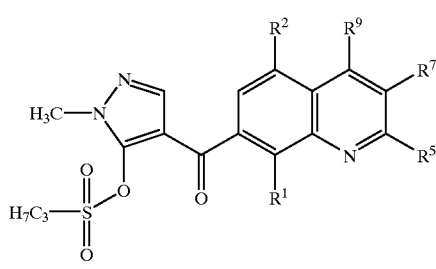

Ib25 the compounds Ib26.01–Ib26.21, which differ from the compounds Ib1.01–Ib1.21 in that $R^{14}$ is ethyl and $R^{15}$ is n-propylsulfonyl:

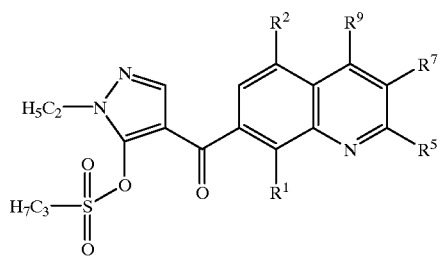

Ib26 the compounds Ib27.01–Ib27.21, which differ from the compounds Ib1.01–Ib1.21 in that $R^{15}$ is n-butylsulfonyl:

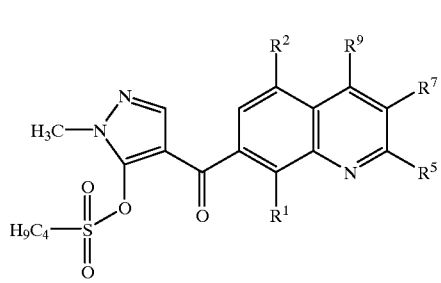

Ib27 the compounds Ib28.01–Ib28.21, which differ from the compounds Ib1.01–Ib1.21 in that $R^{14}$ is ethyl and $R^{15}$ is n-butylsulfonyl:

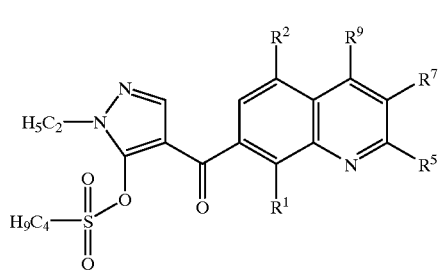

Ib28 the compounds Ib29.01–Ib29.21, which differ from the Icompounds Ib1.01–Ib1.21 in that $R^{15}$ is trifluoromethylsulfonyl:

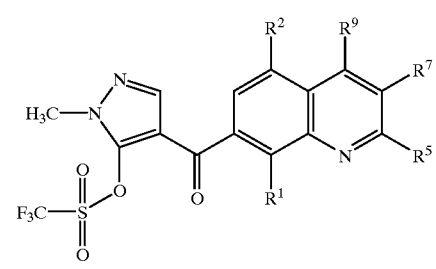

Ib29 the compounds Ib30.01–Ib30.21, which differ from the compounds Ib1.01–Ib1.21 in that $R^{14}$ is ethyl and $R^{15}$ is trifluoromethylsulfonyl:

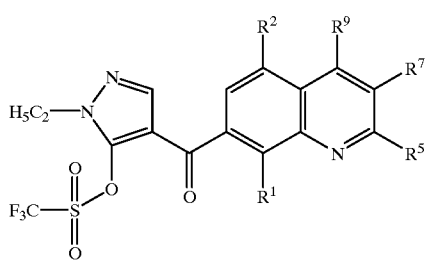

Ib30 the compounds Ib31.01–Ib31.21, which differ from the compounds Ib1.01–Ib1.21 in that $R^{15}$ is phenylsulfonyl:

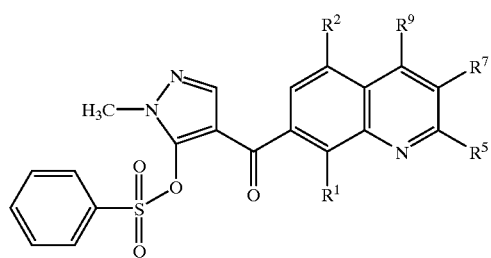

Ib31 the compounds Ib32.01–Ib32.21, which differ from the compounds Ib1.01–Ib1.21 in that $R^{14}$ is ethyl and $R^{15}$ is phenylsulfonyl:

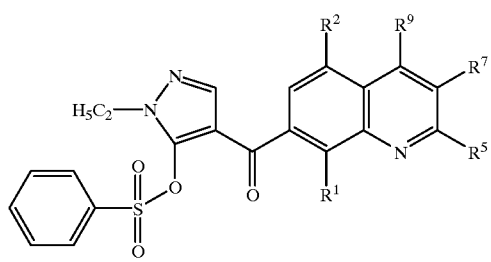

Ib32 the compounds Ib33.01–Ib33.21, which differ from the compounds Ib1.01–Ib1.21 in that $R^{15}$ is 4-methylphenylsulfonyl:

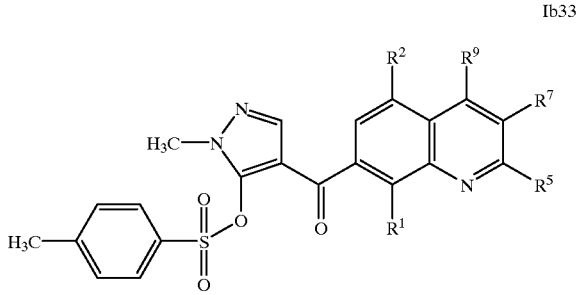

Ib33 the compounds Ib34.01–Ib34.21, which differ from the compounds Ib1.01–Ib1.21 in that $R^{14}$ is ethyl and $R^{15}$ is 4-methylphenylsulfonyl:

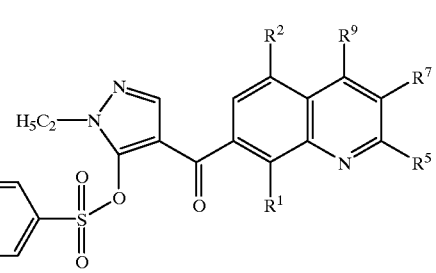

Ib34 the compounds Ib35.01-Ib35.21, which differ from the compounds Ib1.01-Ib1.21 in that $R^{16}$ is methyl:

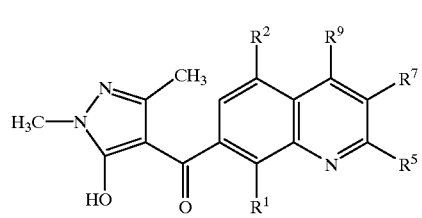

Ib35 the compounds Ib36.01–Ib36.21, which differ from the compounds Ib1.01–Ib1.21 in that $R^{14}$ is ethyl and $R^{16}$ is methyl:

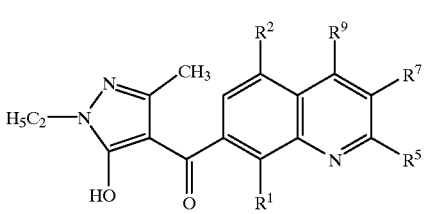

Ib36 the compounds Ib37.01–Ib37.21, which differ from the compounds Ib1.01–Ib1.21 in that $R^{15}$ and $R^{16}$ are each methyl:

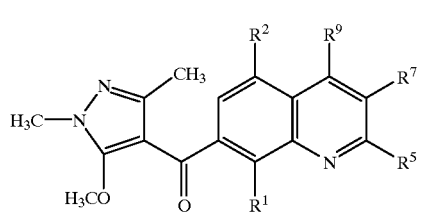

Ib37 the compounds Ib38.01–Ib38.21, which differ from the compounds Ib1.01–Ib1.21 in that $R^{14}$ is ethyl and $R^{15}$ and $R^{16}$ are each methyl:

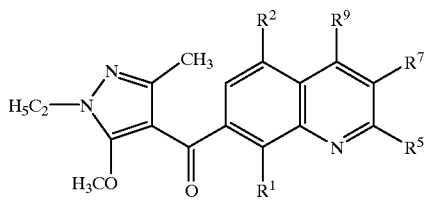
Ib38 the compounds Ib39.01–Ib39.21, which differ from the compounds Ib1.01–Ib1.21 in that $R^{15}$ is ethyl and $R^{16}$ is methyl:

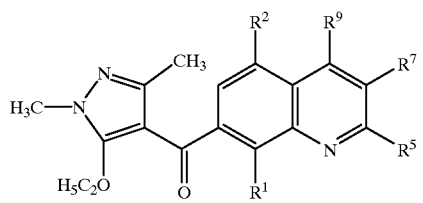
Ib39 the compounds Ib40.01–Ib40.21, which differ from the compounds Ib1.01–Ib1.21 in that R14 and $R^{15}$ are each ethyl and $R^{16}$ is methyl:

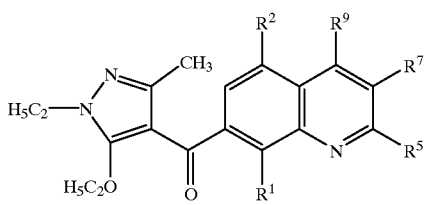
Ib40 the compounds Ib41.01–Ib41.21, which differ from the compounds Ib1.01–Ib1.21 in that $R^{15}$ is n-propyl and $R^{16}$ is methyl:

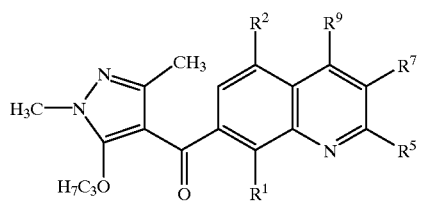
Ib41 the compounds Ib42.01–Ib42.21, which differ from the compounds Ib1.01–Ib1.21 in that $R^{14}$ is ethyl, $R^{15}$ is n-propyl and $R^{16}$ is methyl:

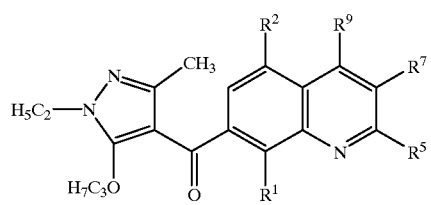
Ib42 the compounds Ib43.01–Ib43.21, which differ from the compounds Ib1.01–Ib1.21 in that $R^{15}$ is n-butyl and $R^{16}$ is methyl:

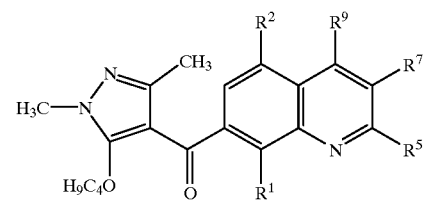
Ib43 the compounds Ib44.01–Ib44.21, which differ from the compounds Ib1.01–Ib1.21 in that $R^{14}$ is ethyl, $R^{15}$ is n-butyl and $R^{16}$ is methyl:

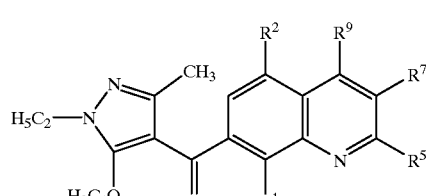
Ib44 the compounds Ib45.01–Ib45.21, which differ from the compounds Ib1.01–Ib1.21 in that $R^{15}$ is methylcarbonyl and $R^{16}$ is methyl:

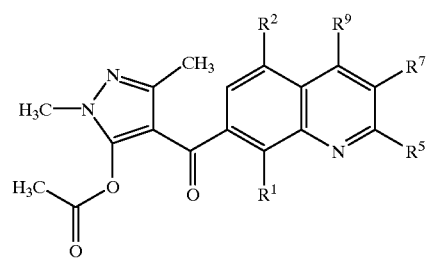
Ib45 the compounds Ib46.01–Ib46.21, which differ from the compounds Ib1.01–Ib1.21 in that $R^{14}$ is ethyl, $R^{15}$ is methylcarbonyl and $R^{16}$ is methyl:

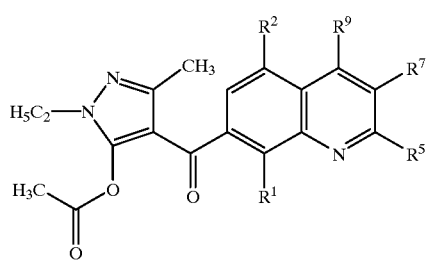

Ib46 the compounds Ib47.01–Ib47.21, which differ from the compounds Ib01–Ib21 in that $R^{15}$ is ethylcarbonyl and $R^{16}$ is methyl:

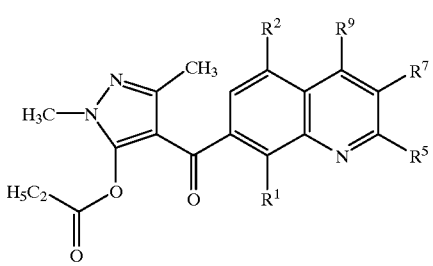

Ib47 the compounds Ib48.01–Ib48.21, which differ from the compounds Ib1.01–Ib1.21 in that $R^{14}$ is ethyl, $R^{15}$ is ethylcarbonyl and $R^{16}$ is methyl:

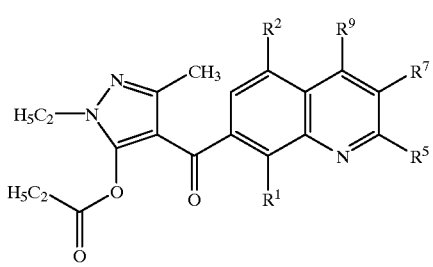

Ib48 the compounds Ib49.01–Ib49.21, which differ from the compounds Ib1.01–Ib1.21 in that $R^{15}$ is n-propylcarbonyl and $R^{16}$ is methyl:

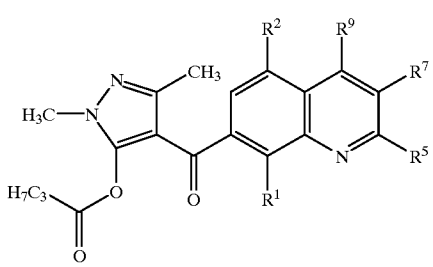

Ib49 the compounds Ib50.01–Ib50.21, which differ from the corresponding compounds Ib1.01–Ib1.21 in that $R^{14}$ is ethyl, $R^{15}$ is n-propylcarbonyl and $R^{16}$ is methyl:

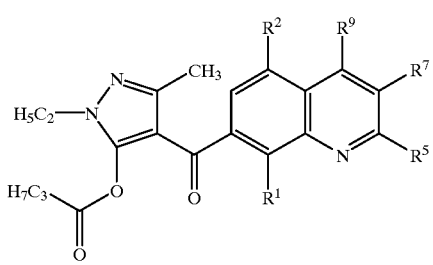

Ib50 the compounds Ib51.01–Ib51.21, which differ from the compounds Ib1.001–Ib1.211 [sic] in that $R^{15}$ is n-butylcarbonyl and $R^{16}$ is methyl:

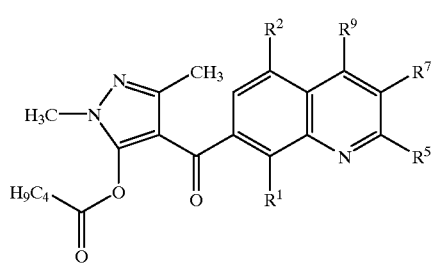

Ib51 the compounds Ib52.01–Ib52.21, which differ from the compounds Ib1.01–Ib1.21 in that $R^{14}$ is ethyl, $R^{15}$ is n-butylcarbonyl and $R^{16}$ is methyl:

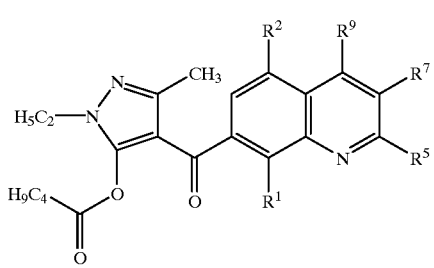

Ib52 the compounds Ib53.01–Ib53.21, which differ from the compounds Ib1.01–Ib1.21 in that $R^{15}$ is trifluoromethylcarbonyl and $R^{16}$ is methyl:

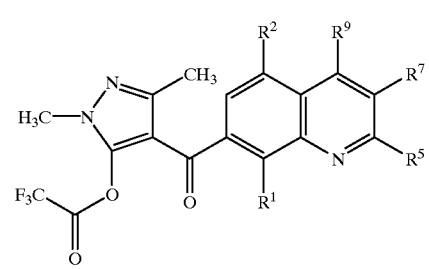

Ib53 the compounds Ib54.01–Ib54.21, which differ from the compounds Ib1.01–Ib1.21 in that $R^{14}$ is ethyl, $R^{15}$ is trifluoromethylcarbonyl and $R^{16}$ is methyl:

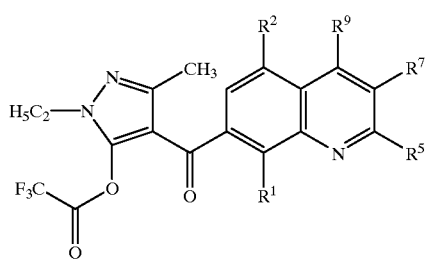

Ib54

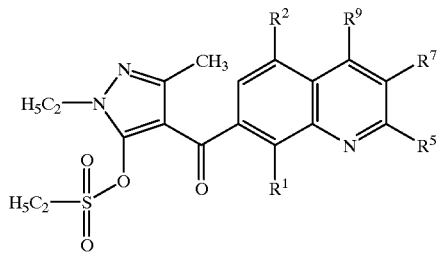

Ib58 the compounds Ib55.01–Ib55.21, which differ from the compounds Ib1.01–Ib1.21 in that $R^{15}$ is methylsulfonyl and $R^{16}$ is methyl:

the compounds Ib59.01–Ib59.21, which differ from the compounds Ib01–Ib21 in that $R^{15}$ is n-propylsulfonyl and $R^{16}$ is methyl:

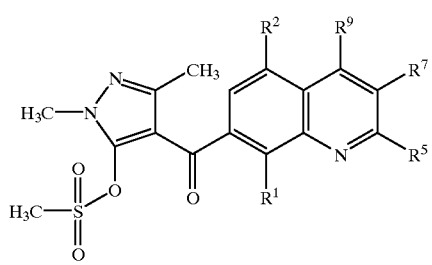

Ib55

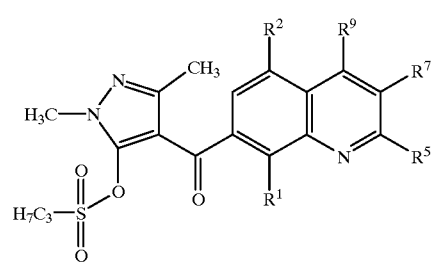

Ib59 the compounds Ib56.01–Ib56.21, which differ from the compounds Ib1.01–Ib1.21 in that $R^{14}$ is ethyl, $R^{15}$ is methylsulfonyl and $R^{16}$ is methyl:

the compounds Ib60.01–Ib60.21, which differ from the compounds Ib1.01–Ib1.21 in that $R^{14}$ is ethyl, $R^{15}$ is n-propylsulfonyl and $R^{16}$ is methyl:

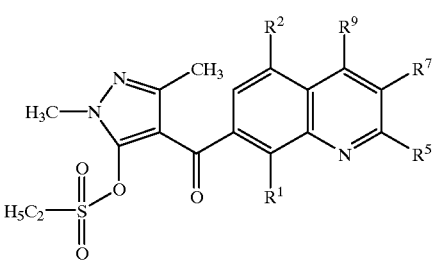

Ib56

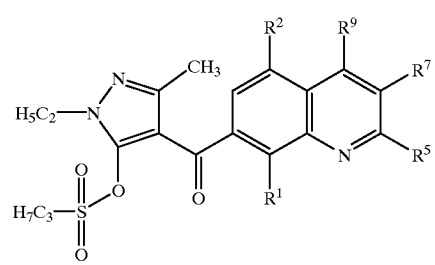

Ib60 the compounds Ib57.01–Ib57.21, which differ from the compounds Ib1.01–Ib1.21 in that $R^{15}$ is ethylsulfonyl and $R^{16}$ is methyl:

the compounds Ib61.01–Ib61.21, which differ from the compounds Ib01–Ib21 in that $R^{15}$ is n-butylsulfonyl and $R^{16}$ is methyl:

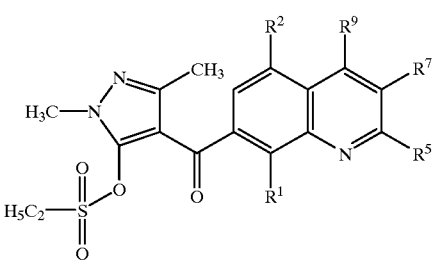

Ib57

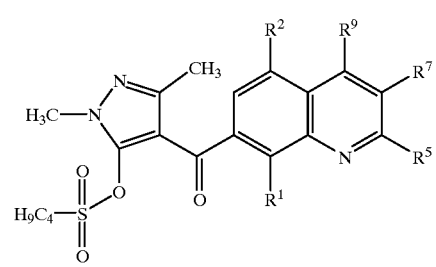

Ib61 the compounds Ib58.O1–Ib58.21, which differ from the compounds Ib1.01–Ib1.21 in that $R^{14}$ is ethyl, $R^{15}$ is ethsulfonyl and $R^{16}$ is methyl:

the compounds Ib62.01–Ib62.21, which differ from the compounds Ib01–Ib21 in that $R^{14}$ is ethyl, $R^{15}$ is n-butylsulfonyl and $R^{16}$ is methyl:

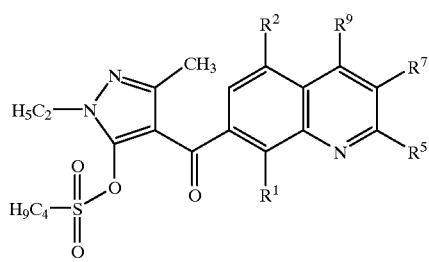

Ib62 the compounds Ib63.01–Ib63.21, which differ from the compounds Ib01–Ib21 in that $R^{15}$ is trifluoromethylsulfonyl and $R^{16}$ is methyl:

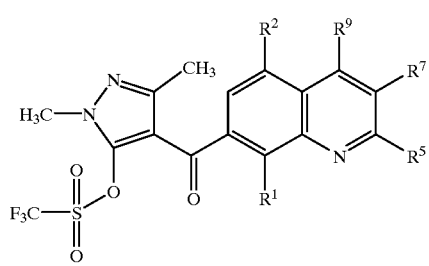

Ib63 the compounds Ib64.01–Ib64.21, which differ from the compounds Ib01–Ib21 in that $R^{14}$ is ethyl, $R^{15}$ is trifluoromethylsulfonyl and $R^{16}$ is methyl:

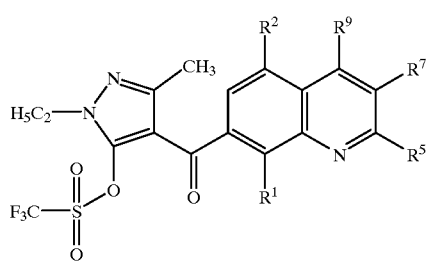

Ib64 the compounds Ib65.01–Ib65.21, which differ from the compounds Ib01–Ib21 in that $R^{15}$ is phenylsulfonyl and $R^{16}$ is methyl:

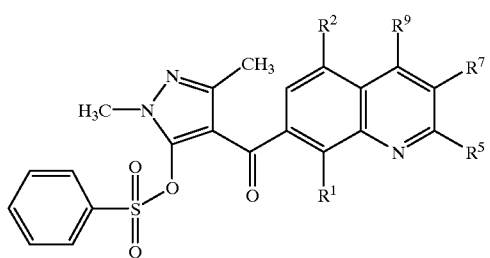

Ib65 the compounds Ib66.01–Ib66.21, which differ from the compounds Ib1.01–Ib1.21 in that $R^{14}$ is ethyl, $R^{15}$ is phenylsulfonyl and $R^{16}$ is methyl:

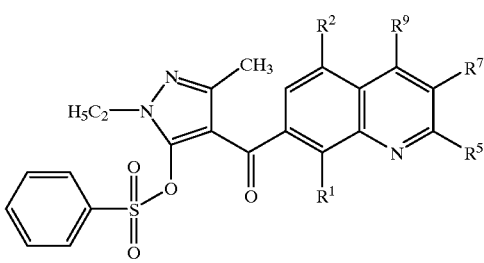

Ib66 the compounds Ib67.01–Ib67.21, which differ from the compounds Ib1.01–Ib1.21 in that $R^{15}$ is 4-methylphenylsulfonyl and $R^{16}$ is methyl:

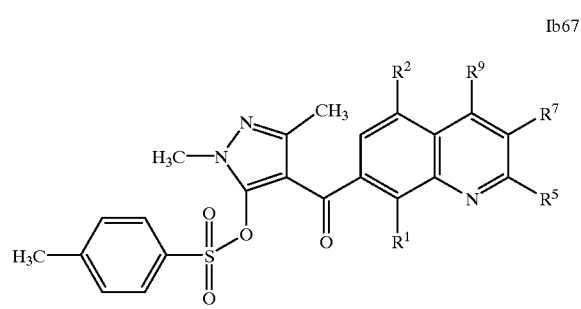

Ib67 the compounds Ib68.01–Ib68.21, which differ from the compounds Ib1.01–Ib1.21 in that $R^{14}$ is ethyl, $R^{15}$ is 4-methylphenylsulfonyl and $R^{16}$ is methyl:

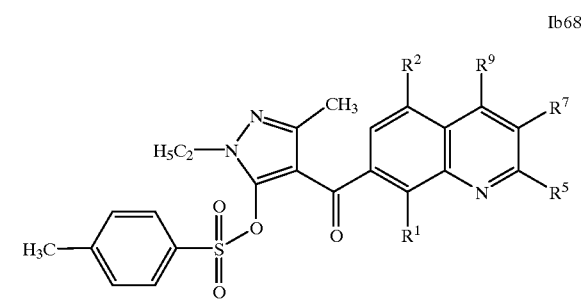

Ib68

In addition, very particular preference is given to the compounds Ic1 (= I where $R^2$, $R^{15}$, $R^{16}$=H and $R^{14}$=CH$_3$ and where the "Q-CO-fragment" is attached in position d, $R^1$ is attached in position a and $Z^1$ is attached in positions b and c) listed in Table 3 below:

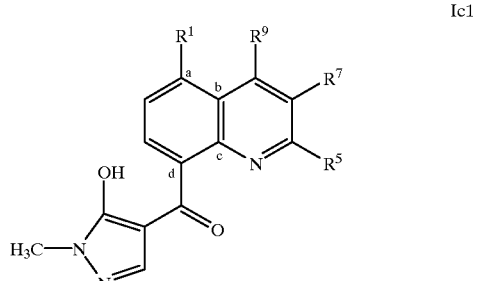

Ic1

TABLE 3

| No. | $R^1$ | $R^5$ | $R^7$ | $R^9$ |
|---|---|---|---|---|
| Ic1.01 | Br | $CH_3$ | H | H |
| Ic1.02 | Cl | $CH_3$ | H | H |
| Ic1.03 | $SO_2CH_3$ | $CH_3$ | H | H |
| Ic1.04 | $CH_3$ | $CH_3$ | H | H |
| Ic1.05 | OH | $CH_3$ | H | H |
| Ic1.06 | $OCH_3$ | $CH_3$ | H | H |
| Ic1.07 | $CF_3$ | $CH_3$ | H | H |
| Ic1.08 | $NO_2$ | $CH_3$ | H | H |
| Ic1.09 | F | $CH_3$ | H | H |
| Ic1.10 | $OCF_3$ | $CH_3$ | H | H |
| Ic1.11 | $C_6H_5$ | $CH_3$ | H | H |
| Ic1.12 | Br | $CF_3$ | H | H |
| Ic1.13 | Cl | $CF_3$ | H | H |
| Ic1.14 | $SO_2CH_3$ | $CF_3$ | H | H |
| Ic1.15 | $CH_3$ | $CF_3$ | H | H |
| Ic1.16 | OH | $CF_3$ | H | H |
| Ic1.17 | $OCH_3$ | $CF_3$ | H | H |
| Ic1.18 | $CF_3$ | $CF_3$ | H | H |
| Ic1.19 | $NO_2$ | $CF_3$ | H | H |
| Ic1.20 | F | $CF_3$ | H | H |
| Ic1.21 | $OCF_3$ | $CF_3$ | H | H |
| Ic1.22 | $C_6H_5$ | $CF_3$ | H | H |
| Ic1.23 | Br | H | H | H |
| Ic1.24 | Cl | H | H | H |
| Ic1.25 | $SO_2CH_3$ | H | H | H |
| Ic1.26 | $CH_3$ | H | H | H |
| Ic1.27 | OH | H | H | H |
| Ic1.28 | $OCH_3$ | H | H | H |
| Ic1.29 | $CF_3$ | H | H | H |
| Ic1.30 | $NO_2$ | H | H | H |
| Ic1.31 | F | H | H | H |
| Ic1.32 | $OCF_3$ | H | H | H |
| Ic1.33 | $C_6H_5$ | H | H | H |
| Ic1.34 | Br | Cl | H | H |
| Ic1.35 | Cl | Cl | H | H |
| Ic1.36 | $SO_2CH_3$ | Cl | H | H |
| Ic1.37 | $CH_3$ | Cl | H | H |
| Ic1.38 | OH | Cl | H | H |
| Ic1.39 | $OCH_3$ | Cl | H | H |
| Ic1.40 | $CF_3$ | Cl | H | H |
| Ic1.41 | $NO_2$ | Cl | H | H |
| Ic1.42 | F | Cl | H | H |
| Ic1.43 | $OCF_3$ | Cl | H | H |
| Ic1.44 | $C_6H_5$ | Cl | H | H |

Furthermore, very particular preference is given to the following hetaroyl derivatives of the formula I:

the compounds Ic2.01–Ic2.44, which differ from the compounds Ic1.01–Ic1.44 in that $R^{14}$ is ethyl:

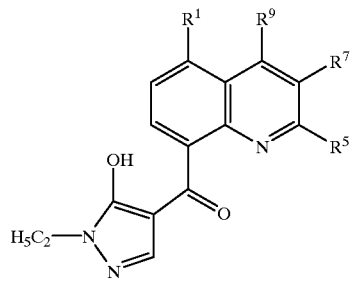

the compounds Ic3.01–Ic3.44, which differ from the compounds Ic1.01–Ic1.44 in that $R^{15}$ is methyl:

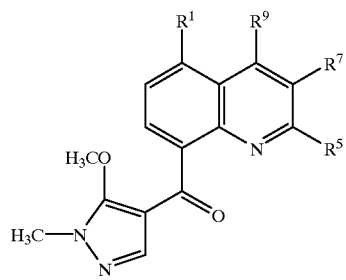

the compounds Ic4.01–Ic4.44, which differ from the compounds Ic1.01–Ic1.44 in that $R^{14}$ is ethyl and $R^{15}$ is methyl:

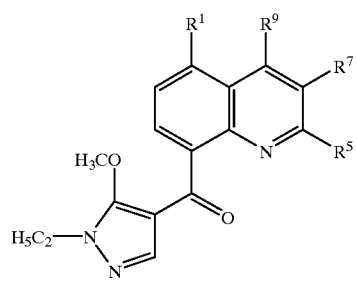

the compounds Ic5.01–Ic5.44, which differ from the corresponding compounds Ic1.01–Ic1.44 in that $R^{15}$ is ethyl:

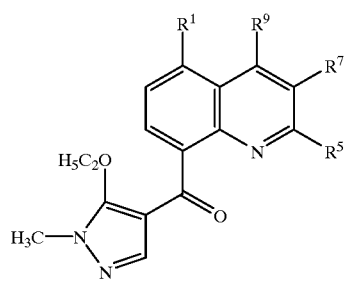

the compounds Ic6.01–Ic6.44, which differ from the corresponding compounds Ic1.01–Ic1.44 in that $R^{14}$ and $R^{15}$ are each ethyl:

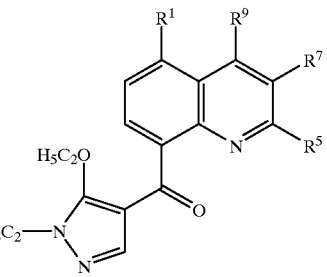

the compounds Ic7.01–Ic7.44, which differ from the corresponding compounds Ic1.01–Ic1.44 in that $R^{15}$ is n-propyl:

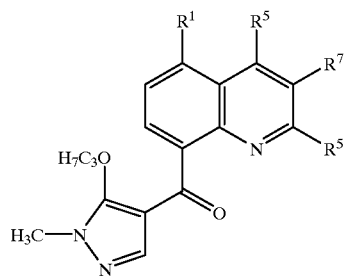

Ic7 the compounds Ic8.01–Ic8.44, which differ from the compounds Ic1.01–Ic1.44 in that $R^{14}$ is ethyl and $R^{15}$ is n-propyl:

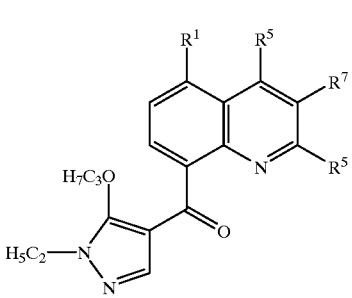

Ic8 the compounds Ic9.01–Ic9.44, which differ from the compounds Ic1.01–Ic1.44 in that $R^{15}$ is n-butyl:

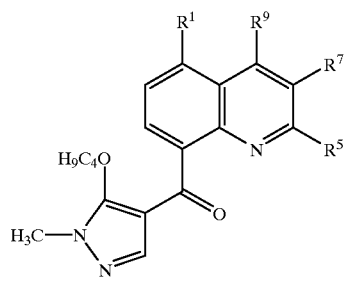

Ic9 the compounds Ic10.01–Ic10.44, which differ from the compounds Ic1.01–Ic1.44 in that $R^{14}$ is ethyl and $R^{15}$ is n-butyl:

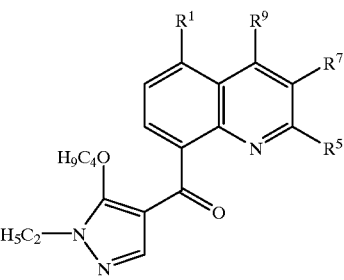

Ic10 the compounds Ic11.01–Ic11.44, which differ from the compounds Ic1.01–Ic1.44 in that $R^{15}$ is methylcarbonyl:

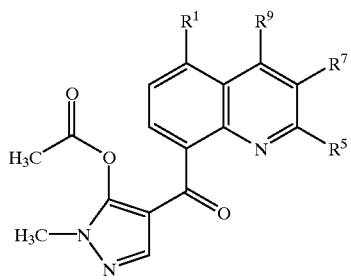

Ic11 the compounds Ic12.01–Ic12.44, which differ from the compounds Ic1.01–Ic1.44 in that $R^{14}$ is ethyl and $R^{15}$ is methylcarbonyl:

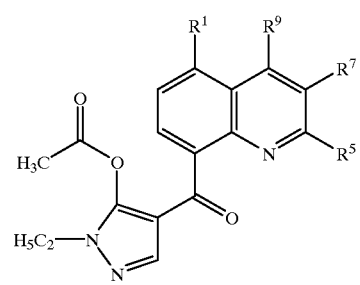

Ic12 the compounds Ic1.01–Ic1.44 in that $R^{15}$ is ethylcarbonyl:

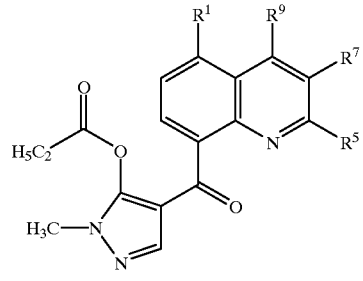

Ic13 the compounds Ic14.01–Ic14.44, which differ from the compounds Ic1.01–Ic1.44 in that $R^{14}$ is ethyl and $R^{15}$ is ethylcarbonyl:

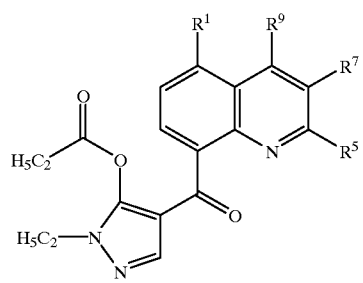

Ic14 the compounds Ic15.01–Ic15.44, which differ from the compounds Ic1.01–Ic1.44 in that $R^{15}$ is n-propylcarbonyl:

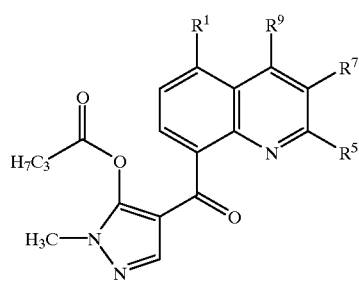

Ic15 the compounds Ic16.01–Ic16.44, which differ from the compounds Ic1.01–Ic1.44 in that $R^{14}$ is ethyl and $R^{15}$ is n-propylcarbonyl:

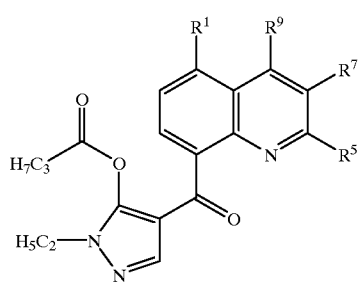

Ic16 the compounds Ic17.01–Ic17.44, which differ from the compounds Ic1.01–Ic1.44 in that $R^{15}$ is n-butylcarbonyl:

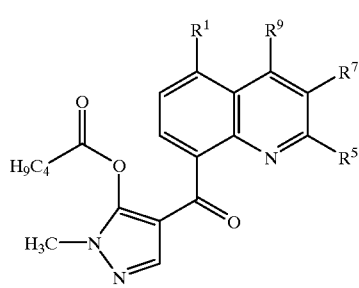

Ic17 the compounds Ic18.01–Ic18.44, which differ from the compounds Ic1.01–Ic1.44 in that $R^{14}$ is ethyl and $R^{15}$ is n-butylcarbonyl:

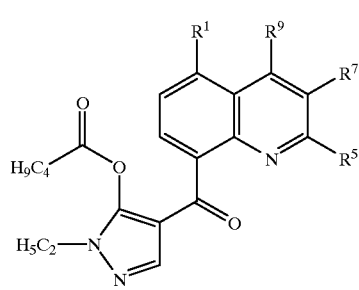

Ic18 the compounds Ic19.01–Ic19.44, which differ from the compounds Ic1.01–Ic1.44 in that $R^{15}$ is trifluoromethylcarbonyl:

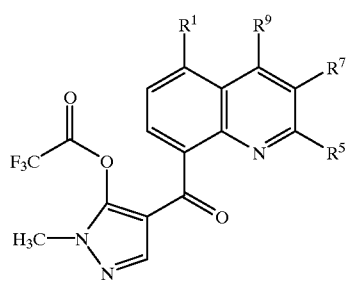

Ic19 the compounds Ic20.01–Ic20.44, which differ from the compounds Ic1.01–Ic1.44 in that $R^{14}$ is ethyl and $R^{15}$ is trifluoromethylcarbonyl:

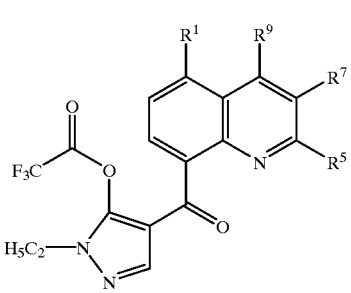

Ic20 the compounds Ic21.01–Ic21.44, which differ from the compounds Ic1.01–Ic1.44 in that $R^{15}$ is methylsulfonyl:

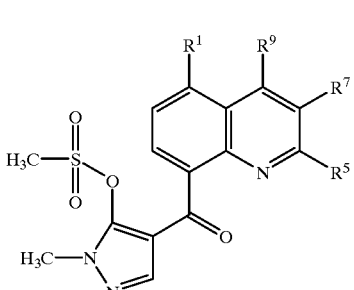

Ic21 the compounds Ic22.01–Ic22.44, which differ from the compounds Ic1.01–Ic1.44 in that $R^{14}$ is ethyl and $R^{15}$ is methylsulfonyl:

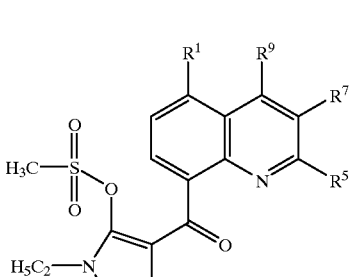

Ic22 the compounds Ic23.01–Ic23.44, which differ from the compounds Ic1.01–Ic1.44 in that $R^{15}$ is ethylsulfonyl:

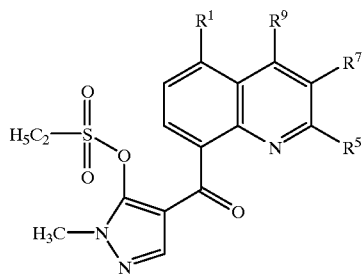

Ic23 the compounds Ic24.01–Ic24.44, which differ from the compounds Ic1.01–Ic1.44 in that $R^{14}$ is ethyl and $R^{15}$ is ethylsulfonyl:

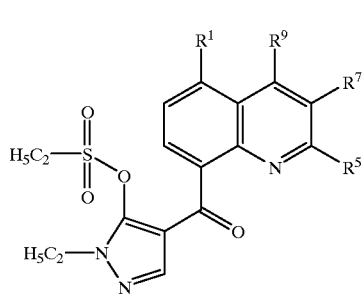

Ic24 the compounds Ic25.01–Ic25.44, which differ from the compounds Ic1.01–Ic1.44 in that $R^{15}$ is n-propylsulfonyl:

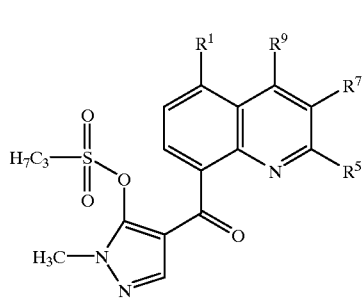

Ic25 the compounds Ic26.01–Ic26.44, which differ from the compounds Ic1.01–Ic1.44 in that $R^{14}$ is ethyl and $R^{15}$ is n-propylsulfonyl:

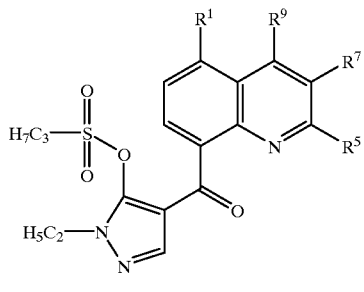

Ic26 the compounds Ic27.01–Ic27.44, which differ from the compounds Ic1.01–Ic1.44 in that $R^{15}$ is n-butylsulfonyl:

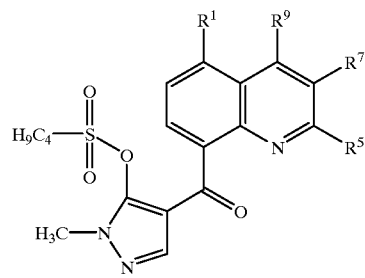

Ic27 the compounds Ic28.01–Ic28.44, which differ from the compounds Ic1.01–Ic1.44 in that $R^{14}$ is ethyl and $R^{15}$ is n-butylsulfonyl:

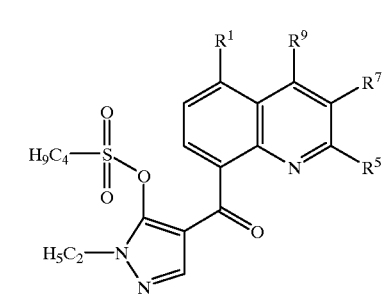

Ic28 the compounds Ic29.01–Ic29.44, which differ from the compounds Ic1.01–Ic1.44 in that $R^{15}$ is trifluoromethylsulfonyl:

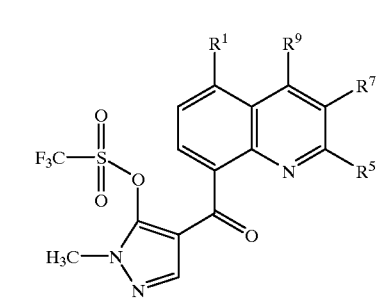

Ic29 the compounds Ic30.01–Ic30.44, which differ from the compounds Ic1.01–Ic1.44 in that $R^{14}$ is ethyl and $R^{15}$ is trifluoromethylsulfonyl:

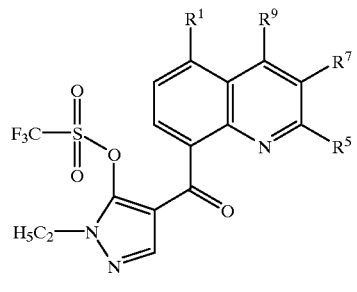

Ic30 the compounds Ic31.01–Ic31.44, which differ from the compounds Ic1.01–Ic1.44 in that $R^{15}$ is phenylsulfonyl:

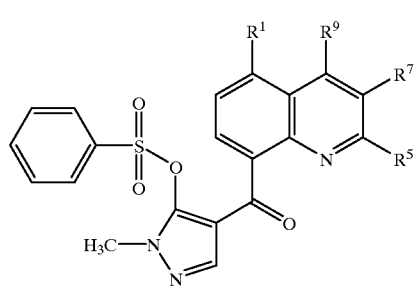
Ic31 the compounds Ic32.01–Ic32.44, which differ from the corresponding compounds Ic1.01–Ic1.44 in that $R^{14}$ is ethyl and $R^{15}$ is phenylsulfonyl:

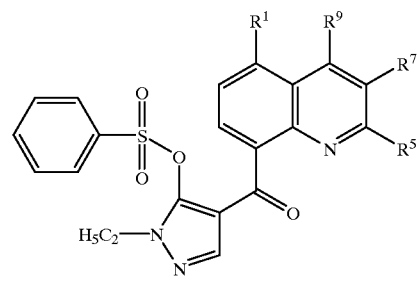
Ic32 the compounds Ic33.01–Ic33.44, which differ from the compounds Ic1.01–Ic1.44 in that $R^{15}$ is 4-methylphenylsulfonyl:

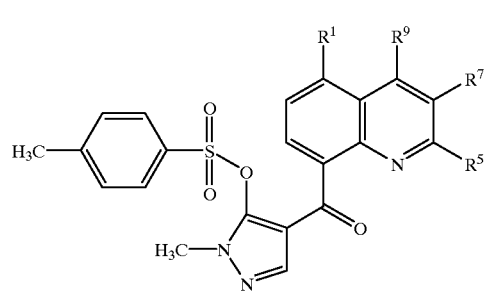
Ic33 the compounds Ic34.01–Ic34.44, which differ from the compounds Ic1.01–Ic1.44 in that $R^{14}$ is ethyl and $R^{15}$ is 4-methylphenylsulfonyl:

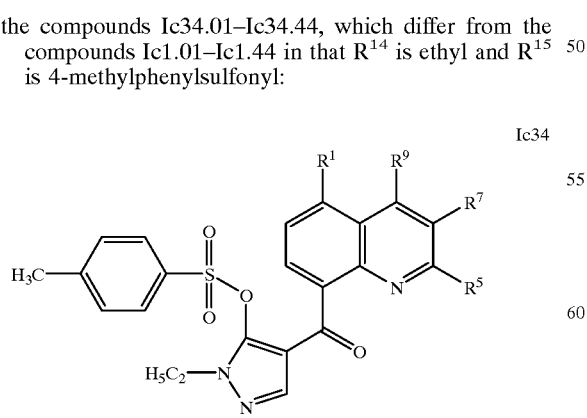
Ic34 the compounds Ic35.01–Ic35.44, which differ from the compounds Ic1.01–Ic1.44 in that $R^{16}$ is methyl:

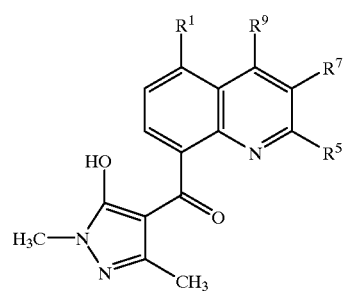
Ic35 the compounds Ic36.01–Ic36.44, which differ from the compounds Ic1.01–Ic1.44 in that $R^{14}$ is ethyl and $R^{16}$ is methyl:

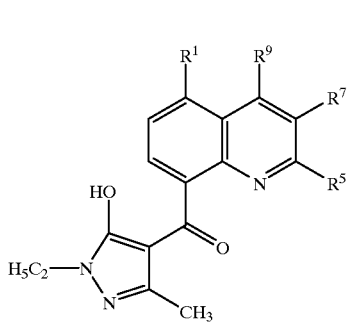
Ic36 the compounds Ic37.01–Ic37.44, which differ from the compounds Ic1.01–Ic1.44 in that $R^{15}$ and $R^{16}$ are each methyl:

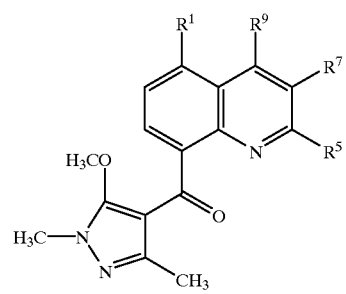
Ic37 the compounds Ic38.01–Ic38.44, which differ from the compounds Ic1.01–Ic1.44 in that $R^{14}$ is ethyl, and $R^{15}$ and $R^{16}$ are each methyl:

Ic38

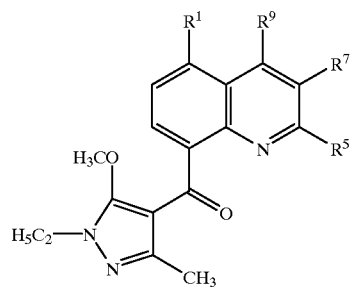

the compounds Ic39.01–Ic39.44, which differ from the compounds Ic1.01–Ic1.44 in that $R^{15}$ is ethyl and $R^{16}$ is methyl:

Ic39

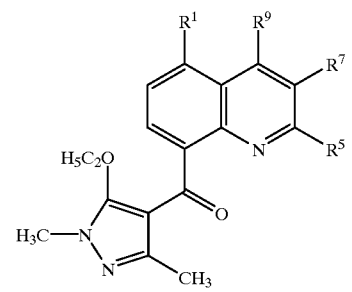

the compounds Ic40.01–Ic40.44, which differ from the compounds Ic1.01–Ic1.44 in that $R^{14}$ and $R^{15}$ are each ethyl and $R^{16}$ is methyl:

Ic40

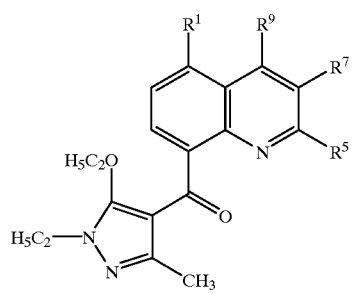

the compounds Ic40.01–Ic40.44, which differ from the compounds Ic1.01–Ic1.44 in that $R^{15}$ is n-propyl and $R^{16}$ is methyl:

Ic41

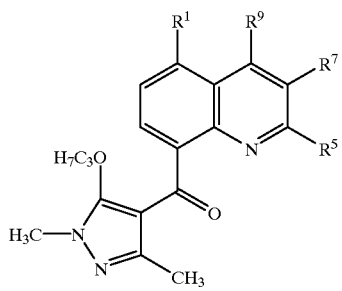

the compounds Ic42.01–Ic42.22, which differ from the compounds Ic1.01–Ic1.44 in that $R^{14}$ is ethyl, $R^{15}$ is n-propyl and $R^{16}$ is methyl:

Ic42

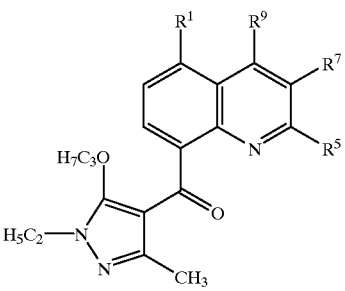

the compounds Ic43.01–Ic43.44, which differ from the compounds Ic1.01–Ic1.44 in that $R^{15}$ is n-butyl and $R^{16}$ is methyl:

Ic43

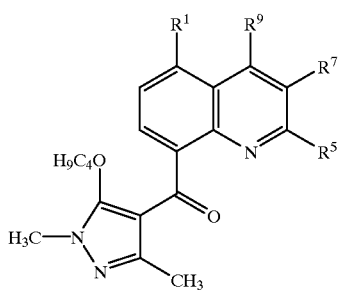

the compounds Ic44.01–Ic44.44, which differ from the compounds Ic1.01–Ic1.44 in that $R^{14}$ is ethyl, $R^{15}$ is n-butyl and $R^{16}$ is methyl:

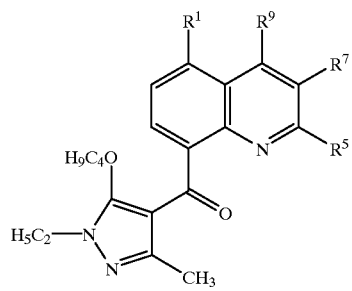

Ic44 the compounds Ic45.01–Ic45.44, which differ from the compounds Ic1.01–Ic1.44 in that $R^{15}$ is methylcarbonyl and $R^{16}$ is methyl:

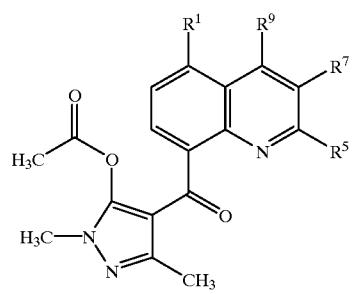

Ic45 the compounds Ic46.01–Ic46.44, which differ from the compounds Ic1.01–Ic1.44 in that $R^{14}$ is ethyl, $R^{15}$ is methylcarbonyl and $R^{16}$ is methyl:

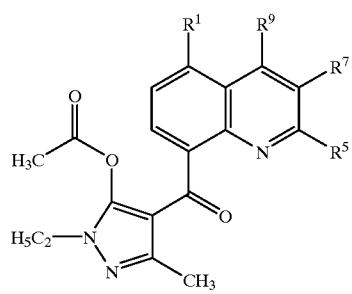

Ic46 the compounds Ic47.01–Ic47.44, which differ from the compounds Ic1.01–Ic1.44 in that $R^{15}$ is ethylcarbonyl and $R^{16}$ is methyl:

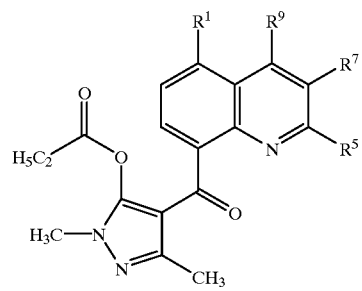

Ic47 the compounds Ic48.01–Ic48.44, which differ from the compounds Ic1.01–Ic1.44 in that $R^{14}$ is ethyl, $R^{15}$ is ethylcarbonyl and $R^{16}$ is methyl:

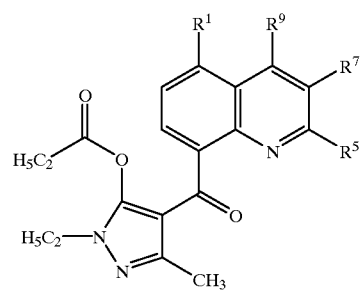

Ic48 the compounds Ic49.01–Ic49.44, which differ from the compounds Ic1.01–Ic1.44 in that $R^{15}$ is n-propylcarbonyl and $R^{16}$ is methyl:

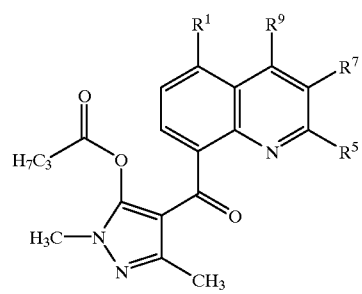

Ic49 the compounds Ic50.01–Ic50.44, which differ from the compounds Ic1.01–Ic1.44 in that $R^{14}$ is ethyl, $R^{15}$ is n-propylcarbonyl and $R^{16}$ is methyl:

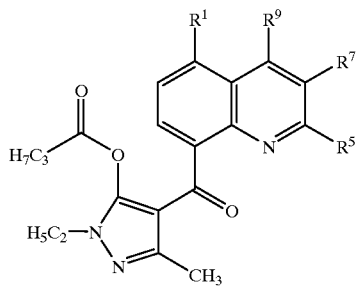

Ic50 the compounds Ic51.01–Ic51.44, which differ from the compounds Ic1.01–Ic1.44 in that $R^{15}$ is n-butylcarbonyl and $R^{16}$ is methyl:

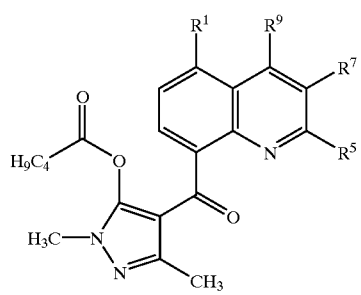

Ic51 the compounds Ic52.01–Ic52.44, which differ from the compounds Ic1.01–Ic1.44 in that $R^{14}$ is ethyl, $R^{15}$ is n-butylcarbonyl and $R^{16}$ is methyl:

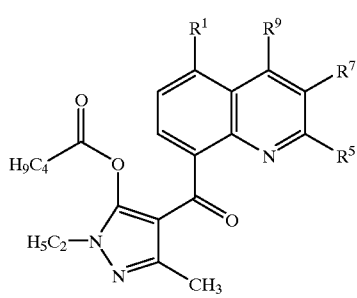

Ic52 the compounds Ic53.01–Ic53.44, which differ from the compounds Ic1.01–Ic1.44 in that $R^{15}$ is trifluoromethylcarbonyl and $R^{16}$ is methyl:

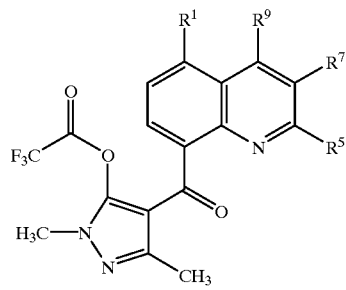

Ic53 the compounds Ic54.01–Ic54.44, which differ from the compounds Ic1.01–Ic1.44 in that $R^{14}$ is ethyl, $R^{15}$ is trifluoromethylcarbonyl and $R^{16}$ is methyl:

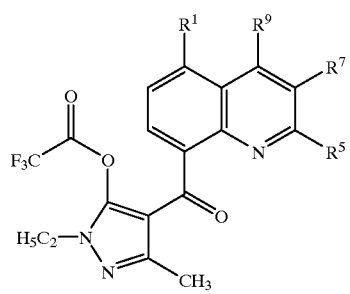

Ic54 the compounds Ic55.01–Ic55.44, which differ from the compounds Ic1.01–Ic1.44 in that $R^{15}$ is methylsulfonyl and $R^{16}$ is methyl:

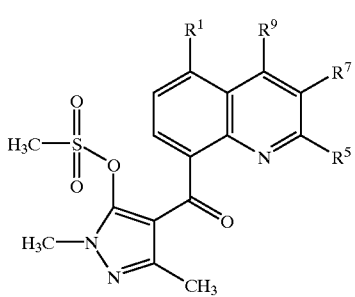

Ic55 the compounds Ic.56.01–Ic56.44, which differ from the compounds Ic1.01–Ic1.44 in that $R^{14}$ is ethyl, $R^{15}$ is methylsulfonyl and $R^{16}$ is methyl:

Ic56

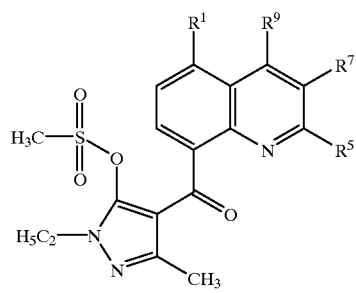

the compounds Ic57.01–Ic57.44, which differ from the compounds Ic1.01–Ic1.44 in that $R^{15}$ is ethylsulfonyl and $R^{16}$ is methyl:

Ic57

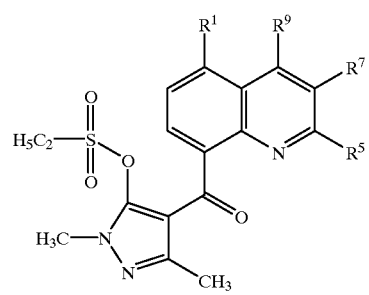

the compounds Ic58.01–Ic58.44, which differ from the compounds Ic1.01–Ic1.44 in that $R^{14}$ is ethyl, $R^{15}$ is ethylsulfonyl and $R^{16}$ is methyl:

Ic58

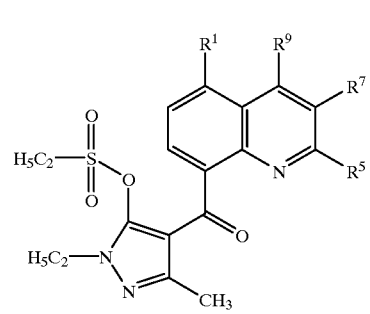

the compounds Ic59.01–Ic59.44, which differ from the compounds Ic1.01–Ic1.44 in that $R^{15}$ is n-propylsulfonyl and $R^{16}$ is methyl:

Ic59

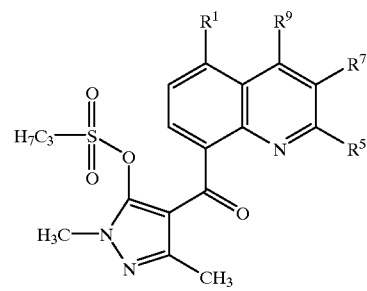

the compounds Ic60.01–Ic60.44, which differ from the compounds Ic1.01–Ic1.44 in that $R^{14}$ is ethyl, $R^{15}$ is n-propylsulfonyl and $R^{16}$ is methyl:

Ic60

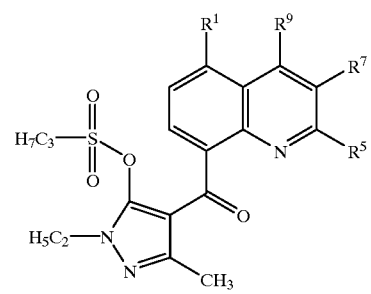

the compounds Ic61.01–Ic61.44, which differ from the compounds Ic1.01–Ic1.44 in that $R^{15}$ is n-butylsulfonyl and $R^{16}$ is methyl:

Ic61

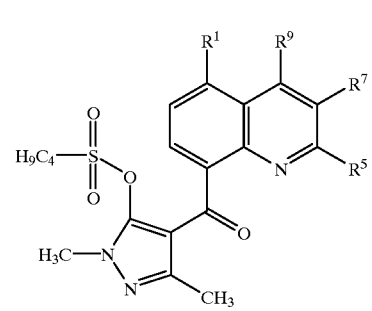

the compounds Ic62.01–Ic62.044, which differ from the compounds Ic1.01–Ic1.44 in that $R^{14}$ is ethyl, $R^{15}$ is n-butylsulfonyl and $R^{16}$ is methyl:

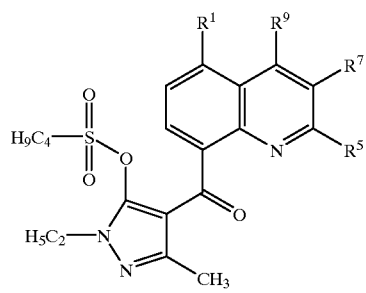

Ic62 the compounds Ic63.01–Ic63.44, which differ from the compounds Ic1.01–Ic1.44 in that $R^{15}$ is trifluoromethylsulfonyl and $R^{16}$ is methyl:

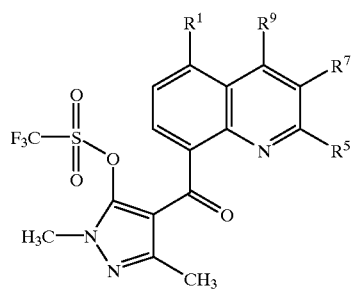

Ic63 the compounds Ic64.01–Ic64.44, which differ from the compounds Ic1.01–Ic1.44 in that $R^{14}$ is ethyl, $R^{15}$ is trifluoromethylsulfonyl and $R^{16}$ is methyl:

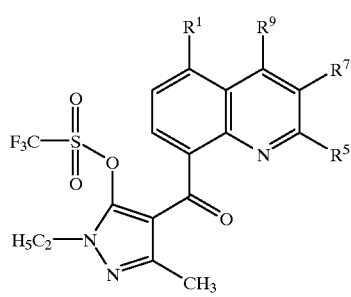

Ic64 the compounds Ic65.01–Ic65.44, which differ from the compounds Ic1.01–Ic1.44 in that $R^{15}$ is phenylsulfonyl and $R^{16}$ is methyl:

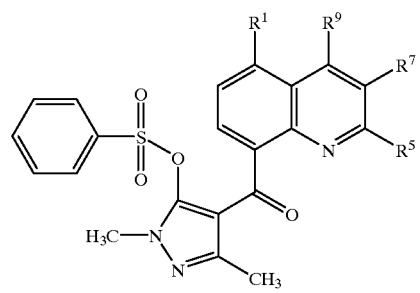

Ic65 the compounds Ic66.01–Ic66.44, which differ from the compounds Ic1.01–Ic1.44 in that $R^{14}$ is ethyl, $R^{15}$ is phenylsulfonyl and $R^{16}$ is methyl:

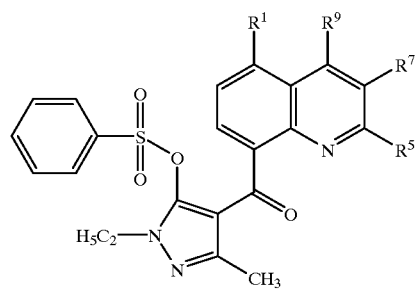

Ic66 the compounds Ic67.01–Ic67.44, which differ from the compounds Ic1.01–Ic1.44 in that $R^{15}$ is 4-methylphenylsulfonyl and $R^{16}$ is methyl:

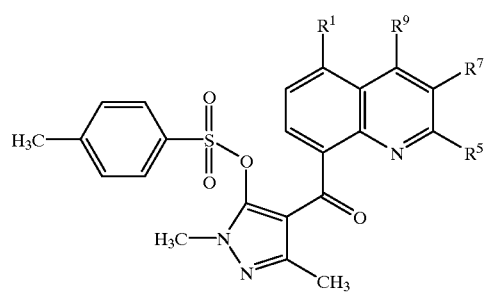

Ic67 the compounds Ic68.01–Ic68.44, which differ from the compounds Ic1.01–Ic1.44 in that $R^{14}$ is ethyl, $R^{15}$ is 4-methylphenylsulfonyl and $R^{16}$ is methyl:

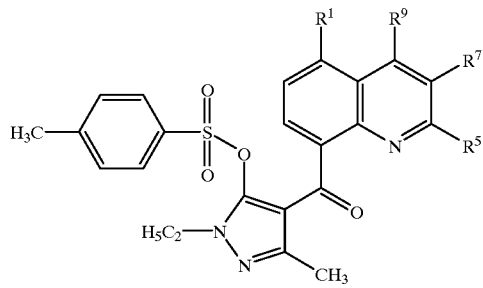

Ic68

In addition, very particular preference is given to the compounds Id1 (= I where $R^2$, $R^{15}$, $R^{16}$=H and $R^{14}$=$CH_3$ and where the "Q-CO-fragment" is attached in position a, $R^1$ is attached in position d and $Z^2$ is attached in positions b and c) listed in Table 4 below:

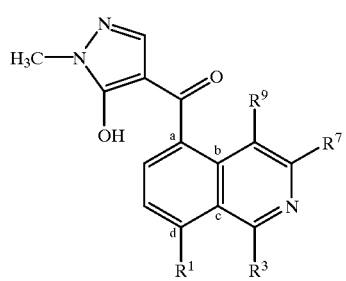

Id1

TABLE 4

| No. | $R^1$ | $R^3$ | $R^7$ | $R^9$ |
|---|---|---|---|---|
| Id1.01 | Br | H | H | H |
| Id1.02 | Cl | H | H | H |
| Id1.03 | $SO_2CH_3$ | H | H | H |
| Id1.04 | $CH_3$ | H | H | H |
| Id1.05 | OH | H | H | H |
| Id1.06 | $OCH_3$ | H | H | H |
| Id1.07 | $CF_3$ | H | H | H |
| Id1.08 | $NO_2$ | H | H | H |
| Id1.09 | F | H | H | H |
| Id1.10 | $OCF_3$ | H | H | H |
| Id1.11 | Br | $CH_3$ | H | H |
| Id1.12 | Cl | $CH_3$ | H | H |
| Id1.13 | $SO_2CH_3$ | $CH_3$ | H | H |
| Id1.14 | $CH_3$ | $CH_3$ | H | H |
| Id1.15 | OH | $CH_3$ | H | H |
| Id1.16 | $OCH_3$ | $CH_3$ | H | H |
| Id1.17 | $CF_3$ | $CH_3$ | H | H |
| Id1.18 | $NO_2$ | $CH_3$ | H | H |
| Id1.19 | F | $CH_3$ | H | H |
| Id1.20 | H | $CH_3$ | H | H |
| Id1.21 | $OCF_3$ | $CH_3$ | H | H |
| Id1.22 | Br | $CH_3$ | $CH_3$ | H |
| Id1.23 | Cl | $CH_3$ | $CH_3$ | H |
| Id1.24 | $SO_2CH_3$ | $CH_3$ | $CH_3$ | H |
| Id1.25 | $CH_3$ | $CH_3$ | $CH_3$ | H |
| Id1.26 | OH | $CH_3$ | $CH_3$ | H |
| Id1.27 | $OCH_3$ | $CH_3$ | $CH_3$ | H |
| Id1.28 | $CF_3$ | $CH_3$ | $CH_3$ | H |
| Id1.29 | $NO_2$ | $CH_3$ | $CH_3$ | H |
| Id1.30 | F | $CH_3$ | $CH_3$ | H |
| Id1.31 | $OCF_3$ | $CH_3$ | $CH_3$ | H |
| Id1.32 | Br | Cl | Cl | Cl |
| Id1.33 | Cl | Cl | Cl | Cl |
| Id1.34 | $SO_2CH_3$ | Cl | Cl | Cl |
| Id1.35 | $CH_3$ | Cl | Cl | Cl |
| Id1.36 | OH | Cl | Cl | Cl |
| Id1.37 | $OCH_3$ | Cl | Cl | Cl |
| Id1.38 | $CF_3$ | Cl | Cl | Cl |
| Id1.39 | $NO_2$ | Cl | Cl | Cl |
| Id1.40 | F | Cl | Cl | Cl |
| Id1.41 | $OCF_3$ | Cl | Cl | Cl |
| Id1.42 | Br | $OCH_3$ | Cl | H |
| Id1.43 | Cl | $OCH_3$ | Cl | H |
| Id1.44 | $SO_2CH_3$ | $OCH_3$ | Cl | H |
| Id1.45 | $CH_3$ | $OCH_3$ | Cl | H |
| Id1.46 | OH | $OCH_3$ | Cl | H |
| Id1.47 | $OCH_3$ | $OCH_3$ | Cl | H |
| Id1.48 | $CF_3$ | $OCH_3$ | Cl | H |
| Id1.49 | $NO_2$ | $OCH_3$ | Cl | H |
| Id1.50 | F | $OCH_3$ | Cl | H |
| Id1.51 | $OCF_3$ | $OCH_3$ | Cl | H |
| Id1.52 | Br | H | $OCH_3$ | H |
| Id1.53 | Cl | H | $OCH_3$ | H |
| Id1.54 | $SO_2CH_3$ | H | $OCH_3$ | H |
| Id1.55 | $CH_3$ | H | $OCH_3$ | H |
| Id1.56 | OH | H | $OCH_3$ | H |
| Id1.57 | $OCH_3$ | H | $OCH_3$ | H |
| Id1.58 | $CF_3$ | H | $OCH_3$ | H |
| Id1.59 | $NO_2$ | H | $OCH_3$ | H |
| Id1.60 | F | H | $OCH_3$ | H |
| Id1.61 | $OCF_3$ | H | $OCH_3$ | H |
| Id1.62 | Br | $CH_3$ | $CH_3$ | $CH_3$ |
| Id1.63 | Cl | $CH_3$ | $CH_3$ | $CH_3$ |
| Id1.64 | $SO_2CH_3$ | $CH_3$ | $CH_3$ | $CH_3$ |
| Id1.65 | $CH_3$ | $CH_3$ | $CH_3$ | $CH_3$ |
| Id1.66 | OH | $CH_3$ | $CH_3$ | $CH_3$ |
| Id1.67 | $OCH_3$ | $CH_3$ | $CH_3$ | $CH_3$ |
| Id1.68 | $CF_3$ | $CH_3$ | $CH_3$ | $CH_3$ |
| Id1.69 | $NO_2$ | $CH_3$ | $CH_3$ | $CH_3$ |
| Id1.70 | F | $CH_3$ | $CH_3$ | $CH_3$ |
| Id1.71 | $OCF_3$ | $CH_3$ | $CH_3$ | $CH_3$ |
| Id1.72 | Br | Cl | H | H |
| Id1.73 | Cl | Cl | H | H |
| Id1.74 | $SO_2CH_3$ | Cl | H | H |
| Id1.75 | $CH_3$ | Cl | H | H |
| Id1.76 | OH | Cl | H | H |
| Id1.77 | $OCH_3$ | Cl | H | H |
| Id1.78 | $CF_3$ | Cl | H | H |
| Id1.79 | $NO_2$ | Cl | H | H |
| Id1.80 | F | Cl | H | H |
| Id1.81 | $OCF_3$ | Cl | H | H |
| Id1.82 | Br | Cl | Cl | H |
| Id1.83 | Cl | Cl | Cl | H |
| Id1.84 | $SO_2CH_3$ | Cl | Cl | H |
| Id1.85 | $CH_3$ | Cl | Cl | H |
| Id1.86 | OH | Cl | Cl | H |
| Id1.87 | $OCH_3$ | Cl | Cl | H |
| Id1.88 | $CF_3$ | Cl | Cl | H |
| Id1.89 | $NO_2$ | Cl | Cl | H |
| Id1.90 | F | Cl | Cl | H |
| Id1.91 | $OCF_3$ | Cl | Cl | H |

Furthermore, very particular preference is given to the following hetaroyl derivatives of the formula I:

the compounds Id2.01–Id2.91, which differ from the compounds Id1.01–Id1.91 in that $R^{14}$ is ethyl:

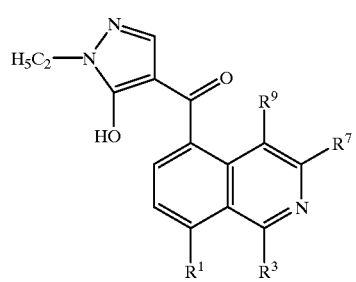

Id2 the compounds Id.3.01–Id3.91, which differ from the compounds Id1.01–Id1.91 in that $R^{15}$ is methyl:

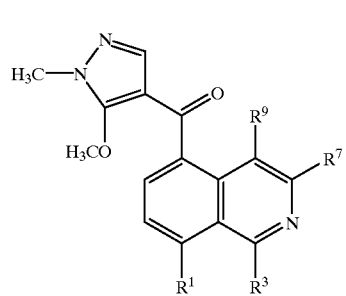

Id3 the compounds Id4.01–Id4.91, which differ from the compounds Id1.01–Id1.91 in that $R^{14}$ is ethyl and $R^{15}$ is methyl:

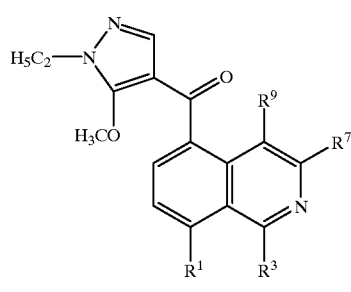

Id4 the compounds Id5.01–Id5.91, which differ from the corresponding compounds Id1.01–Id1.91 in that $R^{15}$ is ethyl:

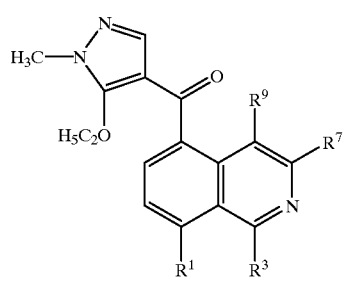

Id5 the compounds Id6.01–Id6.91, which differ from the corresponding compounds Id1.01–Id1.91 in that $R^{14}$ and $R^{15}$ are each ethyl:

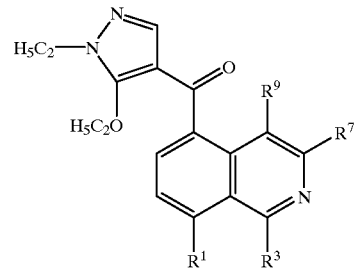

Id6 the compounds Id7.01–Id7.91, which differ from the corresponding compounds Id1.01–Id1.91 in that $R^{15}$ is n-propyl:

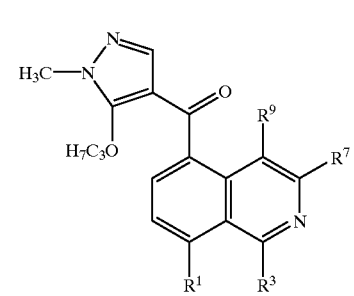

Id7 the compounds Id8.01–Id8.91, which differ from the compounds Id1.01–Id1.91 in that $R^{14}$ is ethyl and $R^{15}$ is n-propyl:

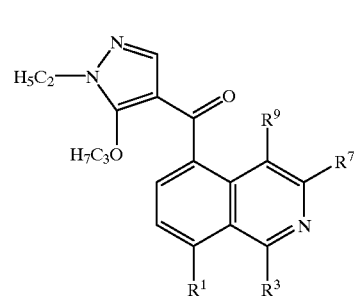

Id8 the compounds Id9.01–Id9.91, which differ from the compounds Id1.01–Id1.91 in that $R^{15}$ is n-butyl:

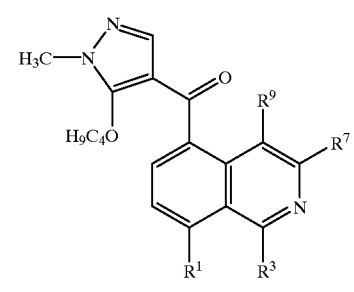

Id9 the compounds Id10.01–Id10.91, which differ from the compounds Id1.01–Id1.91 in that $R^{14}$ is ethyl and $R^{15}$ is n-butyl:

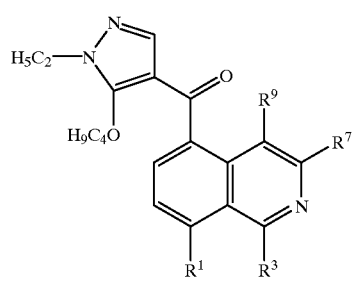

Id10 the compounds Id11.01–Id11.91, which differ from the compounds Id1.01–Id1.91 in that $R^{15}$ is methylcarbonyl:

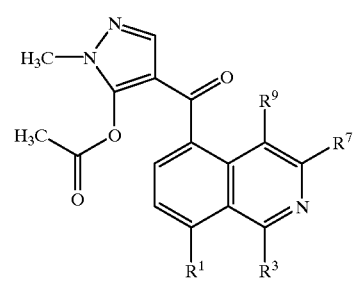

Id11 the compounds Id12.01–Id12.91, which differ from the compounds Id1.01–Id1.91 in that $R^{14}$ is ethyl and $R^{15}$ is methylcarbonyl:

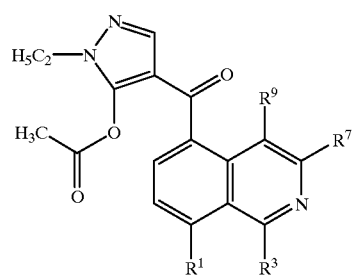

Id12 the compounds Id13.01–Id13.91, which differ from the compounds Id1.01–Id1.91 in that $R^{15}$ is ethylcarbonyl:

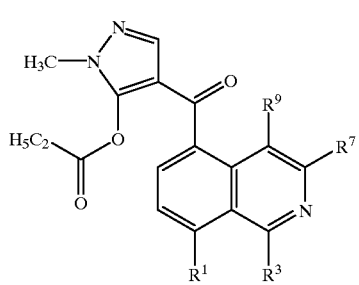

Id13 the compounds Id14.01–Id14.91, which differ from the compounds Id1.01–Id1.91 in that $R^{14}$ is ethyl and $R^{15}$ is ethylcarbonyl:

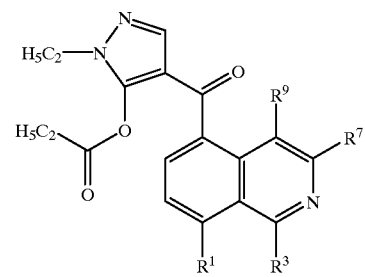

Id14 the compounds Id15.01–Id15.91, which differ from the compounds Id1.01–Id1.91 in that $R^{15}$ is n-propylcarbonyl:

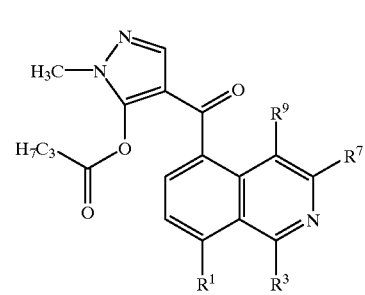

Id15 the compounds Id16.01–Id16.91, which differ from the compounds Id1.01–Id1.91 in that $R^{14}$ is ethyl and $R^{15}$ is n-propylcarbonyl:

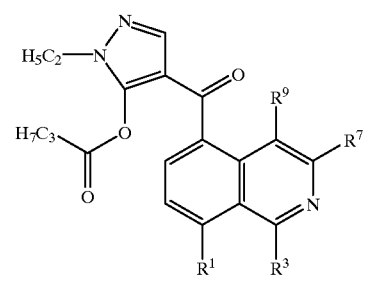

Id16 the compounds Id17.01–Id17.91, which differ from the compounds Id1.01–Id1.91 in that $R^{15}$ is n-butylcarbonyl:

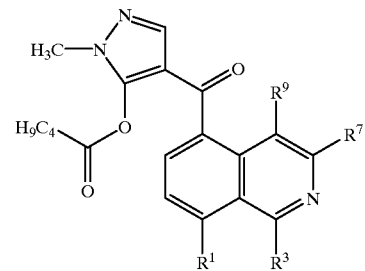

Id17 the compounds Id18.01–Id18.91, which differ from the compounds Id1.01–Id1.91 in that $R^{14}$ is ethyl and $R^{15}$ is n-butylcarbonyl:

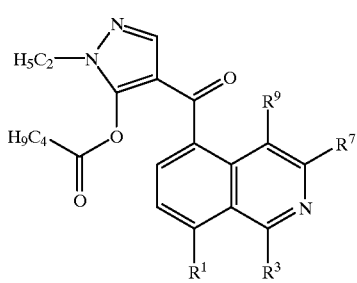

Id18

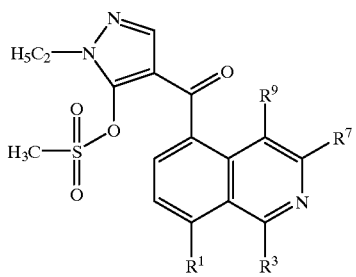

Id22 the compounds Id19.01–Id19.91, which differ from the compounds Id1.01–Id1.91 in that $R^{15}$ is trifluoromethylcarbonyl:

the compounds Id23.01–Id23.91, which differ from the compounds Id1.01–Id1.91 in that $R^{15}$ is ethylsulfonyl:

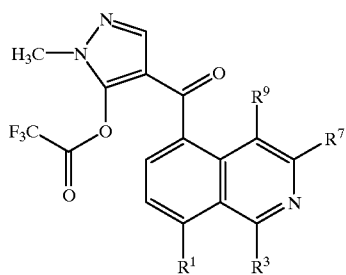

Id19

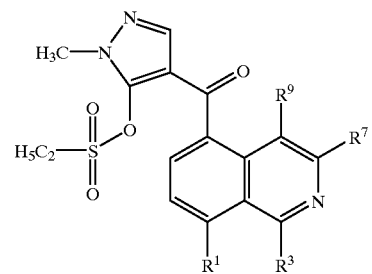

Id23 the compounds Id20.01–Id20.91, which differ from the compounds Id1.01–Id1.91 in that $R^{14}$ is ethyl and $R^{15}$ is trifluoromethylcarbonyl:

the compounds Id24.01–Id24.91, which differ from the compounds Id1.01–Id1.91 in that $R^{14}$ is ethyl and $R^{15}$ is ethylsulfonyl:

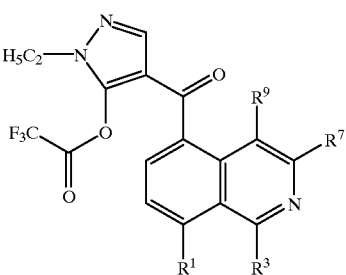

Id20

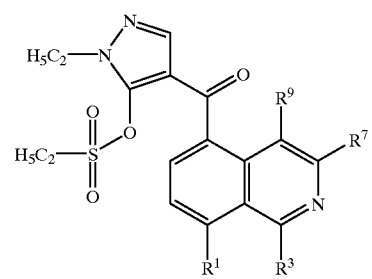

Id24 the compounds Id21.01–Id21.91, which differ from the compounds Id1.01–Id1.91 in that $R^{15}$ is methylsulfonyl:

the compounds Id25.01–Id25.91, which differ from the compounds Id1.01–Id1.91 in that $R^{15}$ is n-propylsulfonyl:

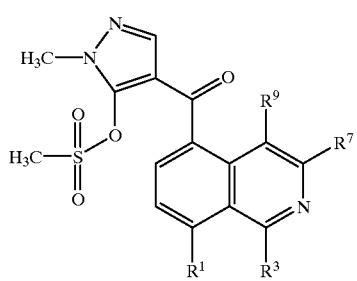

Id21

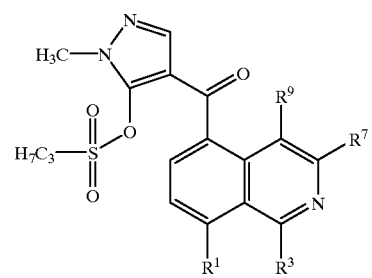

Id25 the compounds Id22.01–Id22.91, which differ from the compounds Id1.01–Id1.91 in that $R^{14}$ is ethyl and $R^{15}$ the compounds Id26.01–Id26.91, which differ from the compounds Id1.01–Id1.91 in that $R^{14}$ is ethyl and $R^{15}$ is n-propylsulfonyl:

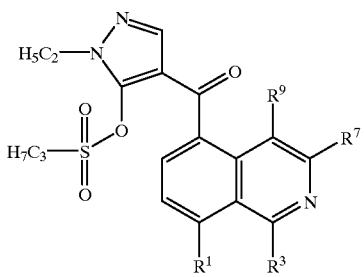
Id26 the compounds Id27.01–Id27.91, which differ from the compounds Id1.01–Id1.91 in that $R^{15}$ is n-butylsulfonyl:

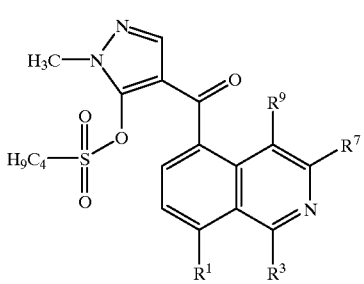
Id27 the compounds Id28.01–Id28.91, which differ from the compounds Id1.01–Id1.91 in that $R^{14}$ is ethyl and $R^{15}$ is n-butylsulfonyl:

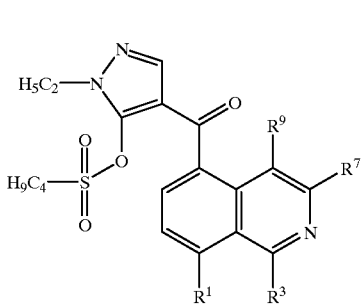
Id28 the compounds Id29.01.–Id29.91, which differ from the compounds Id1.01–Id1.91 in that $R^{15}$ is trifluoromethylsulfonyl:

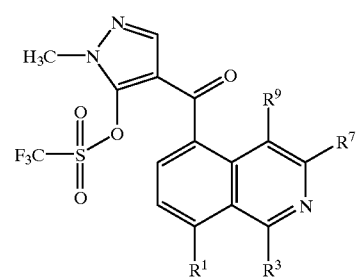
Id29 the compounds Id30.01–Id30.91, which differ from the compounds Id1.01–Id1.91 in that $R^{14}$ is ethyl and $R^{15}$ is trifluoromethylsulfonyl:

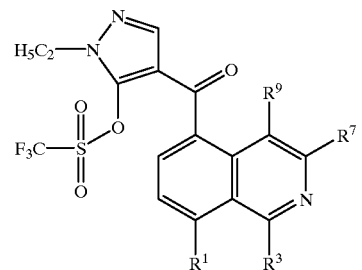
Id30 the compounds Id31.01–Id31.91, which differ from the compounds Id1.01–Id1.91 in that $R^{15}$ is phenylsulfonyl:

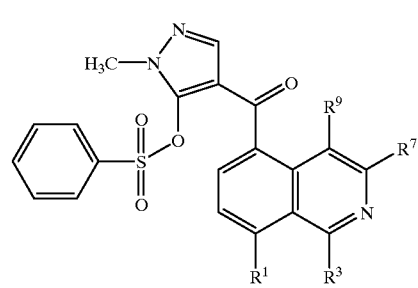
Id31 the compounds Id32.01–Id32.91, which differ from the compounds Id1.01–Id1.91 in that $R^{14}$ is ethyl and $R^{15}$ is phenylsulfonyl:

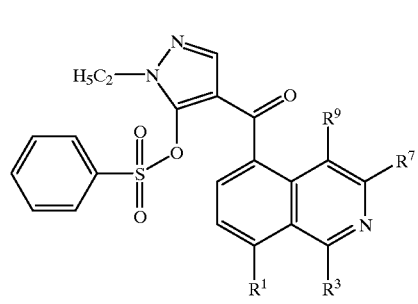
Id32 the compounds Id33.01–Id33.91, which differ from the compounds Id1.01–Id1.91 in that $R^{15}$ is 4-methylphenylsulfonyl:

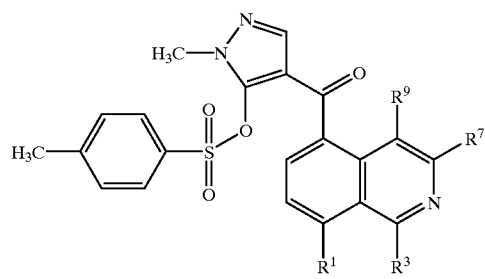
Id33 the compounds Id34.01–Id34.91, which differ from the compounds Id1.01–Id1.91 in that $R^{14}$ is ethyl and $R^{15}$ is 4-methylphenylsulfonyl:

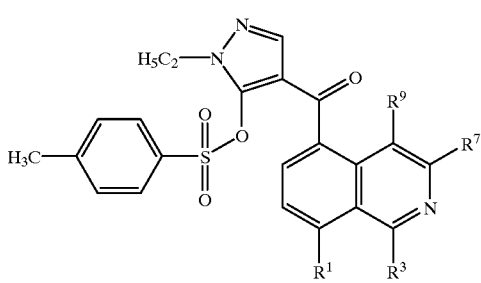

Id34 the compounds Id35.01–Id35.91, which differ from the compounds Id1.01–Id1.91 in that $R^{16}$ is methyl:

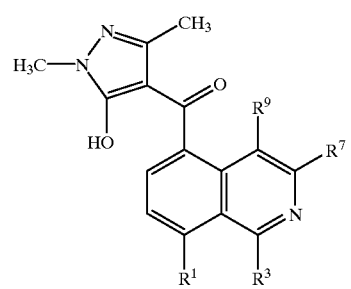

Id35 the compounds Id36.01–Id36.91, which differ from the compounds Id1.01–Id1.91 in that $R^{14}$ is ethyl and $R^{16}$ is methyl:

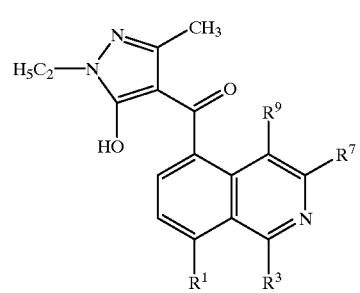

Id36 the compounds Id37.01–Id37.91, which differ from the compounds Id1.01–Id1.91 in that $R^{15}$ and $R^{16}$ are each methyl:

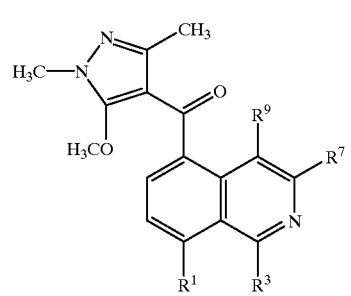

Id37 the compounds Id38.01–Id38.91, which differ from the compounds Id1.01–Id1.91 [sic] in that $R^{14}$ is ethyl, and $R^{15}$ and $R^{16}$ are each methyl:

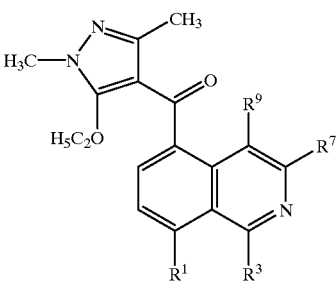

Id38 the compounds Id39.01–Id39.91, which differ from the compounds Id1.01–Id1.91 in that $R^{15}$ is ethyl and $R^{16}$ is methyl:

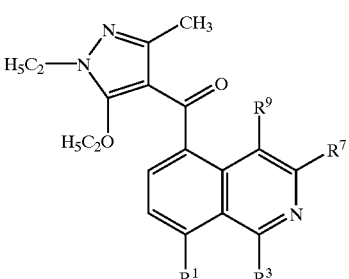

Id39 the compounds Id40.01–Id40.91, which differ from the compounds Id1.01–Id1.91 in that $R^{14}$ and $R^{15}$ are each ethyl and $R^{16}$ is methyl:

Id40

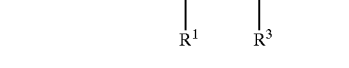

the compounds Id41.01–Id41.91, which differ from the compounds Id1.01–Id1.91 in that $R^{15}$ is n-propyl and $R^{16}$ is methyl:

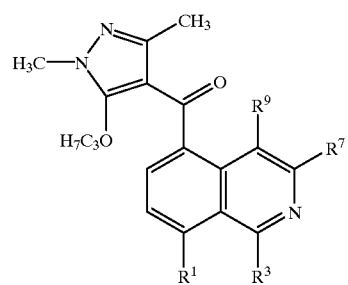

Id41 the compounds Id42.01–Id41.92, which differ from the compounds Id1.01–Id1.91 in that $R^{14}$ is ethyl, $R^{15}$ is n-propyl and $R^{16}$ is methyl:

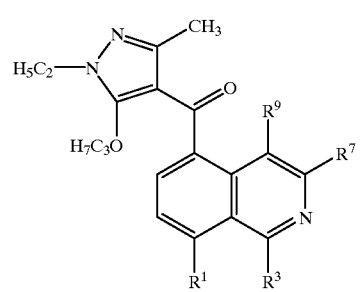

Id42 the compounds Id43.01–Id43.91, which differ from the compounds Id1.01–Id1.91 in that $R^{15}$ is n-butyl and $R^{16}$ is methyl:

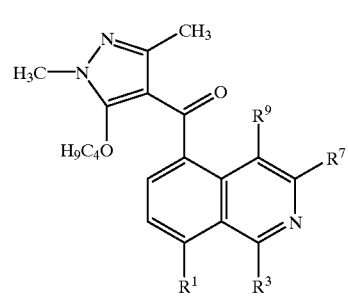

Id43 the compounds Id44.01–Id44.91, which differ from the compounds Id1.01–Id1.91 in that $R^{14}$ is ethyl, $R^{15}$ is n-butyl and $R^{16}$ is methyl:

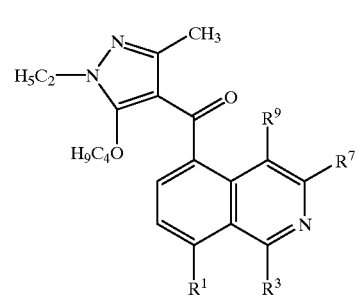

Id44 the compounds Id45.01–Id45.91, which differ from the compounds Id1.01–Id1.91 in that $R^{15}$ is methylcarbonyl and $R^{16}$ is methyl:

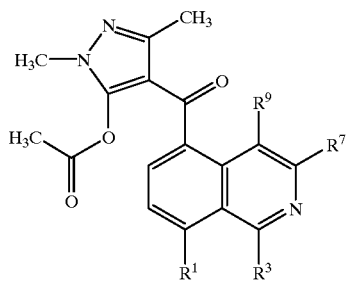

Id45 the compounds Id46.01–Id46.91, which differ from the compounds Id1.01–Id1.91 in that $R^{14}$ is ethyl, $R^{15}$ is methylcarbonyl and $R^{16}$ is methyl:

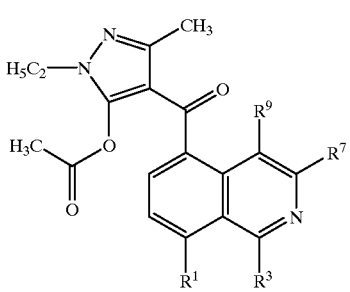

Id46 the compounds Id47.01–Id47.91, which differ from the compounds Id1.01–Id1.91 in that $R^{15}$ is ethylcarbonyl and $R^{16}$ is methyl:

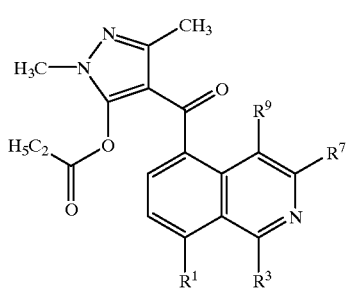

Id47 the compounds Id48.01–Id48.91, which differ from the compounds Id1.01–Id1.91 in that $R^{14}$ is ethyl, $R^{15}$ is ethylcarbonyl and $R^{16}$ is methyl:

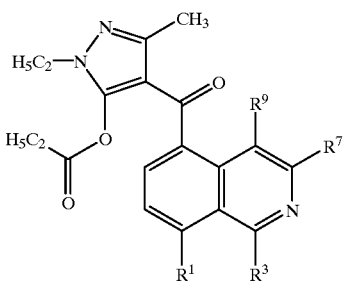

Id48 the compounds Id49.01–Id49.91, which differ from the compounds Id1.01–Id1.91 in that $R^{15}$ is n-propylcarbonyl and $R^{16}$ is methyl:

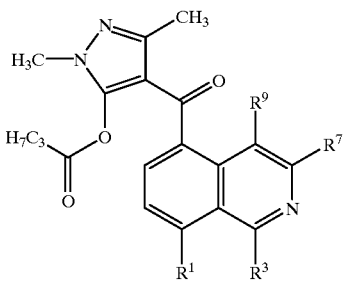

Id49 the compounds Id50.01–Id50.91, which differ from the compounds Id1.01–Id1.91 in that $R^{14}$ is ethyl, $R^{15}$ is n-propylcarbonyl and $R^{16}$ is methyl:

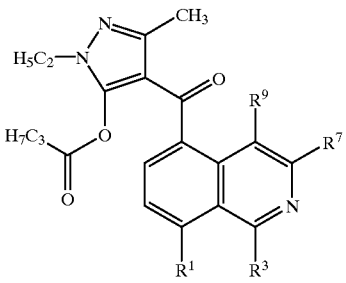

Id50 the compounds Id51.01–Id51.91, which differ from the compounds Id1.01–Id1.91 in that $R^{15}$ is n-butylcarbonyl and $R^{16}$ is methyl:

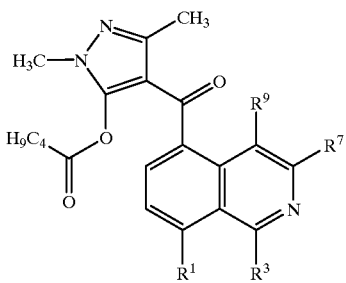

Id51 the compounds Id52.01–Id52.91, which differ from the compounds Id1.01–Id1.91 in that $R^{14}$ is ethyl, $R^{15}$ is n-butylcarbonyl and $R^{16}$ is methyl:

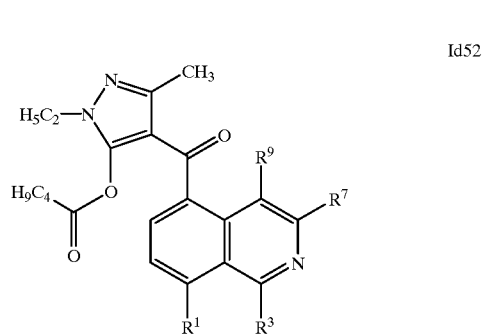

Id52 the compounds Id53.01–Id53.91, which differ from the compounds Id1.01–Id1.91 in that $R^{15}$ is trifluoromethylcarbonyl and $R^{16}$ is methyl:

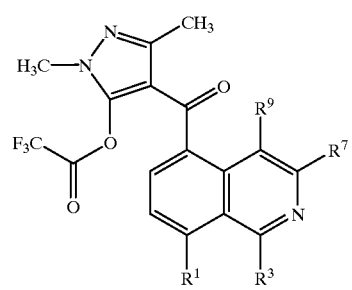

Id53 the compounds Id54.01–Id54.91, which differ from the compounds Id1.01–Id1.91 in that $R^{14}$ is ethyl, $R^{15}$ is trifluoromethylcarbonyl and $R^{16}$ is methyl:

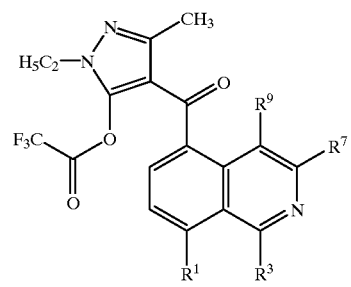

Id54 the compounds Id55.01–Id55.91, which differ from the compounds Id1.01–Id1.91 in that $R^{15}$ is methylsulfonyl and $R^{16}$ is methyl:

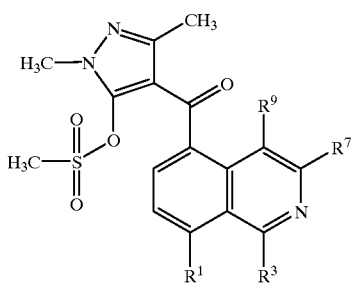

Id55 the compounds Id56.01–Id56.91, which differ from the compounds Id1.01–Id1.91 in that $R^{14}$ is ethyl, $R^{15}$ is methylsulfonyl and $R^{16}$ is methyl:

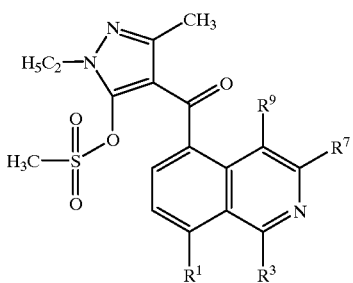

Id56 the compounds Id57.01–Id57.91, which differ from the compounds Id1.01–Id1.91 in that $R^{15}$ is ethylsulfonyl and $R^{16}$ is methyl:

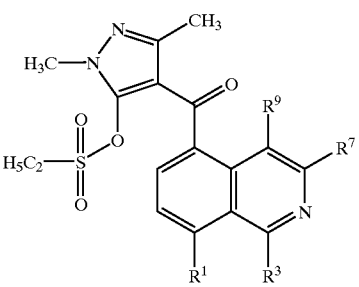

Id57 the compounds Id58.01–Id58.91, which differ from the compounds Id1.01–Id1.91 in that $R^{14}$ is ethyl, $R^{15}$ is ethylsulfonyl and $R^{16}$ is methyl:

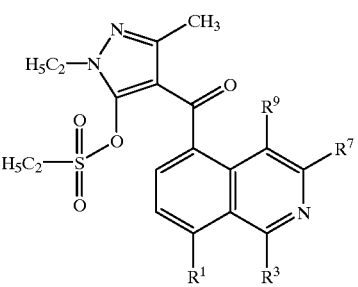

Id58 the compounds Id59.01–Id59.91, which differ from the compounds Id1.01–Id1.91 in that $R^{15}$ is n-propylsulfonyl and $R^{16}$ is methyl:

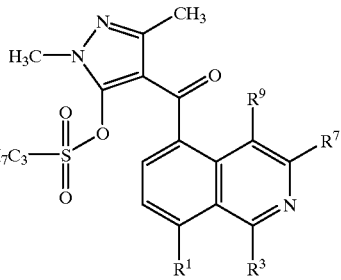

Id59 the compounds Id60.01–Id60.91, which differ from the compounds Id1.01–Id1.91 in that $R^{14}$ is ethyl, $R^{15}$ is n-propylsulfonyl and $R^{16}$ is methyl:

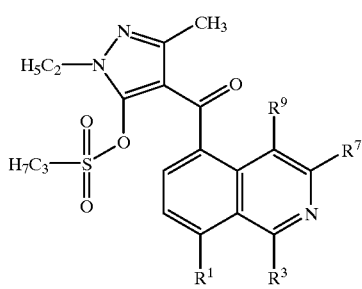

Id60 the compounds Id61.01–Id61.91, which differ from the compounds Id1.01–Id1.91 in that $R^{15}$ is n-butylsulfonyl and $R^{16}$ is methyl:

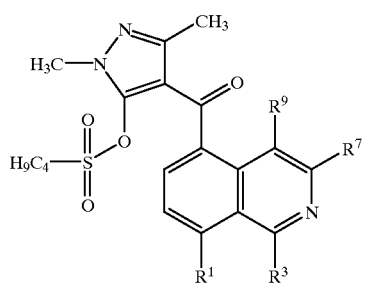

Id61 the compounds Id62.01–Id62.91, which differ from the compounds Id1.01–Id1.91 in that $R^{14}$ is ethyl, $R^{15}$ is n-butylsulfonyl and $R^{16}$ is methyl:

Id62

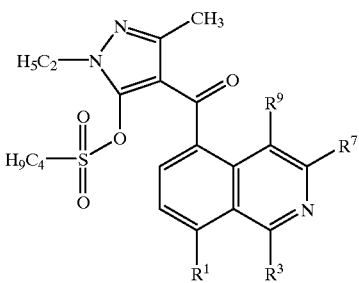

the compounds Id63.01–Id63.91, which differ from the compounds Id1.01–Id1.91 in that $R^{15}$ is trifluoromethylsulfonyl and $R^{16}$ is methyl:

Id63

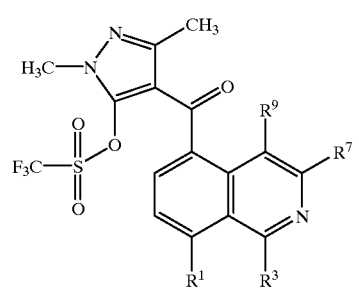

the compounds Id64.01–Id64.91, which differ from the compounds Id1.01–Id1.91 in that $R^{14}$ is ethyl, $R^{15}$ is trifluoromethylsulfonyl and $R^{16}$ is methyl:

Id64

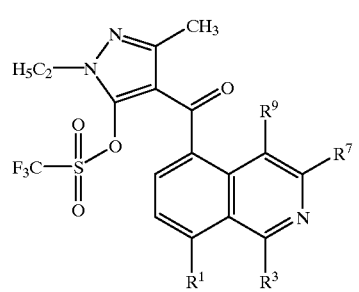

the compounds Id65.01–Id65.91, which differ from the compounds Id1.01–Id1.91 in that $R^{15}$ is phenylsulfonyl and $R^{16}$ is methyl:

Id65

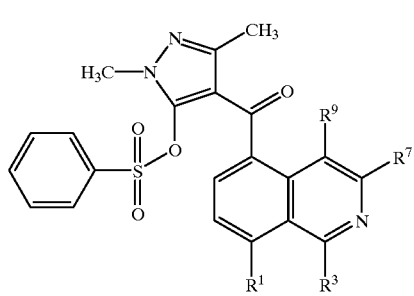

the compounds Id66.01–Id66.91, which differ from the compounds Id1.01–Id1.91 in that $R^{14}$ is ethyl, $R^{15}$ is phenylsulfonyl and $R^{16}$ is methyl:

Id66

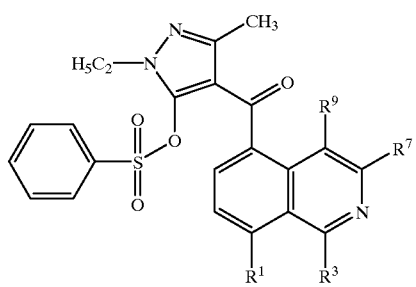

the compounds Id67.01–Id67.91, which differ from the compounds Id1.01–Id1.91 in that $R^{15}$ is 4-methylphenylsulfonyl and $R^{16}$ is methyl:

Id67

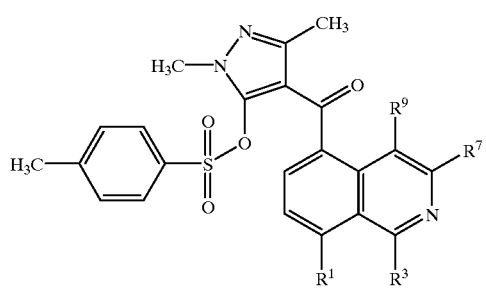

the compounds Id68.01–Id68.91, which differ from the compounds Id1.01–Id1.91 in that $R^{14}$ is ethyl, $R^{15}$ is 4-methylphenylsulfonyl and $R^{16}$ is methyl:

Id68

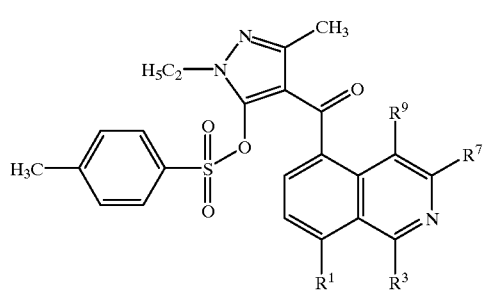

The hetaroyl derivatives of the formula I can be obtained by different routes, for example by the following process:

Process A:

Reaction of hydroxypyrazoles of the formula II where $R^{15}$=H with an activated carboxylic acid IIIa or a carboxylic acid IIIb which is preferably activated in situ to give the acylation product, and subsequent rearrangement.

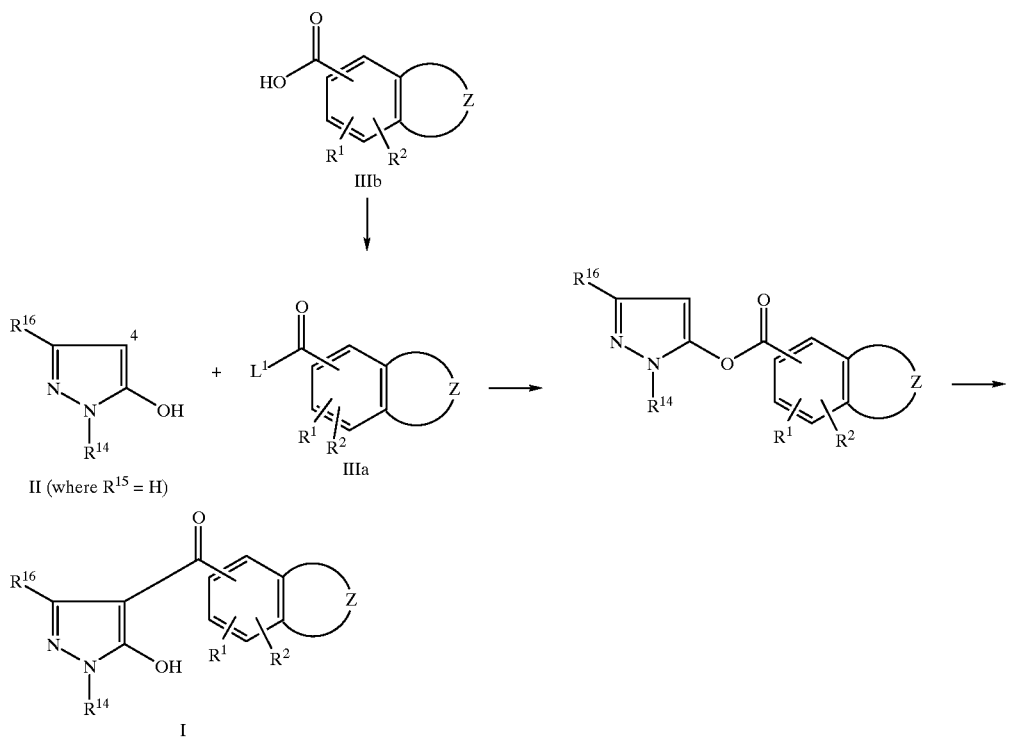

$L^1$ represents a nucleophilically replaceable leaving group, such as halogen, for example bromine or chlorine, heterocyclyl, for example imidazolyl or pyridyl, or carboxylate, for example acetate, trifluoroacetate, etc.

The activated hetaroylcarboxylic acid can be employed directly, as in the case of the hetaroyl halides, or formed in situ, for example by using dicyclohexylcarbodiimide, triphenylphosphine/azodicarboxylic ester, 2-pyridine disulfite/triphenylphosphine, carbonyldiimidazole, etc.

It may be advantageous to carry out the acylation reaction in the presence of a base. It is advantageous to employ the reactants and the auxiliary base in equimolar amounts. In certain cases, a small excess of the auxiliary base, for example 1.2 to 1.5 molar equivalents based on II, may be advantageous.

Suitable auxiliary bases include tertiary alkylamines, pyridine and alkali metal carbonates. Suitable solvents are, for example, chlorinated hydrocarbons, such as methylene chloride and 1,2-dichloroethane, aromatic hydrocarbons, such as toluene, xylene and chlorobenzene, ethers, such as diethyl ether, methyl tert-butyl ether, tetrahydrofuran and dioxane, polar aprotic solvents, such as acetonitrile, dimethylformamide or dimethyl sulfoxides or esters, such as ethyl acetate, or mixtures thereof.

If carboxylic acid halides are employed as activated carboxylic acid component, it may be advantageous to cool the reaction mixture to 0–10°0 C. when adding this reactant. Stirring is then continued at 20–100° C., preferably at 25–50° C., until the reaction has ended. Work-up is carried out in a conventional manner; for instance, the reaction mixture is poured into water and the product of value is extracted. Suitable solvents for this purpose are in particular methylene chloride, diethyl ether and ethyl acetate. After drying of the organic phase and removal of the solvent, the crude ester can be used for the rearrangement without any further purification.

The rearrangement of the esters to give the compounds of the formula I is advantageously carried out at from 20 to 40° C. in a solvent and in the presence of an auxiliary base and optionally using a cyano compound as catalyst.

Suitable solvents are, for example, acetonitrile, methylene chloride, 1,2-dichloroethane, dioxane, ethyl acetate, toluene, or mixtures thereof. Preferred solvents are acetonitrile and dioxane.

Suitable auxiliary bases are tertiary amines, such as triethylamine, pyridine or alkali metal carbonates, such as sodium carbonate and potassium carbonate, which are preferably employed in equimolar amounts or up to a fourfold excess, based on the ester. Preference is given to using triethylamine or alkali metal carbonates, preferably in double the equimolar amount based on the ester.

Suitable "rearrangement catalysts" include inorganic cyanides, such as sodium cyanide and potassium cyanide, and organic cyano compounds, such as acetone cyanohydrin and trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent based on the ester.

Work-up can be carried out in a known manner. The reaction mixture is acidified, for example with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example with sodium carbonate solution or potassium carbonate solution. The aqueous phase is acidified and the resulting precipitate is filtered off with suction and/or extracted with methylene chloride or ethyl acetate, dried and concentrated.

(Examples of the preparation of esters of hydroxypyrazoles and of the rearrangement of the esters are described, for example, in EP-A 282 944 and U.S. Pat. No. 4,643,757).

Process B:
Reaction of hetaroyl derivatives of the formula I where $R^{15}$=H with a compound of the formula IV (where $R^{15} \neq$ H):

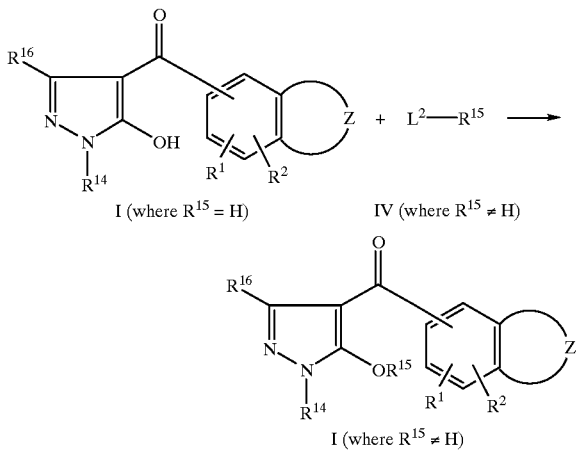

I (where $R^{15}$ = H)　　　IV (where $R^{15} \neq$ H)

I (where $R^{15} \neq$ H)

$L^2$ is a nucleophilically replaceable leaving group, such as halogen, for example bromine and chlorine, heterocyclyl, for example imidazolyl and pyridyl, carboxylate, for example acetate and trifluoroacetate, or sulfonate, for example mesylate and triflate, etc.

The compounds of the formula IV can be employed directly, for example in the case of alkyl halides, acyl halides, sulfonyl halides, carboxylic acid anhydrides and sulfonic acid anhydrides, or formed in situ, for example activated carboxylic acids (by using a carboxylic acid and dicyclohexylcarbodiimide, carbonyldiimidazole, etc.).

The starting materials are usually employed in an equimolar ratio. However, it may be advantageous to use an excess of one or other of the components.

It may be advantageous to carry out the reaction in the presence of a base. The reactants and the auxiliary base are advantageously employed in equimolar amounts. In some instances, an excess of the auxiliary base, for example 1.5 to 3 molar equivalents based on II, may be advantageous.

Suitable auxiliary bases are tertiary alkylamines, such as triethylamine or pyridine, alkali metal carbonates, for example sodium carbonate and potassium carbonate, and alkali metal hydrides, for example sodium hydride. Preference is given to triethylamine and pyridine.

Suitable solvents are, for example, chlorinated hydrocarbons, such as methylene chloride and 1,2-dichloroethane, aromatic hydrocarbons, for example toluene, xylene and chlorobenzene, ethers, such as diethyl ether, methyl tert-butyl ether, tetrahydrofuran and dioxane, polar aprotic solvents, such as acetonitrile, dimethylformamide and dimethyl sulfoxide, or esters, such as ethyl acetate, or mixtures thereof.

The reaction temperature is generally in the range of from 0° C. to the boiling point of the reaction mixture.

Work-up is carried out in a conventional manner to afford the product.

Those hydroxypyrazoles of the formula II (where $R^{15}$=H) used as starting materials which are not already known can be obtained in a conventional manner (for example EP-A 240 001, J. Prakt. Chem. 315 (1973), 383).

The carboxylic acid halides of the formula IIIa (where $L^1$=Br, Cl) which are not already known can be obtained in a conventional manner by reacting the carboxylic acids of the formula IIIb with halogenating reagents such as thionyl chloride, thionyl bromide, phosgene, diphosgene, triphosgene, oxalyl chloride and oxalyl bromide.

Those carboxylic acids of the formula IIIb which are not already known can be obtained in a conventional manner (The Chemistry of Heterocyclic Compounds, Vol. 32, "Quinolines, Part I, II and III", Editor E. Taylor, publisher Wiley & Sons; The Chemistry of Heterocyclic Compounds, Vol. 38, "Isoquinolines, Part I and II", Editor A. Weissemberger and E. Taylor, publisher Wiley & Sons; T. Eicher, S. Hauptmann, "Chemie der Heterocyclen", Thieme Verlag 1994).

For example, unsubstituted or substituted aminobenzoic acids can be reacted with glycerol, unsubstituted or substituted glycerol derivatives or α,β-unsaturated carbonyl compounds by the method of Skraup to give the corresponding quinolinecarboxylic acids (cf. EP-A 294 685, DE-A 33 26 225) (Scheme 1)

(Scheme 1)

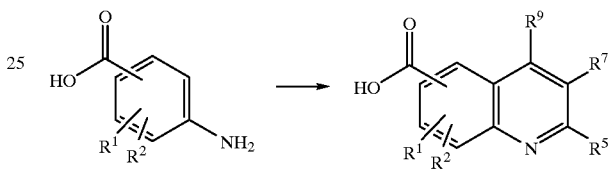

Likewise, it is possible to react unsubstituted or substituted anilines with glycerol, unsubstituted or substituted glycerol derivatives or α,β-unsaturated carbonyl compounds. After halogenation and exchange of the halogen function by cyanide (for example using copper(I) cyanide), the nitrile is hydrolyzed to give the corresponding quinolinecarboxylic acid (cf. Khim. Greterotsikl. Soedin 3 (1980), 366 (≙ CA 93, 71504)). (Scheme 2)

Scheme 2

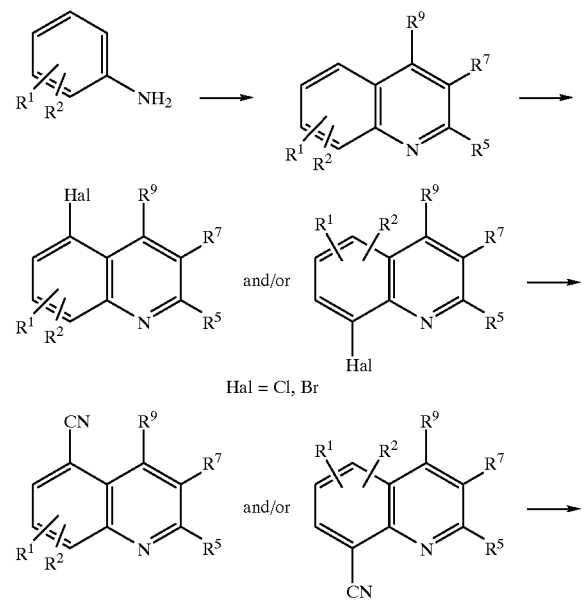

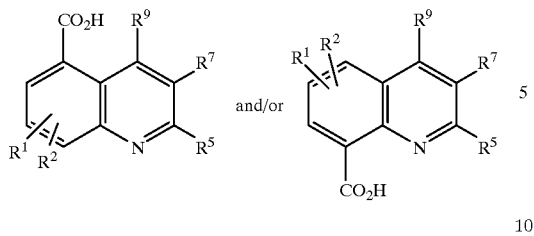

Anilines which are not already known from the literature can be obtained by reducing the corresponding nitrobenzenes. Suitable for this purpose is for example catalytic hydrogenation, using, for example, Raney nickel, Pt/C, Pd/C or Rh/C, or reduction with iron powder, zinc powder, etc. in a mixture of organic acid, for example acetic acid or propionic acid, and a protic solvent, such as methanol, ethanol or water.

The nitrobenzenes can be synthesized by nitration, substitution reactions, etc. Scheme 3 exemplifies a synthetic sequence.

Scheme 3

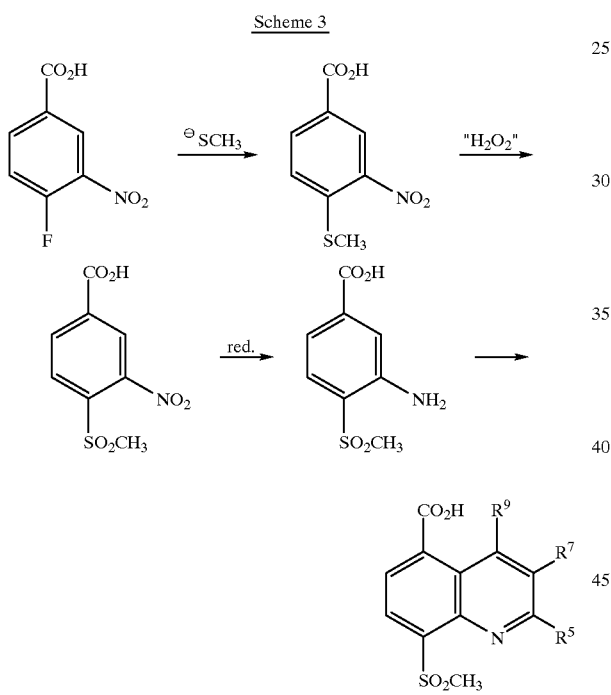

Isoquinolinecarboxylic acids can be synthesized for example from halogenated isoquinolines by halogen/cyanide exchange (Chem. Ber. 52 (1919), 1749) and subsequent hydrolysis. (Scheme 4)

Scheme 4

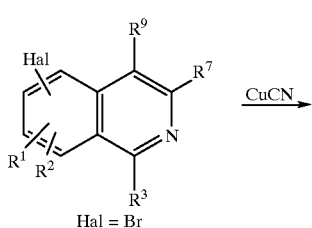

Hal = Br

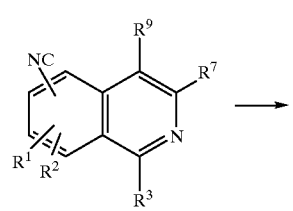

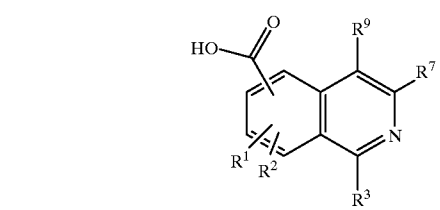

It is also possible to prepare the corresponding aminoisoquinolines from nitrated isoquinolines by reduction (as mentioned above). Subsequent diazotization, Sandmeyer reaction with cyanide and hydrolysis afford isoquinolinecarboxylic acids (Scheme 5).

Scheme 5

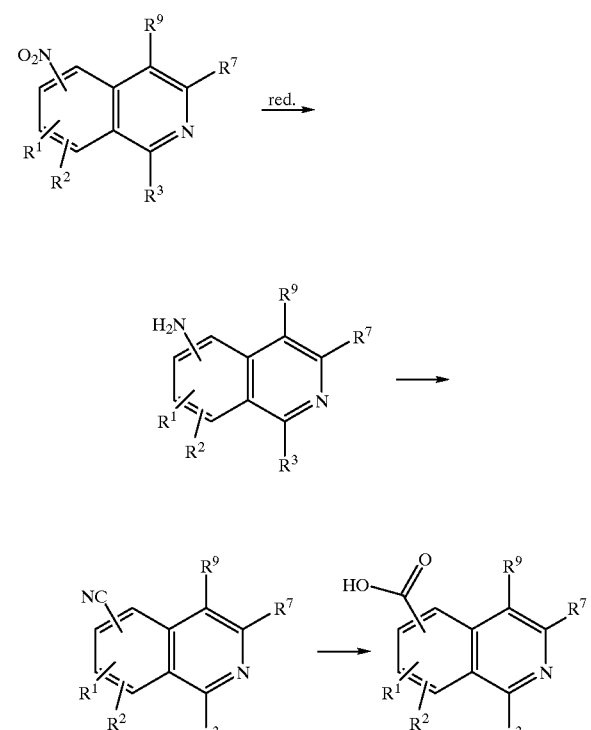

Halogenated or nitrated isoquinolines can be prepared according to EP-A 633 262. Furthermore, it is possible to obtain halogenated isoquinolines starting from unsubstituted or substituted benzaldehydes by reaction with aminoacetaldehyde acetal and subsequent halogenation (Helv. Chim. Acta 68 (1985), 1828) (Scheme 6).

Scheme 6

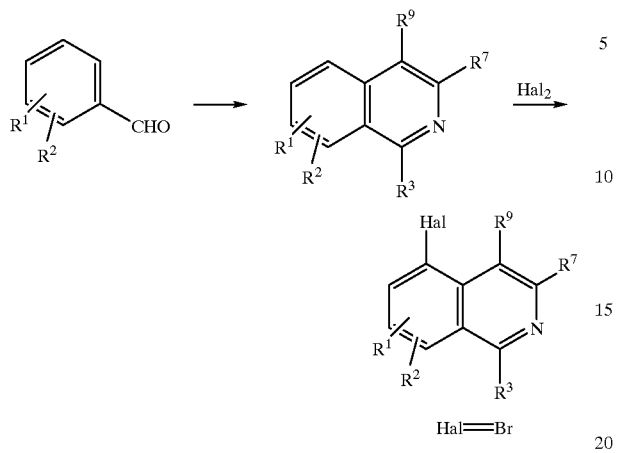

The N-oxides of the quinoline- or isoquinolinecarboxylic acids can be obtained from the corresponding quinoline- or isoquinolinecarboxylic acids by oxidation with hydrogen peroxide. It may be advantageous to convert the corresponding acids first into the $C_1$–$C_6$-alkyl esters, to carry out the oxidation with hydrogen peroxide and then hydrolyze the ester.

2,3-Dihydroquinoline derivatives can be obtained, inter alia, by cyclization of γ-functionalized N-alkylanilines, with or without using Lewis acids or protic acids (Heterocycles 24 (1986), 2109; J. Am. Chem. Soc. 71 (1949), 1901).

Tetrahydroisoquinoline derivatives can be obtained from isoquinolines by reduction with hydrogen, if appropriate by metal catalysis, for example by Pt in acetic acid. However, it is also possible to react isoquinolines with dimethyl sulfate and to convert them into tetrahydroisoquinoline derivatives by reduction with sodium borohydride.

The compounds of the formula IV which are not already known from the literature can be obtained by the methods of known processes.

Preparation Examples

4-[(8-Bromoquinolin-5-yl)carbonyl]-1-ethyl-5-hydroxypyrazole (compound 5.01)

1.00 g of 8-bromoquinoline-5-carboxylic acid, 0.44 g of 1-ethyl-5-hydroxypyrazole and 0.80 g of dicyclohexylcarbodiimide were stirred in 15 ml of acetonitrile at room temperature. After the addition of 0.2 ml of acetone cyanohydrin and 0.60 g of triethylamine, stirring was continued for 1.5 hours and the mixture was then poured into aqueous sodium carbonate solution. The alkaline phase was washed with ethyl acetate and diethyl ether and then acidified. The precipitate was filtered off under suction and the aqueous phase was extracted with ethyl acetate. This organic phase was dried and concentrated. The residue and the precipitate were combined.

Yield: 0.64 g (Melting point: 125° C.)

5-Hydroxy-1-methyl-4-[(8-methylquinolin-5-yl) carbonyl]pyrazole (compound 5.04)

Step 1: 8-methyl-5-quinolinecarbonyl chloride 10.00 g of 8-methylquinoline-5-carboxylic acid in 100 ml of toluene together with 7.00 g of thionyl chloride and 3 drops of dimethylformamide were heated under reflux for 2.5 hours. The solvent was distilled off and the acyl chloride obtained was used directly for further reactions.

Step 2: 5-hydroxy-1-methyl-4-[(8-methylquinolin-5-yl)carbonyl]-pyrazole

At 0° C., 1.70 g of 8-methylquinoline-5-carbonyl chloride were added to 0.81 g of 5-hydroxy-1-methylpyrazole and 0.92 g of triethylamine in 30 ml of acetonitrile. The reaction mixture was stirred for 3 hours at room temperature and then taken up in ethyl acetate and washed with aqueous sodium carbonate solution, and the organic phase was then dried and concentrated. The residue was treated with 10 ml of dioxane and 1.71 g of dry potassium carbonate and heated under reflux for 14 hours. After cooling, water was added and the aqueous phase was washed with ethyl acetate and acidified with 2N hydrochloric acid. The precipitate was filtered off under suction and the acidified aqueous phase was extracted with ethyl acetate. This organic phase was dried and concentrated. The residue and the precipitate were combined.

Yield: 0.97 g (Melting point: 158–160° C.)

4-[(8-Chloroquinolin-5-yl)carbonyl]-5-(4-chlorophenylsulfonyloxy)-1-ethylpyrazole (compound 5.26)

1.00 g of 4-[(8-chloroquinolin-5-yl)carbonyl]-1-ethyl-5-hydroxy-pyrazole, 0.70 g of triethylamine and 0.70 g of 4-chlorobenzenesulfonyl chloride in 15 ml of methylene chloride were stirred at room temperature for 12 hours. The reaction mixture was then poured into aqueous sodium carbonate solution and extracted with ethyl acetate. The combined organic phases were dried and concentrated and the residue was purified by chromatograpy over silica gel.

Yield: 1.00 g (Melting point: 98° C.)

In addition to the hetaroyl derivatives of the formula I described above, further hetaroyl derivatives of the formula I which have been or can be prepared in a similar manner are listed in Table 5 below:

TABLE 5

Ia (where R² = H)

| No. | R¹ | R⁵ | R⁷ | R⁹ | R¹⁴ | R¹⁵ | R¹⁶ | physical data ¹H-NMR [ppm] mp [° C.] |
|---|---|---|---|---|---|---|---|---|
| 5.01 | Br | H | H | H | n-C₂H₅ | H | H | 125 |
| 5.02 | OCH₃ | H | H | H | C₂H₅ | H | H | 58 |
| 5.03 | CH₃ | H | H | H | C₂H₅ | H | H | 104–106 |
| 5.04 | CH₃ | H | H | H | CH₃ | H | H | 158–160 |
| 5.05 | OCH₃ | H | H | H | CH₃ | H | CH₃ | 218 |
| 5.06 | Br | H | H | H | CH₃ | H | H | 176 |
| 5.07 | OCH₃ | H | H | H | CH₃ | H | H | 151 |
| 5.08 | Br | H | H | H | CH₃ | H | CH₃ | 82 |
| 5.09 | CH₃ | H | H | H | CH₃ | H | CH₃ | 57 |
| 5.10 | Cl | H | H | H | CH₃ | H | CH₃ | 87 |
| 5.11 | Cl | H | H | H | C₂H₅ | H | H | 140–142 |
| 5.12 | SO₂CH₃ | H | H | H | C₂H₅ | H | H | 159–161 |
| 5.13 | SO₂CH₃ | H | H | H | CH₃ | H | CH₃ | 148–150 |
| 5.14 | Cl | H | H | H | CH₃ | H | H | 194–197 |
| 5.15 | SO₂CH₃ | H | H | H | CH₃ | H | H | 148–150 |
| 5.16 | Cl | CH₃ | H | H | C₂H₅ | H | H | 138–140 |
| 5.17 | Cl | CH₃ | H | H | CH₃ | H | H | 217–219 |
| 5.18 | Cl | CH₃ | H | H | CH₃ | H | CH₃ | 218 |
| 5.19 | Cl | H | CH₃ | H | CH₃ | H | H | 243 |
| 5.20 | Cl | H | CH₃ | H | C₂H₅ | H | H | 134 |
| 5.21 | Cl | H | CH₃ | H | CH₃ | H | CH₃ | 117–119 |
| 5.22 | F | H | H | H | C₂H₅ | H | H | 113 |
| 5.23 | F | H | H | H | CH₃ | H | CH₃ | 249–252 |
| 5.24 | Cl | H | H | H | C₂H₅ | SO₂-C₆H₄-CH₃ (p) | H | 132 |
| 5.25 | Cl | H | H | H | C₂H₅ | SO₂—(CH₂)₃CH₃ | H | 94 |
| 5.26 | Cl | H | H | H | C₂H₅ | SO₂-C₆H₄-Cl (p) | H | 98 |
| 5.27 | SO₂CH₃ | H | H | H | i-C₄H₉ | H | H | 184 |
| 5.28 | SO₂CH₃ | H | CH₃ | H | n-C₃H₇ | H | H | 176 |
| 5.29 | SO₂CH₃ | H | CH₃ | H | CH₃ | H | H | 140 |
| 5.30 | SO₂CH₃ | H | CH₃ | H | CH₃ | H | CH₃ | 1.63(s, 3H); 2.59(s, 3H); 3.66(s, 3H); 3.70(s, 3H); 7.64(d, 1H); 8.18(d, 1H); 8.56(d, 1H); 9.00(d, 1H); |
| 5.31 | SO₂CH₃ | H | CH₃ | H | n-C₄H₉ | H | H | 159 |
| 5.32 | SO₂CH₃ | CH₃ | H | H | CH₃ | H | CH₃ | 83 |
| 5.33 | SO₂CH₃ | CH₃ | H | H | C₂H₅ | H | H | 186 |
| 5.34 | SO₂CH₃ | CH₃ | H | H | i-C₄H₉ | H | H | 1.00(d, 6H); 2.29(m, 1H); 2.82(s, 3H); 3.65(s, 3H); 3.83(d, 2H); 5.18(bs, 1H); 7.48(s, 1H); |

TABLE 5-continued

Ia (where $R^2$ = H)

[Structure: pyrazole with $R^{14}$ on N, $R^{16}$ at 3-position, $R^{15}O$ at 5-position, connected via C(=O) to quinoline at 5-position; quinoline bears $R^9$ at 4, $R^7$ at 3, $R^5$ at 2, $R^1$ at 8]

| No. | $R^1$ | $R^5$ | $R^7$ | $R^9$ | $R^{14}$ | $R^{15}$ | $R^{16}$ | physical data $^1$H-NMR [ppm] mp [° C.] |
|---|---|---|---|---|---|---|---|---|
| | | | | | | | | 7.50(d, 1H); 7.91(d, 1H); 8.61(d, 1H); 8.63(d, 1H); |
| 5.35 | $SO_2CH_3$ | $CH_3$ | H | H | n-$C_4H_9$ | H | H | 60 |
| 5.36 | $SO_2CH_3$ | $CH_3$ | H | H | n-$C_3H_7$ | H | H | 70 |
| 5.37 | Cl | $CH_3$ | $CH_3$ | H | $C_2H_5$ | H | H | 129 |
| 5.38 | Cl | H | H | H | $C_2H_5$ | CO-n-$C_3H_7$ | H | 85 |
| 5.39 | Cl | H | H | H | $C_2H_5$ | CO-phenyl | H | 166 |
| 5.40 | Br | H | H | H | $C_2H_5$ | CO-n-$C_3H_7$ | H | 82 |
| 5.41 | Br | H | H | H | $C_2H_5$ | $SO_2$-(4-CH$_3$-phenyl) | H | 132 |
| 5.42 | Cl | H | H | H | $C_2H_5$ | $CH_2$-phenyl | H | 106 |
| 5.43 | Br | H | H | H | $C_2H_5$ | $CH_3$ | H | 120 |
| 5.44 | Cl | H | H | H | $C_2H_5$ | CO—O-n-$C_3H_7$ | H | 85 |
| 5.45 | Cl | H | H | H | $C_2H_5$ | CO—$CH_3$ | H | 153 |
| 5.46 | Br | H | H | H | $C_2H_5$ | $C_2H_5$ | H | 123 |
| 5.47 | Br | H | H | H | $C_2H_5$ | $CH_2$-phenyl | H | 79 |
| 5.48 | Br | H | H | H | $C_2H_5$ | $CH_3$ | H | 117 |
| 5.49 | Br | H | H | H | $C_2H_5$ | CO-phenyl | H | 154 |
| 5.50 | Cl | H | H | H | $C_2H_5$ | $C_2H_5$ | H | 130 |
| 5.51 | Cl | H | H | H | $C_2H_5$ | $CH_2CO$-phenyl | H | 148 |
| 5.52 | Br | H | H | H | $C_2H_5$ | CO—O-n-$C_3H_7$ | H | 1.00(t, 3H); 1.50(m, 3H); 1.78(m, 2H); 4.17(m, 4H); 7.52(m, 1H); |

TABLE 5-continued

Ia (where $R^2$ = H)

[Structure: pyrazole with $R^{14}$-N, N-$R^{16}$, $R^{15}$O, connected via C=O to quinoline with $R^9$, $R^7$, $R^5$, $R^1$ substituents]

| No. | $R^1$ | $R^5$ | $R^7$ | $R^9$ | $R^{14}$ | $R^{15}$ | $R^{16}$ | physical data $^1$H-NMR [ppm] mp [° C.] |
|---|---|---|---|---|---|---|---|---|
| 5.53 | Br | H | H | H | $C_2H_5$ | $CH_2CO$—[phenyl] | H | 7.67(m, 2H); 8.15(m, 1H); 8.62(m, 1H); 9.08(m, 1H); 137 |
| 5.54 | Br | H | H | H | $C_2H_5$ | CO-$CH_3$ | H | 154 |

The syntheses of some carboxylic acids of the formula IIIb are listed below:

8-Methylsulfonyl-5-quinolinecarboxylic acid (Compound 6.06)

Step 1: 3-Nitro-4-(methylthio)benzoic acid 0.75 mol of 4-fluoro-3-nitrobenzoic acid was charged in 2 l of methanol, and 0.75 mol of sodium methoxide was added dropwise. 0.83 mol of sodium thiomethoxide was then added and the reaction mixture was heated to 55–60° C. for 5 hours. After cooling, 1 l of water was added, the precipitate was filtered off with suction and washed with 100 ml of methylene chloride. The residue was then taken up in 500 ml of 2 N hydrochloric acid and the precipitate formed was filtered off with suction and washed with water. The residue was then taken up in tetrahydrofuran and dried over sodium sulfate and the solvent was distilled off.

Yield: 127.6 g (79%) (yellow solid)
(Melting point: 245–247° C.)

Step 2: 3-Nitro-4-methylsulfonylbenzoic acid 0.22 mol of 3-nitro-4-(methylthio)benzoic acid was charged together with 800 ml of glacial acetic acid and 5.4 g of $Na_2WO_4 \cdot 2 H_2O$. At a temperature of 55° C., 1.32 mol of $H_2O_2$ (30% strength) were added dropwise. The mixture was then stirred for 20 minutes at 50° C. and for 2 hours at 70° C. After cooling, the reaction solution was stirred into 1 l of water, the precipitate was filtered off with suction, the residue was washed with water and the product was dried under reduced pressure.

Yield: 47.4 g (88%) (white crystals)
(IR (υ in cm$^{-1}$): 1699, 1558, 1371, 1322, 1155)

Step 3: 3-Amino-4-methylsulfonylbenzoic acid 0.447 mol of 3-nitro-4-methylsulfonylbenzoic acid was reduced with hydrogen by employing 100 g of Raney nickel in 2.5 l of methanol. The mixture was then heated to reflux and filtered off hot with suction. The filtrate was concentrated.

Yield: 88.1 g (91%)
($^1$H—NMR (d$_6$-DMSO, δ in ppm): 3.18 (3H); 6.25 (2H); 7.21 (1H); 7.48 (1H); 7.72 (1H); 13.8 (1H))

Step 4: 8-Methylsulfonyl-5-quinolinecarboxylic acid 38 ml of water and 102 g of concentrated sulfuric acid were heated to 110° C. At 95° C., 0.25 mol of 3-amino-4-methylsulfonylbenzoic acid was added. The mixture was then heated to 140° C., and 0.8 g of sodium iodide and 0.3 mol of glycerol were added. The reaction temperature was then increased to 150° C. While the mixture was heated to and stirred at 150° C. (1 hour), 47 g of distillate were collected. After cooling, the reaction mixture was carefully admixed with 200 ml of water and diluted with a further 800 ml of water. Using 20% strength aqueous sodium hydroxide solution, the pH was adjusted to 13 and the mixture was filtered and adjusted to pH 3.5 with sulfuric acid. This procedure was repeated. A precipitate was formed which was filtered off with suction. The filtrate was adjusted to pH=2 and the resulting precipitate was filtered off with suction, washed with water and dried.

Yield: 44.9 g (71%)
($^1$H—NMR (d$_6$-DMSO, δ in ppm): 3.70 (3H); 7.82 (1H); 8.40 (1B); 8.68 (1H); 9.32 (1H); 9.66 (1H), 14.01 (1H))

8-Bromoquinoline-5-carboxylic acid (Compound 6.05)

Step 1: 5-Amino-8-bromoquinoline

At reflux, 10.0 g of 8-bromo-5-nitroquinoline in 68 ml of glacial acetic acid and 34 ml of ethanol were added dropwise to a mixture of 7.75 g of iron powder, 18 ml of glacial acetic acid and 9 ml of ethanol. After stirring for 45 minutes at reflux, the mixture was cooled and filtered through diatomaceous earth. The filtrate was concentrated, taken up in methylene chloride, washed with sodium carbonate solution, dried and concentrated.

Yield: 7.90 g ($^1$H—NMR (CDCl$_3$; δ in ppm): 4.22 (bs, 2H); 7.71 (m,1H); 7.40 (m,1H); 7.80 (m,1H); 8.18 (m,1H); 9.00 (m,1H))

Step 2: 8-Bromo-5-cyanoquinoline 0.60 g of concentrated hydrochloric acid was added dropwise to a mixture of 0.70 g of 5-amino-8-bromoquinoline and 3.15 ml of acetic acid, and the mixture was stirred for 1 hour at room temperature. At 0–50° C., 0.22 g of sodium nitrite in 0.45 ml of water were then added, and the mixture was stirred for 1 hour. After the addition of 20 mg of urea in 0.16 ml of water, stirring was continued at 0–50° C. for a further hour. This solution is added to a two-phase system of toluene/copper(I) cyanide solution which was prepared as follows: a solution of 0.79 g of copper(II) sulfate in 2.2 ml of water was added dropwise to a solution of 1.06 g of 10% strength ammonia solution and 0.77 g of sodium cyanide, and 6 ml of toluene were added to this mixture to form a lower layer. After stirring for 1 hour at room temperature, insoluble particles were filtered off and the solution was extracted with ethyl acetate. The organic phase was dried and the solvent was removed under reduced pressure.

Yield: 0.50 g ($^1$H—NMR (CDCl$_3$; δ in ppm): 7.61 (m,1H); 7.76 (m,1H); 8.19 (m,1H); 8.59 (m,1H); 9.17 (m,1H))

Step 3: 8-Bromoquinoline-5-carboxylic acid

At 150° C., 5.0 g of 8-bromo-5-cyanoquinoline were added a little at a time to 10.10 g of 75% strength sulfuric acid. After one hour, the reaction mixture was cooled, poured into ice water and extracted with ethyl acetate. The organic phase was dried and concentrated.

Yield: 3.6 g ($^1$H—NMR (d$_6$-DMSO; δ a in ppm): 7.80 (m,1H); 8.18 (m,1H); 8.30 (m,1H); 9.15 (m,1H); 9.40 (m,1H))

5-Nitroquinoline-6-carboxylic acid (Compound 7.01)

Step 1: 5-Nitro-6-methylquinoline 2.45 mol of 6-methylquinoline were added to 1 l of concentrated sulfuric acid, and 2.94 mol of 65% strength nitric acid were added dropwise at 0 to 10° C. The mixture was stirred for 1 hour, poured onto ice, adjusted to pH 2.5 with aqueous sodium hydroxide solution, filtered off with suction, washed with water and dried over magnesium sulfate.

Yield: 313.0 g of colorless crystals ($^1$H—NMR (CDCl$_3$; δ in ppm): 2.55 (s,3H); 7.55 (q,1H); 7.60 (d,1H); 8.10 (d,1H); 8.15 (d,1H); 8.95 (q,1H))

Step 2: 5-Nitroquinoline-6-carboxylic acid 20.0 g of vanadium pentoxide and 0.74 mol of 5-nitro-6-methylquinoline were added to 1.3 l of sulfuric acid, and 200 ml of 65% strength nitric acid are metered in at 140° C. over a period of 40 hours using a metering pump. The solution was subsequently poured onto ice, adjusted to pH 8.0 using aqueous sodium hydroxide solution, filtered off with suction and dried over magnesium sulfate. 81.0 g of starting material was recovered. The mother liquor was adjusted to pH 2.5 with sulfuric acid, filtered off with suction and dried over magnesium sulfate.

Yield: 67.0 g of colorless crystals ($^1$H—NMR (d$_6$-DMSO; δ in ppm): 7.80 (q,1H); 8.20 (d,1H); 8.25 (d,1H); 8.40 (d,1H); 9.20 (d,1H))

5-Nitroquinoline-8-carboxylic acid (Compound 9.03)

Step 1: 8-Cyano-5-nitroquinoline 5.80 g of 8-bromo-5-nitroquinoline and 2.00 g of copper (I) cyanide in 15 ml of dimethylformamide were heated to 150° C. for 5 hours. After cooling, methylene chloride was added, insoluble particles were filtered off and the filtrate was concentrated.

Yield: 3.90 g ($^1$H—NMR (CDCl$_3$; δ in ppm): 7.84 (m,1H); 8.37 (m,1H); 8.40 (m,1H); 9.00 (m,1H); 9.24 (m,1H))

Step 2: 5-Nitroquinoline-8-carboxylic acid

At 150° C., 1.50 g of 8-cyano-5-nitroquinoline were added a little at a time to 3.50 g of 75% strength sulfuric acid. After stirring for one hour, the reaction mixture was cooled, poured into ice water and extracted with ethyl acetate. The organic phase was dried and the solvent was removed under reduced pressure.

Yield: 1.1 g (Melting point: 210° C.)

($^1$H—NMR (d$_6$-DMSO; δ in ppm): 8.00 (m,1H); 8.49 (m,1H); 8.58 (m,1H); 9.01 (m,1H); 9.22 (m,1H); 15.0 (bs, 1H))

1-Acetyl-2,3-dihydro-4-quinolone-7-carboxylic acid (Compound 11.02)

Step 1: N-(2-Cyanoethyl)-3-aminobenzoic acid 200.0 g of 3-aminobenzoic acid in 2 l of water were admixed with 53.2 g of sodium hydroxide. At 30° C., 126.6 g of acrylonitrile were added dropwise, and the mixture was then heated under reflux for 22 hours. The mixture was then cooled to 5° C. and acetic acid was added (pH=5) and the precipitate which had formed was filtered off with suction and washed with water.

Yield: 266.3 g ($^1$H—NMR (d$_6$-DMSO; δ in ppm): 2.75 (2H); 3.38 (2H); 6.21 (1H); 6.87 (1H); 7.21 (2H); 12.70 (1H))

Step 2: N-(2-Carboxyethyl)-3-aminobenzoic acid 266.0 g of N-(2-cyanoethyl)-3-aminobenzoic acid together with 336.0 g of sodium hydroxide in 3 l of water were heated under reflux for 5 hours. After cooling, the pH was adjusted to 3 with hydrochloric acid, the mixture was cooled and the precipitate was filtered off with suction.

Yield: 269.2 g (Melting point: 211° C.)

Step 3: 2,3-Dihydro-4-quinolone-7-carboxylic acid

At 110° C., 50.0 g of the carboxylic acid of Step 2 were added a little at a time to 500.0 g of polyphosphoric acid. Stirring was continued for 1 hour. The reaction mixture was then poured onto ice, the precipitate was separated off and the mixture was extracted with ethyl acetate. The organic phase was then dried and concentrated.

Yield: 9.2 g ($^1$H—NMR (d$_6$-DMSO; δ in ppm): 2.52 (2H); 3.41 (2H); 7.05 (2H); 7.40 (1H); 7.65 (1H))

Step 4: 1-Acetyl-2,3-dihydro-4-quinolone-7-carboxylic acid 5.0 g of 2,3-dihydro-4-quinolone-7-carboxylic acid and 22.5 g of acetic anhydride were heated to 100° C. for 1 hour. After cooling, water was added and the mixture was extracted with methylene chloride. The organic phase was dried and concentrated.

Yield: 4.8 g (Melting point: 150° C.)

1,8-Dimethyl-1,2,3,4-tetrahydroquinoline-5-carboxylic acid (Compound 13.01)

Step 1: 8-Methyl-1,2,3,4-tetrahydroquinoline-5-carboxylic acid 0.1 mol of 8-methylquinoline-5-carboxylic acid was suspended in 1.5 l of ethanol and admixed with 10.0 g of palladium on activated carbon (5%). Over a period of 48 hours, the mixture was reduced in an autoclave at 50° C. using hydrogen (1 bar) (HPLC control). The reaction mixture was then filtered, the filter cake was washed with ethanol and the combined organic filtrates were concentrated.

Yield: 17.4 g of a yellow solid ($^1$H—NMR (d$_6$-DMSO; δ in ppm): 1.75 (m,2H); 2.05 (s,3H); 2.90 (m,2H); 3.25 (m,2H); 5.10 (brs,2H); 6.80 (d,1H); 6.90 (d,1H))

(Melting point: 130° C.)

Step 2: 1,8-Dimethyl-1,2,3,4-tetrahydroquinoline-5-carboxylic acid 24 mmol of sodium cyanoborohydride were added to 5 mmol of 8-methyl-1,2,3,4-tetrahydroquinoline-5-carboxylic acid and 50 mmol of paraformaldehyde in 30 ml of glacial acetic acid, the temperature being kept below 30° C. using an ice bath. The mixture was stirred at room temperature for 15 hours and then poured onto ice and adjusted to pH 4 using aqueous sodium hydroxide solution. The mixture was then extracted with ethyl acetate and the organic phase was washed with water, dried over sodium sulfate and concentrated.

Yield: 0.75 g of colorless crystals ($^1$H—NMR (d$_6$-DMSO; δ in ppm): 1.75 (m,2H); 2.25 (s,3H); 2.65 (s,3H); 3.00 (m,4H); 7.05 (d,1H); 7.30 (d,1H)

In addition to the carboxylic acids of the formula IIIb described above, further carboxylic acids of the formula IIIb which were or can be prepared in a similar manner are listed in Tables 6–12 below:

TABLE 6

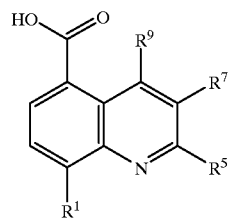

IIIb

| No. | $R^1$ | $R^5$ | $R^7$ | $R^9$ | physical data $^1$H-NMR [ppm]; mp [° C.] |
|---|---|---|---|---|---|
| 6.01 | F | H | H | H | 7.66(m, 1H); 7.80(m, 1H); 8.30 (m, 1H); 9.01(m, 1H); 9.55 (m, 1H); |
| 6.02 | Cl | H | H | H | 7.80(m, 1H); 8.09(m, 1H); 8.25 (m, 1H); 9.10(m, 1H); 9.41(m, 1H); 13.1(bs, 1H); |
| 6.03 | Cl | H | CH$_3$ | H | 2.56(s, 3H); 7.91(m, 1H); 8.15 (m, 1H); 8.96(m, 1H); 9.16(m, 1H); 13.1(bs, 1H); |
| 6.04 | Cl | CH$_3$ | H | H | 2,73(s, 3H); 7.49(m, 1H); 7.65 (m, 1H); 8.14(m, 1H); 9.23(m, 1H); 13.1(bs, 1H); |
| 6.05 | Br | H | H | H | 7.80(m, 1H); 8.18(m, 1H); 8.30 (m, 1H); 9.15(m, 1H); 9.40(m, 1H); |
| 6.06 | SO$_2$CH$_3$ | H | H | H | 3.70(s, 3H); 7.82(m, 1H); 8.40 (m, 1H); 8.68(m, 1H); 9.32(m, 1H); 9.66(m, 1H); 14.01(bs, 1H); |
| 6.07 | SO$_2$CH$_3$ | H | CH$_3$ | H | 2.60(s, 3H); 3.63(s, 3H); 8.26 (m, 1H); 8.40(m, 1H); 9.10(m, 1H); 9.14(m, 1H); |
| 6.08 | SO$_2$CH$_3$ | CH$_3$ | H | H | 2.80(m, 3H); 3.66(s, 3H); 7.70 (m, 1H); 8.28(m, 1H); 8.45(m, 1H); 9.16(m, 1H); |
| 6.09 | CH$_3$ | H | H | H | 290 |
| 6.10 | OH | H | H | H | 7.39(m, 1H); 7.90(m, 1H); 8.33 (m, 1H); 8.89(m, 1H); 9.70 (m, 1H); |
| 6.11 | OCH$_3$ | H | H | H | 4.04(s, 3H); 7.33(m, 1H); 7.68 (m, 1H); 8.31(m, 1H); 8.90(m, 1H); 9.60(m, 1H); |

TABLE 7

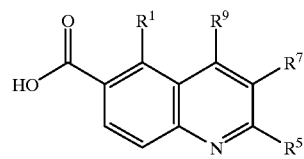

IIIb

| No. | $R^1$ | $R^5$ | $R^7$ | $R^9$ | physical data $^1$H-NMR [ppm] |
|---|---|---|---|---|---|
| 7.01 | NO$_2$ | H | H | H | 7.80(q, 1H); 8.20(d, 1H); 8.25(d, 1H); 8.40(d, 1H); 9.20(d, 1H) |
| 7.02 | Cl | H | H | H | |
| 7.03 | Br | H | H | H | |

TABLE 8

IIIb

| No. | R¹ | R⁵ | R⁷ | R⁹ | physical data ¹H-NMR [ppm] |
|---|---|---|---|---|---|
| 8.01 | $CH_3$ | H | H | H | 3.01(s, 3H); 7.64(m, 1H); 7.93(m, 1H); 8.42(m, 2H); 9.01(m, 1H); 13.30(bs, 1H); |

TABLE 9

IIIb

| No. | R¹ | R⁵ | R⁷ | R⁹ | physical data mp [° C.] |
|---|---|---|---|---|---|
| 9.01 | Cl | H | H | H | 199 |
| 9.02 | $SO_2CH_3$ | H | H | H | 231 |
| 9.03 | $NO_2$ | H | H | H | 210 |
| 9.04 | H | H | H | H | 177 |

TABLE 10

IIIb

| No. | R¹ | R⁵ | R⁷ | R⁹ | physical data ¹H-NMR [ppm] |
|---|---|---|---|---|---|
| 10.01 | $NO_2$ | H | H | H | |
| 10.02 | Cl | H | H | H | |

TABLE 11

IIIb

| No. | R¹ | R¹¹ | physical data ¹H-NMR [ppm]; mp [° C.] |
|---|---|---|---|
| 11.01 | H | H | 2.52(m, 2H); 3.42(m, 2H); 7.10(m, 1H); 7.37(m, 1H); 7.61(m, 1H); 12.8(s, 1H); |
| 11.02 | H | $COCH_3$ | 150 |
| 11.03 | $CH_3$ | $COCH_3$ | 2.20(s, 3H); 2.48(m, 2H); 2.70(s, 3H); 3.11(m, 1H); 3.86(m, 1H); 4.39(m, 1H); 7.61(m, 1H); 7.79(m, 1H); 12.80(bs, 1H); |

TABLE 12

IIIb

| No. | R¹ | R¹¹ | physical data ¹H-NMR [ppm] |
|---|---|---|---|
| 12.01 | H | $COCH_3$ | 2.36(s, 3H); 2.85(m, 2H); 4.17(m, 2H); 7.89(m, 1H); 8.09(m, 1H); 8.40(m, 1H); 13.1(bs, 1H); |

TABLE 13

IIIb

| No. | R¹ | R¹¹ | physical data ¹H-NMR [ppm]; mp [° C.] |
|---|---|---|---|
| 13.01 | $CH_3$ | $CH_3$ | 1.75(m, 2H); 2.25(s, 3H); 2.65(s, 3H); 3.00(m, 4H); 7.05(d, 1H); 7.30(d, 1H) |
| 13.02 | F | $CH_3$ | |
| 13.03 | $CH_3$ | $CH_3CO$ | 182 |
| 13.04 | F | $CH_3CO$ | |

The compounds of the formula I and their agriculturally useful salts are suitable as herbicides, both in the form of isomer mixtures and in the form of the pure isomers. The herbicidal compositions comprising compounds of the formula I are capable of controlling vegetation on non-crop areas very efficiently, especially at high application rates. In crops such as wheat, rice, maize, soya and cotton, they act against broad-leaved weeds and grass weeds without causing any significant damage to the crop plants. This effect is observed mainly at low application rates.

Depending on the application method employed, the compounds of the formula I, or the herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (s. vulgare), *Theobroma cacao, Trifolium pratense, Triticum aestivum, Triticum durum, Vicia faba, Vitis vinifera* and *Zea mays*.

In addition, the compounds of the formula I can also be used in crops which tolerate the action of herbicides owing to breeding including genetic engineering methods.

The compounds of the formula I, or the herbicidal compositions comprising them, can be used for example in the form of directly sprayable aqueous solutions, powders, suspensions, also highly concentrated aqueous, oily or other suspensions or dispersions, emulsions, oil dispersions, pastes, dusts, materials for spreading or granules by means of spraying, atomizing, dusting, spreading or watering. The use forms depend on the intended purposes; in any case, they should ensure the finest possible distribution of the active ingredients according to the invention.

Suitable inert auxiliaries are essentially: mineral oil fractions of medium to high boiling point, such as kerosine or diesel oil, further coal tar oils and oils of vegetable or animal origin, aliphatic, cyclic and aromatic hydrocarbons, eg. paraffins, tetrahydronaphthalene, alkylated naphthalenes or their derivatives and alkylated benzenes or their derivatives, alcohols, such as methanol, ethanol, propanol, butanol and cyclohexanol, ketones, such as cyclohexanone, or strongly polar solvents, eg. amines, such as N-methylpyrrolidone, or water.

Aqueous use forms can be prepared from emulsion concentrates, suspensions, pastes, wettable powders or water-dispersible granules by adding water. To prepare emulsions, pastes or oil dispersions, the substrates [sic], as such or dissolved in an oil or solvent, can be homogenized in water by means of a wetting agent, tackifier, dispersant or emulsifier. Alternatively, it is possible to prepare concentrates composed of active substance, wetting agent, tackifier, dispersant or emulsifier and, if desired, solvent or oil, these concentrates being suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and the salts of sulfated hexa-, hepta- and octadecanols and of fatty alcohol glycol ether, condensates of sulfonated naphthalene and its derivatives with formaldehyde, condensates of naphthalene, or of naphthalenesulfonic acids, with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active substances together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active ingredients of the formula I in the ready-to-use preparations can be varied within wide ranges. In general, the formulations comprise, for instance, from 0.001 to 98% by weight, preferably 0.01 to 95% by weight, of at least one active ingredient. The active ingredients are employed in a purity of from 90% to 100%, preferably 95% to 100% (according to NMR spectrum).

The following Formulation Examples illustrate the preparation of such formulations:

I. 20 parts by weight of the compound No. 5.01 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. 5.04 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 5.11 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 5.13 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. 5.26 are mixed with 97 parts by weight of finely divided kaolin. This gives a dust which comprises 3% by weight of the active ingredient.

VI. 20 parts by weight of the active ingredient No. 5.24 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active ingredient No. 5.15 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active ingredient No. 5.07 is dissolved in a mixture composed of 80 parts by weight of cyclohexanone and 20 parts by weight of Wettol® EM 31 (=nonionic emulsifier based on ethoxylated castor oil; BASF AG). This gives a stable emulsion concentrate.

The herbicidal compositions or the active ingredients of the formula I can be applied pre- or post-emergence. If the active ingredients are less well tolerated by certain crop plants, application techniques may be used in which the herbicidal compositions are sprayed, with the aid of spraying apparatus, in such a way that they come into as little contact as possible, if any, with the leaves of the sensitive crop plants, while the active ingredients reach the leaves of undesirable plants which grow underneath, or the exposed soil surface (post-directed, lay-by).

Depending on the intended purpose, the season, the target plants and the growth stage, the application rates of active ingredient of the formula I are from 0.001 to 3.0, preferably 0.01 to 1.0, kg of active substance (a.s.) per ha.

To widen the spectrum of action and to achieve synergistic effects, the hetaroyl derivatives of the formula I can be mixed with a large number of representatives of other groups of herbicidal or growth-regulating active ingredients and applied jointly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids, and their derivatives, benzoic acid and its derivatives, benzothiadiazinones, 2-(het)aroyl-1,3-cyclohexanediones, hetaryl aryl ketones, benzylisoxazolidinones, meta-CF$_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonyl-ureas, triazines, triazinones, triazolinones, triazolecarboxamides and uracils.

Furthermore, it may be advantageous to employ the compounds of the formula I, on their own or in combination with other herbicides, also in a mixture with other crop protection agents, for example pesticides or agents for controlling phytopathogenic fungi or bacteria. Also of interest is the miscibility with mineral salt solutions which are employed for treating nutritional and trace element deficiencies. Nonphytotoxic oils and oil concentrates may also be added.

Use Examples

The herbicidal activity of the hetaroyl derivatives of the formula I was demonstrated by the following greenhouse experiments:

The culture containers used were plastic flowerpots containing loamy sand with approximately 3.0% of humus as the substrate. The seeds of the test plants were sown separately for each species.

In the case of pre-emergence treatment, the active ingredients, which were suspended or emulsified in water, were applied directly after sowing by means of finely distributing nozzles. The containers were irrigated gently to promote germination and growth and subsequently covered with transluscent plastic hoods until the plants had rooted. This cover causes [sic] uniform germination of the test plants unless this was adversely affected by the active ingredients.

For the post-emergence treatment, the test plants were first grown to a plant height of from 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment. The application rate for the post-emergence treatment was 0.125 or 0.0625 kg of a.s. (active substance) per ha.

Depending on the species, the plants were kept at from 10 to 25° C. or 20 to 35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage or normal course of growth.

The plants used in the greenhouse experiments belong to the following species:

| Scientific Name | Common Name |
| --- | --- |
| Chenopodium album | lambsquarters (goosefoot) |
| Echinochloa crus-galli | barnyardgrass |
| Polygonum persicaria | ladysthumb |
| Triticum aestivum | summer wheat |
| Zea mays | Indian corn |

At application rates of 0.125 or 0.0625 kg/ha, the compound 5.01 (Table 5) had a very good activity against the abovementioned mono- and dicotyledonous harmful plants and very good tolerability in summer wheat and maize when applied post-emergence.

We claim:

1. Hetaroyl derivatives of the formula

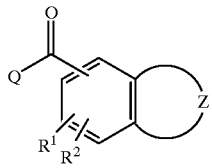

where:

$R^1$ and $R^2$ are each hydrogen, nitro, halogen, cyano, thiocyanato, hydroxyl, mercapto, $C_1$–$C_6$-alkyl, $C_1$–$C_6$-haloalkyl, $C_2$–$C_6$-alkenyl, $C_2$–$C_6$-alkynyl, $C_1$–$C_6$-alkoxy, $C_1$–$C_6$-haloalkoxy, $C_2$–$C_6$-alkenyloxy, $C_2$–$C_6$-alkynyloxy, $C_1$–$C_6$-alkylthio, $C_1$–$C_6$-haloalkylthio, $C_2$–$C_6$-alkenylthio, $C_2$–$C_6$-alkynylthio, $C_1$–$C_6$-alkylsulfinyl, $C_1$–$C_6$-haloalkylsulfinyl, $C_2$–$C_6$-alkenylsulfinyl, $C_2$–$C_6$-alkynylsulfinyl, $C_1$–$C_6$-alkylsulfonyl, $C_1$–$C_6$-haloalkylsulfonyl, $C_2$–$C_6$-alkenylsulfonyl, $C_2$–$C_6$-alkynylsulfonyl, $C_1$–$C_6$-alkoxysulfonyl, $C_1$–$C_6$-haloalkoxysulfonyl, $C_2$–$C_6$-alkenyloxysulfonyl, $C_2$–$C_6$-alkynyloxysulfonyl, phenyl, phenyloxy, phenylthio, phenylsulfinyl or phenylsulfonyl, where the last five substituents may be partially or fully halogenated and may carry one to three of the following groups:

nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

Z is a building block from the group consisting of $Z^1$ to $Z^{12}$

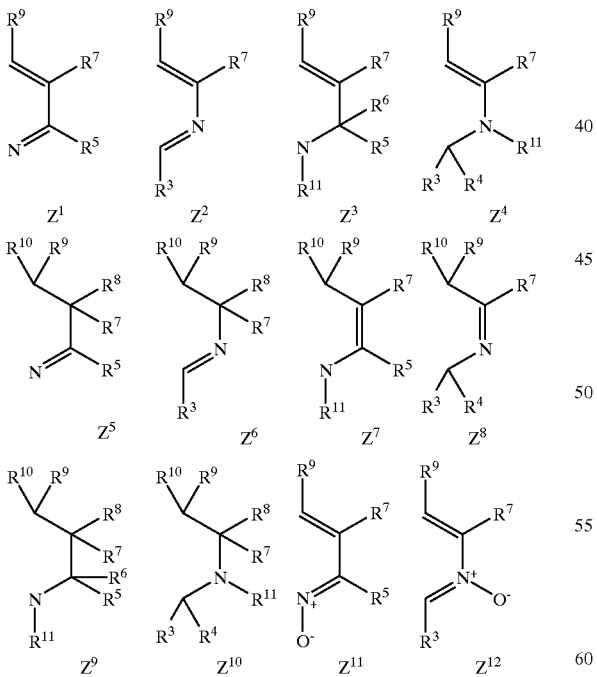

where $R^3$, $R^5$, $R^7$ and $R^9$ are each nitro, cyano, hydroxyl, mercapto, $C_2$–$C_4$-alkenyl, $C_2$–$C_4$-alkynyl, $C_2$–$C_4$-alkenyloxy, $C_2$–$C_4$-alkynyloxy, $C_2$–$C_4$-alkenylthio, $C_2$–$C_4$-alkynylthio, $C_1$–$C_4$-alkylsulfinyl, $C_1$–$C_4$-haloalkylsulfinyl, $C_2$–$C_4$-alkenylsulfinyl, $C_2$–$C_4$-alkynylsulfinyl, $C_1$–$C_4$-alkylsulfonyl, $C_1$–$C_4$-haloalkylsulfonyl, $C_2$–$C_4$-alkenylsulfonyl, $C_2$–$C_4$-alkynylsulfonyl, $C_1$–$C_4$-alkoxysulfonyl, $C_1$–$C_4$-haloalkoxysulfonyl, $C_2$–$C_4$-alkenyloxysulfonyl, $C_2$–$C_4$-alkynyloxysulfonyl, —$NR^{12}R^{13}$, —$CO_2R^{12}$, —$CONR^{12}R^{13}$, phenyl, phenoxy, phenylthio, phenylsulfinyl or phenylsulfonyl, where the last five substituents may be partially or fully halogenated and may carry one to three of the following groups: nitro, cyano, hydroxyl, $C_1$–$C_4$-alkyl, $C_1$–$C_4$-haloalkyl, $C_1$–$C_4$-alkoxy, $C_1$–$C_4$-haloalkoxy; or one of the radicals mentioned under $R^4$;

$R^4$, $R^6$, $R^8$ and $R^{10}$ are each hydrogen, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

or a —$CR^3R^4$—, —$CR^5R^6$—, —$CR^7R^8$— or —$CR^9R^{10}$— unit may be replaced by C=O or C=$NR^{13}$;

$R^{11}$ is hydrogen, $C_1$–$C_6$-alkyl, $C_1$–$C_6$-haloalkyl, $C_3$–$C_6$-alkenyl, $C_3$–$C_6$-alkynyl, $C_1$–$C_6$-alkylcarbonyl, $C_1$–$C_6$-haloalkylcarbonyl, 13 $CO_2R^{12}$, —$CONR^{12}R^{13}$ or $SO_2R^{12}$;

$R^{12}$ is hydrogen, $C_1$–$C_6$-alkyl, $C_1$–$C_6$-haloalkyl, $C_3$–$C_6$-alkenyl, $C_3$–$C_6$-alkynyl or phenyl, where the last radical may be partially or fully halogenated and may carry one to three of the following radicals:

nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

$R^{13}$ is $C_1$–$C_6$-alkoxy, $C_1$–$C_6$-haloalkoxy, $C_3$–$C_6$-alkenyloxy, $C_3$–$C_6$-alkynyloxy or one of the radicals mentioned under $R^{12}$;

Q is a hydroxypyrazole, linked through position 4, of the formula II

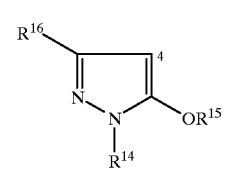

where $R^{14}$ is $C_1$–$C_6$-alkyl, $C_1$–$C_6$-haloalkyl or phenyl, where the last radical may be partially or fully halogenated and may carry one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy;

$R^{15}$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenyl-$C_1$–$C_4$-alkyl, phenylcarbonyl-$C_1$–$C_4$-alkyl, phenylcarbonyl, phenoxycarbonyl or phenylsulfonyl, where the last five substituents may be partially or fully halogenated and may carry one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy;

$R^{16}$ is hydrogen, $C_1$–$C_6$-alkyl or $C_1$–$C_6$-haloalkyl;

and their agriculturally useful salts.

2. Hetaroyl derivatives of the formula I as claimed in claim 1, where:

$R^1$ and $R^2$ are each hydrogen, nitro, halogen, cyano, thiocyanato, hydroxyl, mercapto, $C_1$–$C_6$-alkyl, $C_1$–$C_6$-haloalkyl, $C_2$–$C_6$-alkenyl, $C_2$–$C_6$-alkynyl, $C_1$–$C_6$-alkoxy, $C_1$–$C_6$-haloalkoxy, $C_2$–$C_6$-alkenyloxy, $C_2$–$C_6$-alkynyloxy, $C_1$–$C_6$-alkylthio, $C_1$–$C_6$-haloalkyl-thio, $C_2$–$C_6$-alkenylthio, $C_2$–$C_6$-alkynylthio, $C_1$–$C_6$-alkylsulfinyl, $C_1$–$C_6$-haloalkylsulfinyl, $C_2$–$C_6$-alkenylsulfinyl, $C_2$–$C_6$-alkynylsulfinyl, $C_1$–$C_6$-alkylsulfonyl, $C_1$–$C_6$-haloalkylsulfonyl, $C_2$–$C_6$-alkenylsulfonyl, $C_2$–$C_6$-alkynylsulfonyl, $C_1$–$C_6$-alkoxysulfonyl, $C_1$–$C_6$-haloalkoxysulfonyl, $C_2$–$C_6$-alkenyloxysulfonyl, $C_2$–$C_6$-alkynyloxysulfonyl, phenyl, phenyloxy, phenylthio, phenylsulfinyl or phenylsulfonyl, where the last five substituents may be partially or fully halogenated and may carry one to three of the following groups:

nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

Z is a building block from the group consisting of $Z^1$ to $Z^{12}$

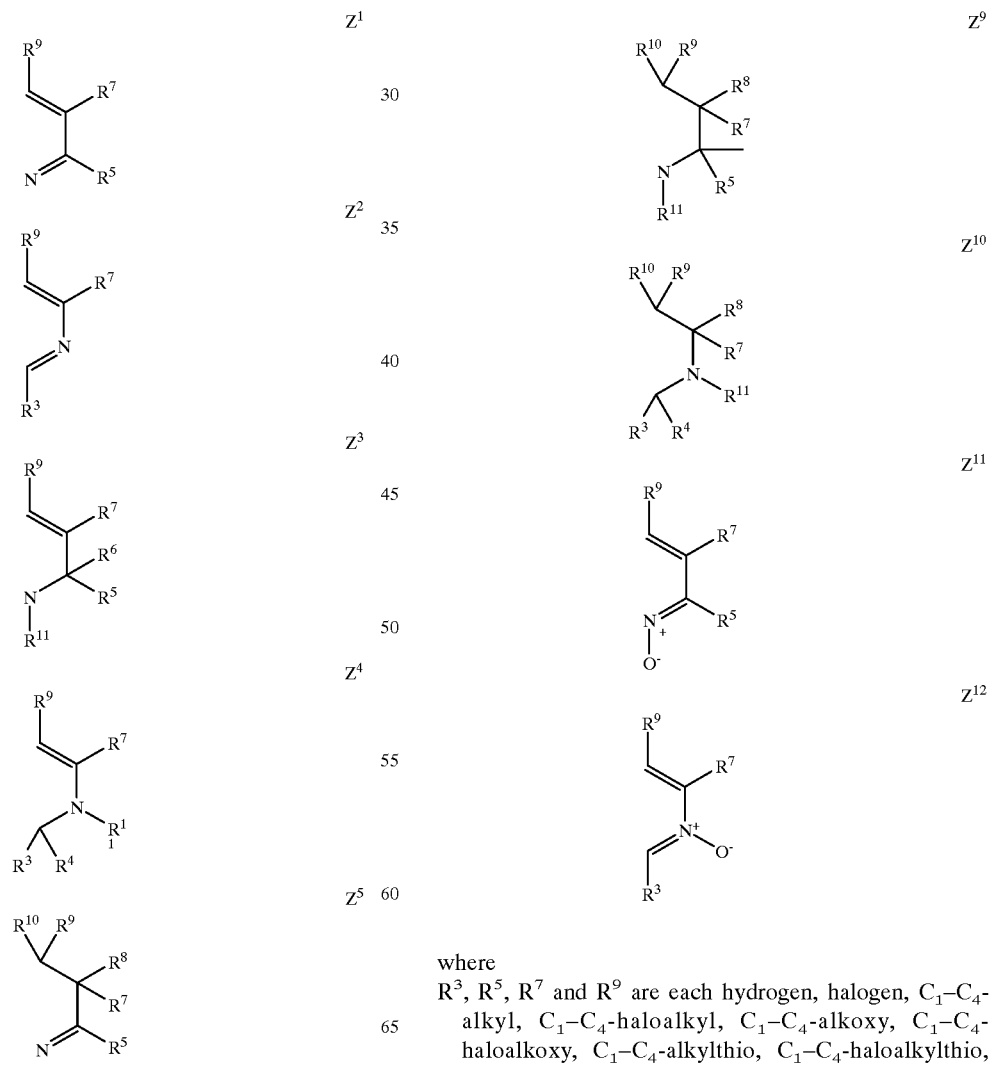

where $R^3$, $R^5$, $R^7$ and $R^9$ are each hydrogen, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, nitro, cyano, hydroxyl, mercapto, $C_2$–$C_4$-alkenyl, $C_2$–$C_4$-alkynyl, $C_2$–$C_4$-alkenyloxy, $C_2$–$C_4$-alkynyloxy, $C_2$–$C_4$-alkenylthio, $C_2$–$C_4$-alkynylthio, $C_1$–$C_4$-alkylsulfinyl, $C_1$–$C_4$-haloalkylsulfinyl, $C_2$–$C_4$-alkenylsulfinyl, $C_2$–$C_4$-alkynylsulfinyl, $C_1$–$C_4$-alkylsulfonyl, $C_1$–$C_4$-haloalkylsulfonyl, $C_2$–$C_4$-alkenylsulfonyl, $C_2$–$C_4$-alkynylsulfonyl, $C_1$–$C_4$-alkoxysulfonyl, $C_1$–$C_4$-haloalkoxysulfonyl, $C_2$–$C_4$-alkenyloxysulfonyl, $C_2$–$C_4$-alkynyloxy-sulfonyl, —$NR^{12}R^{13}$, —$CO_2R^{12}$, —$CONR^{12}R^{13}$, phenyl, phenoxy, phenylthio, phenylsulfinyl or phenylsulfonyl, where the last five substituents may be partially or fully halogenated and may carry one to three of the following groups:

nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

$R^4$, $R^6$, $R^8$ and $R^{10}$ are each hydrogen;

$R^{11}$ is hydrogen, $C_1$–$C_6$-alkyl, $C_1$–$C_6$-haloalkyl, $C_3$–$C_6$-alkenyl, $C_3$–$C_6$-alkynyl, $C_1$–$C_6$-alkylcarbonyl, $C_1$–$C_6$-haloalkylcarbonyl, —$CO_2R^{12}$, —$CONR^{12}R^{13}$ or $SO_2R^{12}$;

$R^{12}$ is hydrogen, $C_1$–$C_6$-alkyl, $C_1$–C6-haloalkyl, $C_3$–$C_6$-alkenyl, $C_3$–$C_6$-alkynyl or phenyl, where the last radical may be partially or fully halogenated and may carry one to three of the following radicals:

nitro, cyano, hydroxyl, $C_1$–$C_4$-alkyl, $C_1$–$c_4$-haloalkyl, $C_1$–$C_4$-alkoxy, $C_1$–$C_4$-haloalkoxy;

$R^{13}$ is $C_1$–$C_6$-alkoxy, $C_1$–$C_6$-haloalkoxy, $C_3$–$C_6$-alkenyloxy, $C_3$–$C_6$-alkynyloxy or one of the radicals mentioned under $R^{12}$;

$R^{14}$ is $C_1$–$C_6$-alkyl, $C_1$–$C_6$-haloalkyl or phenyl, where the last substituent may be partially or fully halogenated and may carry one to three of the following radicals:

nitro, cyano, $C_1$–$C_4$-alkyl, $C_1$–$C_4$-haloalkyl, $C_1$–$C_4$-alkoxy, $C_1$–C4-haloalkoxy;

$R^{15}$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenyl-$C_1$–$C_4$-alkyl, phenylcarbonyl-$C_1$–$C_4$-alkyl, phenylcarbonyl, phenoxycarbonyl or phenylsulfonyl, where the last five substituents may be partially or fully halogenated and may carry one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy;

$R^{16}$ is hydrogen, $C_1$–$C_6$-alkyl or $C_1$–$C_6$-haloalkyl.

3. Hetaroyl derivatives of the formula I as claimed in claim 1, wherein the variable Z is $Z^1$, $Z^2$, $Z^{11}$ or $Z^{12}$.

4. Hetaroyl derivatives of the formula I as claimed in claim 1, wherein the variable Z is $Z^3$, $Z^4$, $Z^5$, $Z^6$, $Z^7$ or $Z^8$.

5. Hetaroyl derivatives of the formula I as claimed in claim 1, wherein the variable Z is $z^3$, $Z^5$, $Z^6$, $Z^7$ or $Z^8$.

6. Hetaroyl derivatives of the formula I as claimed in claim 1, wherein the variable Z is $Z^9$ or $Z^{10}$.

7. Hetaroyl derivatives of the formula Ia as claimed in claim 1 and their N-oxides (formula Ia')

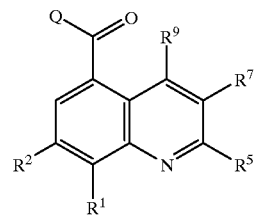

Ia

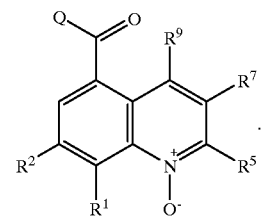

Ia'

8. Hetaroyl derivatives of the formula Ib as claimed in claim 1 and their N-oxides (formula Ib')

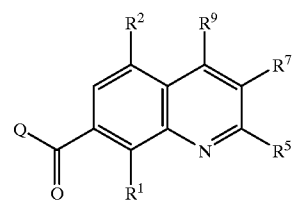

Ib

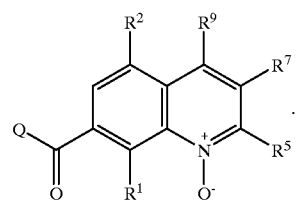

Ib'

9. Hetaroyl derivatives of the formula Ic as claimed in claim 1 and their N-oxides (formula Ic')

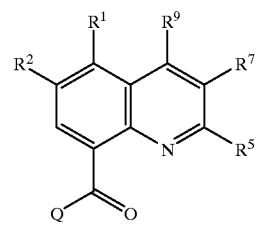

Ic

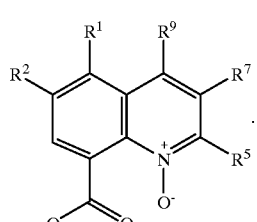

Ic'

10. Hetaroyl derivatives of the formula Id as claimed in claim 1 and their N-oxides (formula Id')

Id

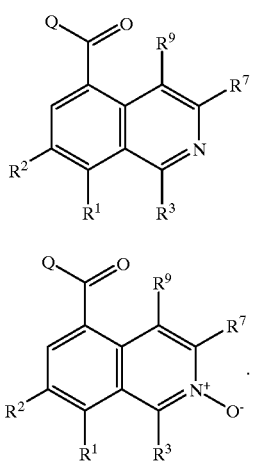

Id'

11. Hetaroyl derivatives of the formula Ie as claimed in claim 1 and their N-oxides (formula Ie')

Ie

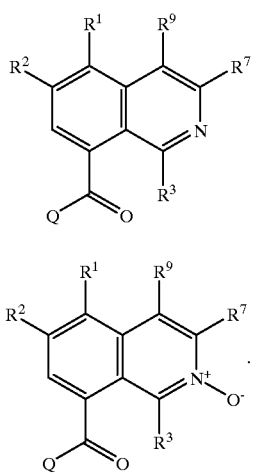

Ie'

12. Hetaroyl derivatives of the formula If (where Z=Z$^9$) or Ig (where Z=Z$^{10}$) as claimed in claim 1

If

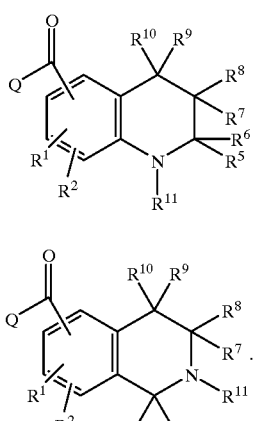

Ig

13. A process for preparing hetaroyl derivatives of the formula I (where R$^{15}$=H) as claimed in claim 1, which comprises acylating a hydroxypyrazole of the formula II (where R$^{15}$=H)

II

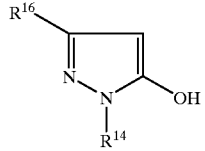

with an activated carboxylic acid IIIa or with a carboxylic acid IIIb

IIIa

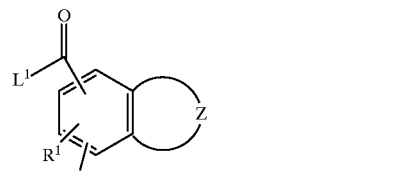

IIIb

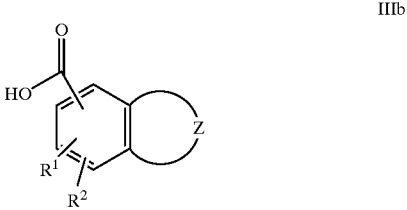

where the variables R$^1$, R$^2$ and Z are each as defined in claim 1 and L$^1$ is a nucleophilically replaceable leaving group and the acylation product is rearranged in the presence of a catalyst to give the compounds I.

14. A process for preparing hetaroyl derivatives of the formula I (where R$^{15}$≠H) as claimed in claim 1, which comprises reacting a hetaroyl derivative of the formula I (where R$^{15}$=H)

I

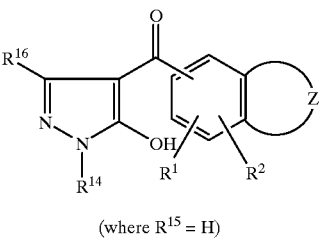

(where R$^{15}$ = H)

with a compound of the formula IV (where R$^{15}$≠H)

L$^2$—R$^{15}$  IV (where R$^{15}$≠H)

where L$^2$ is a nucleophilically replaceable leaving group.

15. A herbicidal composition comprising a herbicidally active amount of at least one hetaroyl derivative of the formula I or of an agriculturally useful salt of I as claimed in claim 1 and at least one inert liquid and/or solid carrier and, if desired, at least one surfactant.

16. A process for preparing herbicidally active compositions as claimed in claim 15, which comprises mixing a herbicidally active amount of at least one hetaroyl derivative of the formula I or of an agriculturally useful salt of I

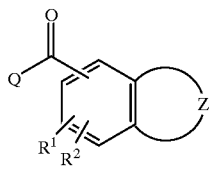

I and at least one inert liquid and/or solid carrier and, if desired, at least one surfactant.

17. A method for controlling undesirable plant growth, which comprises allowing a herbicidally active amount of at least one hetaroyl derivative of the formula I or of an agriculturally useful salt of I as claimed in claim 1 act on plants, their habitat or on seeds.

* * * * *

UNITED STATES PATENT AND TRADEMARK OFFICE
CERTIFICATE OF CORRECTION

PATENT NO. : 6,262,074 B1
DATED : July 17, 2001
INVENTOR(S) : Otten et al.

It is certified that error appears in the above-identified patent and that said Letters Patent is hereby corrected as shown below:

Column 138, claim 1,
Line 24, delete "13".

Column 139,
Formula $Z^4$ shown on lines 51-59 should be:

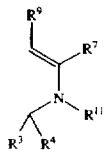

Column 140,
Formula $Z^9$ shown on lines 29-34 should be:

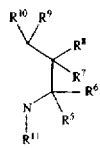

Column 141, claim 2,
Line 26, "$C_1$-C6-haloalkyl" should be -- $C_1$-$C_6$-haloalkyl --.

Column 141, claim 5,
Line 63, "$z^3$" should be -- $Z^3$ --.

Column 146, claim 17,
Line 8, after "claim 1" insert -- to --.

Signed and Sealed this

Nineteenth Day of March, 2002

Attest:

JAMES E. ROGAN
Director of the United States Patent and Trademark Office

Attesting Officer